United States Patent
Wang

(10) Patent No.: US 6,821,518 B1
(45) Date of Patent: Nov. 23, 2004

(54) COMPOUNDS AND METHODS FOR THERAPY AND DIAGNOSIS OF LUNG CANCER

(75) Inventor: Tongtong Wang, Medina, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/285,479

(22) Filed: Apr. 2, 1999

Related U.S. Application Data

(63) Continuation of application No. PCT/US99/05798, filed on Mar. 17, 1999, which is a continuation-in-part of application No. 09/221,107, filed on Dec. 22, 1998, which is a continuation-in-part of application No. 09/123,912, filed on Jul. 27, 1998, now Pat. No. 6,312,695, which is a continuation-in-part of application No. 09/040,802, filed on Mar. 18, 1998, now abandoned.

(51) Int. Cl.$^7$ ............................ A61K 39/00; C07K 1/00
(52) U.S. Cl. .............................. 424/185.1; 424/184.1; 424/277.1; 530/350
(58) Field of Search ........................ 435/69.1; 530/350; 424/184.1, 185.1, 277.1

(56) References Cited

U.S. PATENT DOCUMENTS

| | | | |
|---|---|---|---|
| 5,705,159 A | 1/1998 | Irie et al. ................. | 424/185.1 |
| 5,783,422 A | 7/1998 | Suminami et al. ......... | 435/69.3 |
| 5,928,894 A | * 7/1999 | Lal et al. .................... | 435/69.1 |

FOREIGN PATENT DOCUMENTS

| | | |
|---|---|---|
| EP | 0695760 A1 | 2/1996 |
| WO | WO 91/18926 | 12/1991 |
| WO | WO 94/06929 | 3/1994 |
| WO | WO 95/21862 | 8/1995 |
| WO | WO 96/02552 | 2/1996 |
| WO | WO 96/28473 | 9/1996 |
| WO | WO 96/30389 | 10/1996 |
| WO | WO 97/07244 | 2/1997 |
| WO | WO 98/35985 | 8/1998 |
| WO | WO 99/38973 | 8/1999 |
| WO | WO 99/47674 | 9/1999 |
| WO | WO 98/46788 | 10/1999 |

OTHER PUBLICATIONS

Kaye et al., A singel amino acid substitution results in a retinablastoma protein defective in phosphorylation and oncoprotein binding, Sep. 1990, Proc. Natl. Acad. Sci., vol. 87, pp. 6922–6926.*
Rudinger et al., Characteristics of the amino acids as components of a peptide hormone sequence, 1976, Biological Council, pp. 1–7.*
Lal, Preeti, Patent No. 5928894, Sequence 5.*
Winteroe et al., Nov. 1, 1996, AC No. Q29274.*
Wineroe et al., AC Q29274, SPTREMBL_15.*
Waterman et al., GenEmbl Accession No. X76534, Feb. 1995.*
Hillier et al., EST Accession No. R70993, Jun. 1995.*
GenBank Accession No. AF043977, Jun. 23, 1999.
GenBank Accession No. U85946, Jul. 30, 1999.
Geneseq Accession No. AAZ24653, Dec. 7, 1999.
Gruber et al., "Molecular cloning and transmembrane structure of hCLCA2 from human lung, trachea, and mammary gland," *Am. J. Physiol.* 276(Cell Physiol 45):C1261–C1270, 1999.
Guo et al., "Identification and characterization of homologues of the Exocyst component Sec10p," *FEBS Letters* 404(2–3):135–139, 1997.
Gerhold and Caskey, "It's the genes! EST access to human genome content," *BioEssays* 18(12):973–981, 1996.
Russell and Barton, "Structural features can be unconserved in protein with similar folds," *J. Mol. Biol.* 244:332–350, 1994.
Wells and Peitsch, "The chemokine information source: identification and characterization of novel chemokines using the WorldWideWeb and expressed sequence tag databases," *Journal of Leukocyte Biology* 61:545–550, May 1997.
Baldi et al., "Differential expression of Rb2/p130 and p107 in normal human tissue and in primary lung cancer," *Clinical Cancer Research* 3(10):1691–1697, Oct. 1997.
Database EMBL Nucleotide and Protein Sequence, Accession No. AI468638, Mar. 17, 1999.
Hara et al., "Characterization of cell phenotype by a novel cDNA library subtraction system: expression of CD8α in a mast cell–derived interleukin–4–dependent cell line," *Blood* 84(1):189–199, Jul. 1, 1994.
Henderson et al., "Identification of lung tumor antigens for cancer immunotherapy: immunological and molecular approaches," *Immunological Investigation* 29(2):87–91, May 2000.
Hogan et al., "The peptide recognized by HLA–A68.2–restricted, squamous cell carcinoma of the lung–specific cytotoxic T lymphocytes is derived from a mutated elongation factor 2 gene," *Cancer Research* 58(22):5144–5150, Nov. 15, 1998.
Lelievre et al., "Structural properties of chimeric peptides containing a T–cell epitope linked to a fusion peptide and their importance for in vivo induction of cytotoxic T–cell responses," *European Journal of Biochemistry* 249(3):895–904, 1997.

(List continued on next page.)

*Primary Examiner*—Scott D. Priebe
*Assistant Examiner*—Shin-Lin Chen
(74) *Attorney, Agent, or Firm*—SEED Intellectual Property Law Group PLLC

(57) ABSTRACT

Compounds and methods for the treatment and diagnosis of lung cancer are provided. The inventive compounds include polypeptides containing at least a portion of a lung tumor protein. Vaccines and pharmaceutical compositions for immunotherapy of lung cancer comprising such polypeptides, or DNA molecules encoding such polypeptides, are also provided, together with DNA molecules for preparing the inventive polypeptides.

4 Claims, No Drawings

OTHER PUBLICATIONS

Marshall and Hodgson, "DNA chips: an array of possibilities," *Nature Biotechnology* 16 27 Jan. 31, 1998.

Ramsay, G., "DNA chips: state-of-the art," *Nature Biotechnology* 16:40–44, Jan. 1998.

Visseren et al., "Identification of HLA–A *0201–restricted CTL epitopes encoded by the tumor–specific MAGE–2 gene product," *International Journal of Cancer* 73(1):125–130, 1997.

Wang et al., "Identification of genes differentially over–expressed in lung squamous cell carcinoma using combination of cDNA subtraction and microarray analysis," *Oncogene* 19(12):1519–1528, Mar. 16, 2000.

Database EMBLest17 Accession No. W22264:Human retina cDNA Tsp509I–cleaved Homo sapiens cDNA not directional, May 9, 1996.

Database EMBLest17 Accession No. AA340797: EST46165 Fetal Kidney II Homo Sapiens cDNA 3' end, Apr. 18, 1997.

Brass et al., "Translation initiation factor e1F–4gamma is encoded by an amplified gene and induces an immune response in squamous cell lung carcinoma," *Human Molecular Genetics* 6(1):33–39, 1997.

Finch et al., "Identification of a cloned sequence activated during multi–stage carcinogenesis in mouse skin," *Carcinogenesis* 12(8):1519–1522, 1991.

* cited by examiner

COMPOUNDS AND METHODS FOR THERAPY AND DIAGNOSIS OF LUNG CANCER

REFERENCE TO RELATED APPLICATIONS

This application claims priority from and is a continuation of PCT/US99/05798, filed Mar. 17, 1999, which claims priority from and is a CIP of U.S. patent application Ser. No. 09/221,107, filed Dec. 22, 1998, which is a CIP of U.S. patent application Ser. No. 09/123,912, filed Jul. 27, 1998, now U.S. Pat. No. 6,312,695; which is a CIP of U.S. patent application Ser. No. 09/040,802, filed Mar. 18, 1998, now abandoned.

TECHNICAL FIELD

The present invention relates generally to compositions and methods for the treatment and diagnosis of lung cancer. The invention is more specifically related to nucleotide sequences that are preferentially expressed in lung tumor tissue, together with polypeptides encoded by such nucleotide sequences. The inventive nucleotide sequences and polypeptides may be used in vaccines and pharmaceutical compositions for the treatment and diagnosis of lung cancer.

BACKGROUND OF THE INVENTION

Lung cancer is the primary cause of cancer death among both men and women in the U.S., with an estimated 172,000 new cases being reported in 1994. The five-year survival rate among all lung cancer patients, regardless of the stage of disease at diagnosis, is only 13%. This contrasts with a five-year survival rate of 46% among cases detected while the disease is still localized. However, only 16% of lung cancers are discovered before the disease has spread.

Early detection is difficult since clinical symptoms are often not seen until the disease has reached an advanced stage. Currently, diagnosis is aided by the use of chest x-rays, analysis of the type of cells contained in sputum and fiberoptic examination of the bronchial passages. Treatment regimens are determined by the type and stage of the cancer, and include surgery, radiation therapy and/or chemotherapy. In spite of considerable research into therapies for the disease, lung cancer remains difficult to treat.

Accordingly, there remains a need in the art for improved vaccines, treatment methods and diagnostic techniques for lung cancer.

SUMMARY OF THE INVENTION

Briefly stated, the present invention provides compounds and methods for the therapy of lung cancer. In a first aspect isolated polynucleotide molecules encoding lung tumor polypeptides are provided, such polynucleotide molecules comprising a nucleotide sequence selected from the group consisting of: (a) sequences provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168 and 171; (b) sequences complementary to a sequence provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168 and 171; and (b) sequences that hybridize to a sequence of (a) or (b) under moderately stringent conditions.

In a second aspect, isolated polypeptides are provided that comprise at least an immunogenic portion of a lung tumor protein or a variant thereof. In specific embodiments, such polypeptides comprise an amino acid sequence encoded by a polynucleotide molecule comprising a nucleotide sequence selected from the group consisting of (a) sequences recited in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168 and 171; (b) sequences complementary to a sequence provided in SEQ ID NO: 1–3, 6–8, 10–13, 15–27, 29, 30, 32, 34–49, 51, 52, 54, 55, 57–59, 61–69, 71, 73, 74, 77, 78, 80–82, 84, 86–96, 107–109, 111, 113, 125, 127, 128, 129, 131–133, 142, 144, 148–151, 153, 154, 157, 158, 160, 167, 168 and 171; and (c) sequences that hybridize to a sequence of (a) or (b) under moderately stringent conditions.

In related aspects, expression vectors comprising the inventive polynucleotide molecules, together with host cells transformed or transfected with such expression vectors are provided. In preferred embodiments, the host cells are selected from the group consisting of E. coli, yeast and mammalian cells.

In another aspect, fusion proteins comprising a first and a second inventive polypeptide or, alternatively, an inventive polypeptide and a known lung tumor antigen, are provided.

The present invention further provides pharmaceutical compositions comprising one or more of the above polypeptides, fusion proteins or polynucleotide molecules and a physiologically acceptable carrier, together with vaccines comprising one or more such polypeptides, fusion proteins or polynucleotide molecules in combination with an immune response enhancer.

In related aspects, the present invention provides methods for inhibiting the development of lung cancer in a patient, comprising administering to a patient an effective amount of at least one of the above pharmaceutical compositions and/or vaccines.

Additionally, the present invention provides methods for immunodiagnosis of lung cancer, together with kits for use in such methods. Polypeptides are disclosed which comprise at least an immunogenic portion of a lung tumor protein or a variant of said protein that differs only in conservative substitutions and/or modifications, wherein the lung tumor protein comprises an amino acid sequence encoded by a polynucleotide molecule having a sequence selected from the group consisting of nucleotide sequences recited in SEQ ID NO: 1–109, 111, 113, 115–151, 153, 154, 157, 158, 160, 162–164, 167, 168 and 171, and variants thereof. Such polypeptides may be usefully employed in the diagnosis and monitoring of lung cancer.

In one specific aspect of the present invention, methods are provided for detecting lung cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of lung cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of lung cancer.

The present invention further provides methods for detecting lung cancer comprising: (a) obtaining a biological sample from a patient; (b) contacting the sample with a first and a second oligonucleotide primer in a polymerase chain reaction, at least one of the oligonucleotide primers being specific for a polynucleotide molecule that encodes one of the above polypeptides; and (c) detecting in the sample a polynucleotide sequence that amplifies in the presence of the first and second oligonucleotide primers. In a preferred embodiment, at least one of the oligonucleotide primers comprises at least about 10 contiguous nucleotides of a polynucleotide molecule including a sequence selected from the group consisting of SEQ ID NO: 1–109, 111, 113, 115–151, 153, 154, 157, 158, 160, 162–164, 167, 168 and 171.

In a further aspect, the present invention provides a method for detecting lung cancer in a patient comprising: (a) obtaining a biological sample from the patient; (b) contacting the sample with an oligonucleotide probe specific for a polynucleotide molecule that encodes one of the above polypeptides; and (c) detecting in the sample a polynucleotide sequence that hybridizes to the oligonucleotide probe. Preferably, the oligonucleotide probe comprises at least about 15 contiguous nucleotides of a polynucleotide molecule having a partial sequence selected from the group consisting of SEQ ID NO: 1–109, 111, 113, 115–151, 153, 154, 157, 158, 160, 162–164, 167, 168 and 171.

In related aspects, diagnostic kits comprising the above oligonucleotide probes or primers are provided.

In yet a further aspect, methods for the treatment of lung cancer in a patient are provided, the methods comprising obtaining PBMC from the patient, incubating the PBMC with a polypeptide of the present invention (or a polynucleotide that encodes such a polypeptide) to provide incubated T cells and administering the incubated T cells to the patient. The present invention additionally provides methods for the treatment of lung cancer that comprise incubating antigen presenting cells with a polypeptide of the present invention (or a polynucleotide that encodes such a polypeptide) to provide incubated antigen presenting cells and administering the incubated antigen presenting cells to the patient. In certain embodiments, the antigen presenting cells are selected from the group consisting of dendritic cells and macrophages. Compositions for the treatment of lung cancer comprising T cells or antigen presenting cells that have been incubated with a polypeptide or polynucleotide of the present invention are also provided. These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for the therapy and diagnosis of lung cancer. The compositions described herein include polypeptides, fusion proteins and polynucleotide molecules. Also included within the present invention are molecules (such as an antibody or fragment thereof) that bind to the inventive polypeptides. Such molecules are referred to herein as "binding agents."

In one aspect, the subject invention discloses polypeptides comprising an immunogenic portion of a human lung tumor protein, wherein the lung tumor protein includes an amino acid sequence encoded by a polynucleotide molecule including a sequence selected from the group consisting of (a) nucleotide sequences recited in SEQ ID NO: 1–109, 111, 113 115–151, 153, 154,157, 158, 160, 162–164, 167, 168 and 171, (b) the complements of said nucleotide sequences, and (c) variants of such sequences. As used herein, the term "polypeptide" encompasses amino acid chains of any length, including full length proteins, wherein the amino acid residues are linked by covalent peptide bonds. Thus, a polypeptide comprising a portion of one of the above lung tumor proteins may consist entirely of the portion, or the portion may be present within a larger polypeptide that contains additional sequences. The additional sequences may be derived from the native protein or may be heterologous, and such sequences may (but need not) be immunoreactive and/or antigenic. As detailed below, such polypeptides may be isolated from lung tumor tissue or prepared by synthetic or recombinant means.

As used herein, an "immunogenic portion" of a lung tumor protein is a portion that is capable of eliciting an immune response in a patient inflicted with lung cancer and as such binds to antibodies present within sera from a lung cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of lung cancer patients. Methods for preparing and identifying immunogenic portions of antigens of known sequence are well known in the art and include those summarized in Paul, *Fundamental Immunology*, $3^{rd}$ ed., Raven Press, 1993, pp. 243–247.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides. A polypeptide "variant," as used herein, is a polypeptide that differs from the recited polypeptide only in conservative substitutions and/or modifications, such that the therapeutic, antigenic and/or immunogenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as describe below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the-polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The antigens provided by the present invention include variants that are encoded by polynucleotide sequences which are substantially homologous to one or more of the polynucleotide sequences specifically recited herein. "Substantial homology," as used herein, refers to polynucleotide sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing polynucleotide sequences are also within the scope of this invention, as are nucleotide sequences that, due to code degeneracy, encode an immunogenic polypeptide that is encoded by a hybridizing polynucleotide sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1 973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Also included in the scope of the present invention are alleles of the genes encoding the nucleotide sequences recited in herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence.

For lung tumor polypeptides with immunoreactive properties, variants may, alternatively, be identified by modifying the amino acid sequence of one of the above polypeptides, and evaluating the immunoreactivity of the modified polypeptide. For lung tumor polypeptides useful for the generation of diagnostic binding agents, a variant may be identified by evaluating a modified polypeptide for the ability to generate antibodies that detect the presence or absence of lung cancer. Such modified sequences may be prepared and tested using, for example, the representative procedures described herein.

The lung tumor polypeptides of the present invention, and polynucleotide molecules encoding such polypeptides, may be isolated from lung tumor tissue using any of a variety of methods well known in the art. Polynucleotide sequences corresponding to a gene (or a portion thereof) encoding one of the inventive lung tumor proteins may be isolated from a lung tumor cDNA library using a subtraction technique as described in detail below. Examples of such polynucleotide sequences are provided in SEQ ID NO: 1–109,111,113 115–151, 153, 154, 157, 158, 160, 162–164, 167, 168 and 171. Partial polynucleotide sequences thus obtained may be used to design oligonucleotide primers for the amplification of full-length polynucleotide sequences from a human genomic DNA library or from a lung tumor cDNA library in a polymerase chain reaction (PCR), using techniques well known in the art (see, for example, Mullis et al., *Cold Spring Harbor Symp. Quant. Biol.* 51:263, 1987; Erlich ed., *PCR Technology*, Stockton Press, NY, 1989). For this approach, sequence-specific primers may be designed based on the nucleotide sequences provided herein and may be purchased or synthesized.

An amplified portion may be used to isolate a full length gene from a suitable library (e.g., a lung tumor cDNA library) using well known techniques: Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using techniques well known in the art (see, for example, Mullis et al., *Cold Spring Harbor Symp. Quant. Biol.* 51:263, 1987; Erlich ed., *PCR Technology*, Stockton Press, NY, 1989), and software well known in the art may also be employed. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Transcription-Mediated Amplification, or TMA is another method that may be utilized for the amplification of DNA, rRNA, or mRNA, as described in Patent No. PCT/US91/03184. This autocatalytic and isothermic non-PCR based method utilizes two primers and two enzymes: RNA polymerase and reverse transcriptase. One primer contains a promoter sequence for RNA polymerase. In the first amplification, the promoter-primer hybridizes to the target rRNA at a defined site. Reverse transcriptase creates a DNA copy of the target rRNA by extension from the 3' end of the promoter-primer. The RNA in the resulting complex is degraded and a second primer binds to the DNA copy. A new strand of DNA is synthesized from the end of the primer by reverse transcriptase creating double stranded DNA. RNA polymerase recognizes the promoter sequence in the DNA template and initiates transcription. Each of the newly synthesized RNA amplicons re-enters the TMA process and serves as a template for a new round of replication leading to the expotential expansion of the RNA amplicon. Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Once a polynucleotide sequence encoding a polypeptide is obtained, the polypeptide may be produced recombinantly by inserting the polynucleotide sequence into an expression vector and expressing the polypeptide in an appropriate host. Any of a variety of expression vectors known to those of ordinary skill in the art may be employed to express recombinant polypeptides of this invention. Expression may be achieved in any appropriate host cell that has been transformed or transfected with an expression vector containing a polynucleotide molecule that encodes the recombinant polypeptide. Suitable host cells include prokaryotes, yeast, insect and higher eukaryotic cells. Preferably, the host cells employed are *E. coli*, yeast or a mammalian cell line, such as COS or CHO cells. The polynucleotide sequences expressed in this manner may encode naturally occurring polypeptides, portions of naturally occurring polypeptides, or other variants thereof. Supernatants from suitable host/vector systems which secrete the recombinant polypeptide may first be concentrated using a commercially available filter. The concentrate may then be applied to a suitable purification matrix, such as an affinity matrix or ion exchange resin. Finally, one or more reverse phase HPLC steps can be employed to further purify the recombinant polypeptide.

The lung tumor polypeptides disclosed herein may also be generated by synthetic means. In particular, synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

In addition, lung tumor antigens may be identified by T cell expression cloning. One source of tumor specific T cells is from surgically excised tumors from human patients. In one method for isolating and characterizing tumor specific T cells, the excised tumor is minced and enzymatically digested for several hours to release tumor cells and infiltrating lymphocytes (tumor infiltrating T cells, or TILs). The cells are washed in HBSS buffer and passed over a Ficoll (100%/75%/HBSS) discontinuous gradient to separate tumor cells and lymphocytes from non-viable cells. Two bands are harvested from the interfaces; the upper band at the 75%/HBSS interface contains predominantly tumor cells, while the lower band at the 100%/75%/HBSS interface contains a majority of lymphocytes. The TILs are expanded in culture by techniques well known in the art, but preferably in culture media supplemented with 10 ng/ml IL-7 and 100 U/ml IL-2, or alternatively, cultured and expanded in tissue culture plates that have been pre-adsorbed with anti-CD3 monoclonal antibody (OKT3). The resulting TIL cultures are analyzed by FACS to confirm that the vast majority are CD8+ T cells (>90% of gated population).

In addition, the tumor cells are also expanded in culture using standard techniques well known in the art to establish a tumor cell line, which is later confirmed to be lung carcinoma cells by immunohistochemical analysis. The tumor cell line is transduced with a retroviral vector to express human CD80. The tumor cell line is further characterized by FACS analysis to confirm the strong expression levels of CD80, class I and II MHC molecules.

The specificity of the TIL lines to lung tumor is confirmed by INF-γ and/or TNF-α cytokine release assays. For example, TIL cells from day 21 cultures are co-cultured with either autologous or allogeneic tumor cells, EBV-immortalized LCL, or control cell lines Daudi and K562 and the culture supernatant monitored by ELISA for the presence of cytokines. The expression of these specific cytokines in the presence of tumor or negative control cells indicates whether the TIL lines are tumor specific and potentially recognizing tumor antigen presented by the autologous MHC molecules.

The characterized tumor-specific TIL lines can be expanded and cloned by methods well known in the art. For example, the TIL lines may be expanded to suitable numbers for T cell expression cloning by using soluble anti-CD3 antibody in culture with irradiated EBV transformed LCLs and PBL feeder cells in the presence of 20 U/ml IL-2. Clones from the expanded TIL lines can be generated by standard limiting dilution techniques. In particular, TIL cells are seeded at 0.5 cells/well in a 96-well U bottom plate and stimulated with CD-80-transduced autologous tumor cells, EBV transformed LCL, and PBL feeder cells in the presence of 50 U/ml IL-2. These clones may be further analyzed for tumor specificity by $^{51}Cr$ microcytotoxicity and IFN-γ bioassays. Additionally, the MHC restriction element recognized by the TIL clones may be determined by antibody blocking studies well known in the art.

The CTL lines or clones described above may be employed to identify tumor specific antigens. For example, autologous fibroblasts or LCL from a patient may be transfected or transduced with polynucleotide fragments derived from a lung tumor cDNA library to generate target cells expressing tumor polypeptides. The target cells expressing tumor polypeptides in the context of MHC will be recognized by the CTL line or clone resulting in T-cell activation, which can be monitored by cytokine detection assays. The tumor gene being expressed by the target cell and recognized by the tumor-specific CTL is then isolated by techniques described above. In general, regardless of the method of preparation, the polypeptides disclosed herein are prepared in an isolated, substantially pure form (i.e., the polypeptides, are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known lung tumor antigen, together with variants of such fusion proteins. The fusion proteins of the present invention may (but need not) include a linker peptide between the first and second polypeptides.

A polynucleotide sequence encoding a fusion protein of the present invention is constructed using known recombinant DNA techniques to assemble separate polynucleotide sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated polynucleotide sequences are operably linked to suitable transcriptional or translational regulatory elements. The regulatory elements responsible for expression of polynucleotide are located only 5' to the DNA sequence encoding the first polypeptides. Similarly, stop codons require to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91 (1997)).

Polypeptides of the present invention that comprise an immunogenic portion of a lung tumor protein may generally be used for therapy of lung cancer, wherein the polypeptide stimulates the patient's own immune response to lung tumor cells. The present invention thus provides methods for using one or more of the compounds described herein (which may be polypeptides, polynucleotide molecules or fusion proteins) for immunotherapy of lung cancer in a patient. As used herein, a "patient" refers to any warm-blooded animal, preferably a human. A patient may be afflicted with disease, or may be free of detectable disease. Accordingly, the compounds disclosed herein may be used to treat lung cancer or to inhibit the development of lung cancer. The compounds are preferably administered either prior to or following surgical removal of primary tumors and/or treatment by administration of radiotherapy and conventional chemotherapeutic drugs.

In these aspects, the inventive polypeptide is generally present within a pharmaceutical composition or a vaccine. Pharmaceutical compositions may comprise one or more polypeptides, each of which may contain one or more of the above sequences (or variants thereof), and a physiologically acceptable carrier. The vaccines may comprise one or more such polypeptides and a non-specific immune-response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of lung tumor antigens, either incorporated into a fusion protein as described above (i.e., a single polypeptide that contains multiple epitopes) or present within a separate polypeptide.

Alternatively, a pharmaceutical composition or vaccine may contain polynucleotide encoding one or more of the above polypeptides and/or fusion proteins, such that the polypeptide is generated in situ. In such pharmaceutical compositions and vaccines, the polynucleotide may be present within any of a variety of delivery systems known to those of ordinary skill in the art, including nucleic acid expression systems, bacteria and viral expression systems. Appropriate nucleic acid expression systems contain the necessary polynucleotide sequences for expression in the patient (such as a suitable promoter). Bacterial delivery systems involve the administration of a bacterium (such as Bacillus-Calmette-Guerrin) that expresses an epitope of a lung cell antigen on its cell surface. In a preferred embodiment, the polynucleotides may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating polynucleotide into such expression systems are well known to those of ordinary skill in the art. The polynucleotides may also be "naked," as described, for example, in published PCT application WO 90/11092, and Ulmer et al., *Science* 259:1745–1749, 1993, reviewed by Cohen, *Science* 259:1691–1692, 1993. The uptake of naked polynucleotides may be increased by coating the polynucleotides onto biodegradable beads which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or polynucleotide that is effective to raise an immune response (cellular and/or humoral) against lung tumor cells in a treated patient. A suitable immune response is at least 10–50% above the basal (i.e., untreated) level. In general, the amount of polypeptide present in a dose (or produced in situ by the polynucleotide molecule(s) in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcuim, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of immune-response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.). Polypeptides and polynucleotides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, gamma/delta T lymphocytes, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or transduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews*, 157:177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al, (*Crit. Rev. Oncol. Hematol.*, 22(3), 213, 1996). Cells of the immune system, such as T cells, may be isolated from, the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from tumor specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother*, 45(3–4):131–6, 1997 and Hwu, P., et al, *Cancer Res*, 55(15):3369–73, 1995. Another embodiment may include the transfection of tumor antigen specific alpha and beta T cell receptor chains into alternate T cells, as in Cole, D J, et al, *Cancer Res*, 55(4):748–52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al, *Immunological Reviews*, 157:177, 1997).

Furthermore, vectors expressing the disclosed polynucleotides may be introduced into stem cells taken from the patient and clonally propagated in vitro for autologous transplant back into the same patient.

Additionally, vectors expressing the disclosed polynucleotides may be introduced into stem cells taken from the patient and clonally propagated in vitro for autologous transplant back into the same patient. Polypeptides and fusion proteins of the present invention may also, or alternatively, be used to generate binding agents, such as antibodies or fragments thereof, that are capable of detecting metastatic human lung tumors. Binding agents of the present invention may generally be prepared using methods known to those of ordinary skill in the art, including the representative procedures described herein. Binding agents are capable of differentiating between patients with and without lung cancer, using the representative assays described herein. In other words, antibodies or other binding agents raised against a lung tumor protein, or a suitable portion thereof, will generate a signal indicating the presence of primary or metastatic lung cancer in at least about 20% of patients afflicted with the disease, and will generate a negative signal indicating the absence of the disease in at least about 90% of individuals without primary or metastatic lung cancer. Suitable portions of such lung tumor proteins are portions that are able to generate a binding agent that indicates the presence of primary or metastatic lung cancer in substantially all (i.e., at least about 80%, and preferably at least about 90%) of the patients for which lung cancer would be indicated using the full length protein, and that indicate the absence of lung cancer in substantially all of those samples that would be negative when tested with full length protein. The representative assays described below, such as the two-antibody sandwich assay, may generally be employed for evaluating the ability of a binding agent to detect metastatic human lung tumors.

The ability of a polypeptide prepared as described herein to generate antibodies capable of detecting primary or metastatic human lung tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic lung cancer for the presence of a polypeptide that binds to the generated antibodies. Such test assays may be performed, for example, using a representative procedure described below. Polypeptides that generate antibodies capable of detecting at least 20% of primary or metastatic lung tumors by such procedures are considered to be useful in assays for detecting primary or metastatic human lung tumors. Polypeptide specific antibodies may be used alone or in combination to improve sensitivity.

Polypeptides capable of detecting primary or metastatic human lung tumors may be used as markers for diagnosing lung cancer or for monitoring disease progression in patients. In one embodiment, lung cancer in a patient may be diagnosed by evaluating a biological sample obtained from the patient for the level of one or more of the above polypeptides, relative to a predetermined cut-off value. As used herein, suitable "biological samples" include blood, sera, urine and/or lung secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof. Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with lung cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of lung cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without lung cancer. In general, a sample generating a signal that is three standard deviations above the predetermined cut-off value is considered positive for lung cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for lung cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of lung cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 μg and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of lung cancer. In this embodiment, assays as described above for the diagnosis of lung cancer may be performed over time, and the change in the level of reactive polypeptide(s) evaluated. For example, the assays may be performed every 24–72 hours for a period of 6 months to 1 year, and thereafter performed as needed. In general, lung cancer is progressing in those patients in whom the level of polypeptide detected by the binding agent increases over time. In contrast, lung cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate lung tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas exotoxin*, *Shigella toxin*, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise polynucleotide sequences encoding one or more of the above polypeptides, or one or more portions thereof. For example, at least two oligonucleotide primers may be employed in a polymerase chain reaction (PCR) based assay to amplify lung tumor-specific cDNA derived from a biological sample, wherein at least one of the oligonucleotide primers is specific for a polynucleotide molecule encoding a lung tumor protein of the present invention. The presence of the amplified cDNA is then detected using techniques well known in the art, such as gel electrophoresis. Similarly, oligonucleotide probes specific for a polynucleotide molecule encoding a lung tumor protein of the present invention may be used in a hybridization assay to detect the presence of an inventive polypeptide in a biological sample.

As used herein, the term "oligonucleotide primer/probe specific for a polynucleotide molecule" means an oligonucleotide sequence that has at least about 60%, preferably at least about 75% and more preferably at least about 90%, identity to the polynucleotide molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a polynucleotide molecule comprising sequence selected from SEQ ID NO: 1–109, 111, 113 115–151, 153, 154, 157, 158, 160, 162–164, 167, 168 and 171. Preferably, oligonucleotide probes for use in the inventive diagnostic methods comprise at least about 15 contiguous oligonucleotides of a polynucleotide molecule comprising a sequence provided in SEQ ID NO: 1–109,111, 113 115–151, 153, 154, 157, 158, 160, 162–164, 167, 168 and 171. Techniques for both PCR based assays and hybridization assays are well known in the art (see, for example, Mullis et al. Ibid; Ehrlich, Ibid). Primers or probes may thus be used to detect lung tumor-specific sequences in biological samples, including blood, semen, lung tissue and/or lung tumor tissue.

The following Examples are offered by way of illustration and not by way of limitation.

EXAMPLES

Example 1

Isolation and Characterization of cDNA Sequences Encoding Lung Tumor Polypeptides This example illustrates the isolation of cDNA molecules encoding lung tumor-specific polypeptides from lung tumor cDNA libraries.

A. Isolation of cDNA Sequences from a Lung Squamous Cell Carcinoma Library

A human lung squamous cell carcinoma cDNA expression library was constructed from poly $A^+$ RNA from a pool of two patient tissues using a Superscript Plasmid System for cDNA Synthesis and Plasmid Cloning kit (BRL Life Technologies, Gaithersburg, Md.) following the manufacturer's protocol. Specifically, lung carcinoma tissues were homogenized with polytron (Kinematica, Switzerland) and total RNA was extracted using Trizol reagent (BRL Life Technologies) as directed by the manufacturer. The poly $A^+$ RNA was then purified using an oligo dT cellulose column as described in Sambrook et al., *Molecular Cloning: A Laboratory Manual*, Cold Spring Harbor Laboratories, Cold Spring Harbor, N.Y., 1989. First-strand cDNA was synthesized using the NotI/Oligo-dT18 primer. Double-stranded cDNA was synthesized, ligated with BstXI/EcoRI adaptors (Invitrogen, San Diego, Calif.) and digested with NotI. Following size fractionation with cDNA size fractionation columns (BRL Life Technologies), the cDNA was ligated into the BstXI/NotI site of pcDNA3.1 (Invitrogen) and transformed into ElectroMax *E. coli* DH10B cells (BRL Life Technologies) by electroporation.

Using the same procedure, a normal human lung cDNA expression library was prepared from a pool of four tissue specimens. The cDNA libraries were characterized by determining the number of independent colonies, the percentage of clones that carried insert, the average insert size and by sequence analysis. The lung squamous cell carcinoma library contained $2.7 \times 10^6$ independent colonies, with 100% of clones having an insert and the average insert size being 2100 base pairs. The normal lung cDNA library contained $1.4 \times 10^6$ independent colonies, with 90% of clones having inserts and the average insert size being 1800 base pairs. For both libraries, sequence analysis showed that the majority of clones had a full length cDNA sequence and were synthesized from mRNA.

cDNA library subtraction was performed using the above lung squamous cell carcinoma and normal lung cDNA libraries, as described by Hara et al. (*Blood*, 84:189–199, 1994) with some modifications. Specifically, a lung squamous cell carcinoma-specific subtracted cDNA library was generated as follows. Normal tissue CDNA library (80 μg) was digested with BamHI and XhoI, followed by a filling-in reaction with DNA polymerase Klenow fragment. After phenol-chloroform extraction and ethanol precipitation, the DNA was dissolved in 133 μl of $H_2O$, heat-denatured and mixed with 133 μl (133 μg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (67 μl) was added and the biotinylation reaction was repeated. After extraction with butanol five times, the DNA was ethanol-precipitated and dissolved in 23 μl $H_2O$ to form the driver DNA.

To form the tracer DNA, 10 μg lung squamous cell carcinoma cDNA library was digested with NotI and SpeI, phenol chloroform extracted and passed through Chroma spin-400 columns (Clontech, Palo Alto, Calif.). Typically, 5 μg of cDNA was recovered after the sizing column. Following ethanol precipitation, the tracer DNA was dissolved in 5 μl $H_2O$. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl $H_2O$, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into NotI/SpeI site of chloramphenicol resistant pBCSK+ (Stratagene, La Jolla, Calif.) and transformed into ElectroMax E. coli DH10B cells by electroporation to generate a lung squamous cell carcinoma specific subtracted cDNA library (herein after referred to as "lung subtraction I").

A second lung squamous cell carcinoma specific subtracted cDNA library (referred to as "lung subtraction II") was generated in a similar way to the lung subtraction library I, except that eight frequently recovered genes from lung subtraction I were included in the driver DNA, and 24,000 independent clones were recovered.

To analyze the subtracted cDNA libraries, plasmid DNA was prepared from 320 independent clones, randomly picked from the subtracted lung squamous cell carcinoma specific libraries. Representative cDNA clones were further characterized by DNA sequencing with a Perkin Elmer/Applied Biosystems Division Automated Sequencer Model 373A and/or Model 377 (Foster City, Calif.). The cDNA sequences for sixty isolated clones are provided in SEQ ID NO: 1–60. These sequences were compared to known sequences in the gene bank using the EMBL and GenBank databases (release 96). No significant homologies were found to the sequences provided in SEQ ID NO: 2, 3, 19, 38 and 46. The sequences of SEQ ID NO: 1, 6–8, 10–13, 15, 17, 18, 20–27, 29, 30, 32, 34–37, 39–45, 47–49, 51, 52, 54, 55 and 57–59 were found to show some homology to previously identified expressed sequence tags (ESTs). The sequences of SEQ ID NO: 9, 28, 31 and 33 were found to show some homology to previously identified non-human gene sequences and the sequences of SEQ ID NO: 4, 5, 14, 50, 53, 56 and 60 were found to show some homology to gene sequences previously identified in humans.

The subtraction procedure described above was repeated using the above lung squamous cell carcinoma cDNA library as the tracer DNA, and the above normal lung tissue cDNA library and a cDNA library from normal liver and heart (constructed from a pool of one sample of each tissue as described above), plus twenty other cDNA clones that were frequently recovered in lung subtractions I and II, as the driver DNA (lung subtraction III). The normal liver and heart cDNA library contained $1.76×10^6$ independent colonies, with 100% of clones having inserts and the average insert size being 1600 base pairs. Ten additional clones were isolated (SEQ ID NO: 61–70). Comparison of these cDNA sequences with those in the gene bank as described above, revealed no significant homologies to the sequences provided in SEQ ID NO: 62 and 67. The sequences of SEQ ID NO: 61, 63–66, 68 and 69 were found to show some homology to previously isolated ESTs and the sequence provided in SEQ ID NO: 70 was found to show some homology to a previously identified rat gene.

B. Isolation of cDNA Sequences from a Lung Adenocarcinoma Library

A human lung adenocarcinoma cDNA expression library was constructed as described above. The library contained $3.2×10^6$ independent colonies, with 100% of clones having an insert and the average insert size being 1500 base pairs. Library subtraction was performed as described above using the normal lung and normal liver and heart cDNA expression libraries described above as the driver DNA. Twenty-six hundred independent clones were recovered.

Initial cDNA sequence analysis from 100 independent clones revealed many ribosomal protein genes. The cDNA sequences for fifteen clones isolated in this subtraction are provided in SEQ ID NO: 71–86. Comparison of these sequences with those in the gene bank as described above revealed no significant homologies to the sequence provided in SEQ ID NO: 84. The sequences of SEQ ID NO: 71, 73, 74, 77, 78 and 80–82 were found to show some homology to previously isolated ESTs, and the sequences of SEQ ID NO: 72, 75, 76, 79, 83 and 85 were found to show some homology to previously identified human genes.

Example 2

Determination of Tissue Specificity of Lung Tumor Polypeptides

Using gene specific primers, mRNA expression levels for seven representative lung tumor polypeptides described in Example 1 were examined in a variety of normal and tumor tissues using RT-PCR.

Briefly, total RNA was extracted from a variety of normal and tumor tissues using Trizol reagent as described above. First strand synthesis was carried out using 2 μg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. 1 μl of 1:30 dilution of cDNA was employed to enable the linear range amplification of the β-actin template and was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in five different types of tumor tissue (lung squamous cell carcinoma from 3 patients, lung adenocarcinoma, colon tumor from 2 patients, breast tumor and prostate tumor), and thirteen different normal tissues (lung from 4 donors, prostate, brain, kidney, liver, ovary, skeletal muscle, skin, small intestine, stomach, myocardium, retina and testes). Using a 10-fold amount of cDNA, the antigen LST-S1-90 (SEQ ID NO: 3) was found to be expressed at high levels in lung squamous cell carcinoma and in breast tumor, and at low to undetectable levels in the other tissues examined.

The antigen LST-S2-68 (SEQ ID NO: 15) appears to be specific to lung and breast tumor, however, expression was also detected in normal kidney. Antigens LST-S1-169 (SEQ ID NO: 6) and LST-S1-133 (SEQ ID NO: 5) appear to be very abundant in lung tissues (both normal and tumor), with the expression of these two genes being decreased in most of the normal tissues tested. Both LST-S1-169 and LST-S1-133 were also expressed in breast and colon tumors. Antigens LST-S1-6 (SEQ ID NO: 7) and LST-S2-I2-5F (SEQ ID NO: 47) did not show tumor or tissue specific expression, with the expression of LST-S1-28 being rare and only detectable in a few tissues. The antigen LST-S3-7 (SEQ ID NO: 63) showed lung and breast tumor specific expression, with its message only being detected in normal testes when the PCR was performed for 30 cycles. Lower level expression was detected in some normal tissues when the cycle number was increased to 35. Antigen LST-S3-13 (SEQ ID NO: 66) was found to be expressed in 3 out of 4 lung tumors, one breast tumor and both colon tumor samples. Its expression in normal tissues was lower compared to tumors, and was only detected in 1 out of 4 normal lung tissues and in normal tissues from kidney, ovary and retina. Expression of antigens LST-S3-4 (SEQ ID NO: 62) and LST-S3-14 (SEQ ID NO: 67) was rare and did not show any tissue or tumor specificity. Consistent with Northern blot analyses, the RT-PCT results on antigen LAT-S1-A-10A (SEQ ID NO: 78) suggested that its expression is high in lung, colon, stomach and small intestine tissues, including lung and colon tumors, whereas its expression was low or undetectable in other tissues.

A total of 2002 cDNA fragments isolated in lung subtractions I, II and III, described above, were colony PCR amplified and their mRNA expression levels in lung tumor, normal lung, and various other normal and tumor tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Seventeen non-redundant cDNA clones showed over-expression in lung squamous tumors, with expression in normal tissues tested (lung, skin, lymph node, colon, liver, pancreas, breast, heart, bone marrow, large intestine, kidney, stomach, brain, small intestine, bladder and salivary gland) being either undetectable, or 10-fold less compared to lung squamous tumors. The determined partial cDNA sequences for the clone L513S are provided in SEQ ID NO: 87 and 88; those for L514S are provided in SEQ ID NO: 89 and 90; those for L516S in SEQ ID NO: 91 and 92; that for L517S in SEQ ID NO: 93; that for L519S in SEQ ID NO: 94; those for L520S in SEQ ID NO: 95 and 96; those for L521S in SEQ ID NO: 97 and 98; that for L522S in SEQ ID NO: 99; that for L523S in SEQ ID NO: 100; that for L524S in SEQ ID NO: 101; that for L525S in SEQ ID NO: 102; that for L526S in SEQ ID NO: 103; that for L527S in SEQ ID NO: 104; that for L528S in SEQ ID NO: 105; that for L529S in SEQ ID NO: 106; and those for L530S in SEQ ID NO: 107 and 108. Additionally, the full-length cDNA sequences for L503S and L514S (variants 1 and 2), are provided in SEQ ID NO: 151, 153 and 154, respectively, with the corresponding predicted amino acid sequence being provided in SEQ ID NO: 152, 155 and 156. Due to polymorphisms, the clone L531 S appears to have two forms. A first determined full-length cDNA sequence for L531 S is provided in SEQ ID NO: 109, with the corresponding predicted amino acid sequence being provided in SEQ ID NO: 110. A second determined full-length cDNA sequence for L531S is provided in SEQ ID NO: 111, with the corresponding predicted amino acid sequence being provided in SEQ ID NO: 112. The sequence of SEQ ID NO: 111 is identical to that of SEQ ID NO: 109, except that it contains a 27 bp insertion. Similarly, L514S also has two alternatively spliced forms; the first variant cDNA is listed as SEQ ID NO: 153, with the corresponding amino acid sequence as SEQ ID NO: 155. The second variant form of L514S full-length cDNA is referred to as SEQ ID NO: 154, with its corresponding amino acid sequence as SEQ ID NO: 156.

Full length cloning for L524S (SEQ ID NO: 101) yielded two variants (SEQ ID NO: 163 and 164) with the corresponding predicted amino acid sequences (SEQ ID NO: 165 and 166), respectively. Both variants have been shown to encode parathyroid hormone-related peptide.

Comparison of the sequences of L514S and L531S (SEQ ID NO: 87 and 88, 89 and 90, and 109, respectively) with those in the gene bank, as described above, revealed no significant homologies to known sequences. The sequences of L513S, L516S, L517S, L519S, L520S and L530S (SEQ ID NO: 87 and 88, 91 and 92, 93, 94, 95 and 96, 107 and 108, respectively) were found to show some homology to previously identified ESTs. The sequences of L521S, L522S, L523S, L524S, L525S, L526S, L527S, L528S and L529S (SEQ ID NO: 97 and 98, 99, 99, 101, 102, 103, 104, 105, and 106, respectively) were found to represent known genes. The determined full-length cDNA sequences for L520S is provided in SEQ ID NO: 113, with the corresponding predicted amino acid sequence being provided in SEQ ID NO: 114. Subsequent microarray analysis has shown L520S to be overexpressed in breast tumors in addition to lung squamous tumors.

Further analysis has demonstrated L529S (SEQ ID NO: 106 and 115), L525S (SEQ ID NO: 102 and 120) and L527S (SEQ ID NO: 104) are cytosleletal components and potentially squamous cell specific proteins. L529S is connexin 26, a gap junction protein. It is highly expressed in lung squamous tumor 9688T, and moderately over-expressed in two others. However, lower level expression of connexin 26 is also detectable in normal skin, colon, liver and stomach. The over-expression of connexin 26 in some breast tumors has been reported and a mutated form of L529S may result in over-expression in lung tumors. L525S is plakophilin 1, a desmosomal protein found in plaque-bearing adhering junctions of the skin. Expression levels for L525S mRNA is highly elevated in three out of four lung squamous tumors tested, and in normal skin. L527S has been identified as keratin 6 isoform, type II 58 Kd keratin, and cytokeratin 13 and shows over-expression in squamous tumors and low expression in normal skin, breast and colon tissues. Notably, keratin and keratin-related genes have been extensively documented as potential markers for lung cancer including CYFRA2.1 (Pastor, A., et al, *Eur. Respir. J.,* 10:603–609, 1997). L513S (SEQ ID NO: 87 and 88) shows moderate over-expression in several tumor tissues tested, and encodes a protein that was first isolated as a pemphigus vulgaris antigen.

L520S (SEQ ID NO: 95 and 96) and L521S (SEQ ID NO: 97 and 98) are highly expressed in lung squamous tumors, and L520S is up-regulated in normal salivary gland and L521 S is over-expressed in normal skin. Both belong to a family of small proline rich proteins and represent markers for fully differentiated squamous cells. L521S has been described as a specific marker for lung squamous tumor (Hu, R., et al, *Lung Cancer,* 20:25–30, 1998). L515S (SEQ ID NO: 162) encodes IGF-β2 and L516S is an aldose reductase homologue and both are moderately expressed in lung squamous tumors and in normal colon. Notably, L516S (SEQ ID NO: 91 and 92) is up-regulated in metastatic tumors but not primary lung adenocarcinoma, an indication of its potential role in metastasis and a potential prognostic marker. L522S (SEQ ID NO: 99) is moderately overexpressed in lung squamous tumors with minimum expression in normal tissues. L522S has been shown to belong to a class IV alcohol dehydrogenase, ADH7, and its expression profile suggests it is a squamous cell specific antigen. L523S (SEQ ID NO: 100) is moderately over-expressed in lung squamous tumor, human pancreatic cancer cell lines and pancreatic cancer tissues, suggesting this gene may be a shared antigen between pancreatic and lung squamous cell cancer.

L524S (SEQ ID NO: 101) is over-expressed in the majority of squamous tumors tested and is homolgous with parathyroid hormone-related peptide (PTHrP), which is best known to cause humoral hypercalcaemia associated with malignant tumors such as leukemia, prostate and breast cancer. It is also believed that PTHrP is most commonly associated with squamous carcinoma of lung and rarely with lung adenocarcinoma (Davidson, L. A., et al, *J. Pathol.*, 178: 398–401, 1996). L528S (SEQ ID NO: 105) is highly over-expressed in two lung squamous tumors with moderate expression in two other squamous tumors, one lung adenocarcinoma and some normal tissues, including skin, lymph nodes, heart, stomach and lung. It encodes the NMB gene that is similar to the precursor of melanocyte specific gene Pmel17, wfhich is reported to be preferentially expressed in low-metastatic potential melanoma cell lines. This suggests that L528S may be a shared antigen in both melanoma and lung aquamous cell carcinoma. L526S (SEQ ID NO: 103) is overexpressed in all lung squamous cell tumor tissues tested and has been shown to share homology with a gene (ATM) in which a mutation causes ataxia telangiectasia, a genetic disorder in humans causing a predisposition to cancer, among other symptoms. ATM encodes a protein that activates p53 mediated cell-cycle checkpoint through direct binding and phosphorylation of the p53 molecule. Approximately 40% of lung cancer is associated with p53 mutations, and it is speculated that over-expression of ATM is a result of compensation for loss of p53 function, but it is unknown whether over-expression is the cause of result of lung squamous cell carcinoma. Additionally, expression of L526S (ATM) is also detected in a metastatic but not lung adenocarcinoma, suggesting a role in metastasis.

Example 3
Isolation and Characterization of Lung Tumor Polypeptides by PCR-Based Subtraction Eight hundred and fifty seven clones from a cDNA subtraction library, containing cDNA from a pool of two human lung squamous tumors subtracted against eight normal human tissue cDNAs including lung, PBMC, brain, heart, kidney, liver, pancreas, and skin, (Clontech, Palo Alto, Calif.) were derived and submitted to a first round of PCR amplification. This library was subjected to a second round of PCR amplification, following the manufacturer's protocol. The resulting cDNA fragments were subcloned into the vector P7-Adv vector (Clontech, Palo Alto, Calif.) and transformed into DH5α *E. coli* (Gibco, BRL). DNA was isolated from independent clones and sequenced using a Perkin Elmer/Applied Biosystems Division Automated Sequencer Model 373A.

One hundred and sixty two positive clones were sequenced. Comparison of the DNA sequences of these clones with those in the gene bank using the EMBL and GenBank databases, as described above, revealed no significant homologies to 13 of these clones, hereinafter referred to as Contig 13, 16, 17, 19, 22, 24, 29, 47, 49, 56–59. The determined cDNA sequences for these clones are provided in SEQ ID NO: 125, 127–129, 131–133, 142, 144, 148–150, and 157, respectively. Contigs 1, 3–5, 7–10, 12, 11, 15, 20, 31, 33, 38, 39, 41, 43, 44, 45, 48, 50, 53, 54 (SEQ ID NO: 115–124, 126, 130, 134–141, 143, 145–147, respectively) were found to show some degree of homology to previously identified DNA sequences. Contig 57 (SEQ ID NO: 149) was found to represent the clone L519S (SEQ ID NO: 94) disclosed in U.S. patent application Ser. No. 09/123,912, filed Jul. 27, 1998. To the best of the inventors' knowledge, none of these sequences have been previously shown to be differentially over-expressed in lung tumors.

mRNA expression levels for representative clones in lung tumor tissues, normal lung tissues (n=4), resting PBMC, salivary gland, heart, stomach, lymph nodes, skeletal muscle, soft palate, small intestine, large intestine, bronchial, bladder, tonsil, kidney, esophagus, bone marrow, colon, adrenal gland, pancreas, and skin, (all derived from human) were determined by RT-PCR as described above. Expression levels using microarray technology, as described above, were examined in one sample of each tissue type unless otherwise indicated.

Contig 3 (SEQ ID NO: 116) was found to be highly expressed in all head and neck squamous cell tumors tested (17/17), and expressed in the majority (8/12) of lung squamous tumors, (high expression in 7/12, moderate in 2/12, and low in 2/12), while showing negative expression for 2/4 normal lung tissues and low expression in the remaining two samples. Contig 3 showed moderate expression in skin and soft palate, and lowered expression levels in resting PBMC, large intestine, salivary gland, tonsil, pancreas, esophagus, and colon. Contig 11 (SEQ ID NO: 124) was found to be expressed in all head and neck squamous cell tumors tested (17/17): highly expressed in 14/17, and moderately expressed in 3/17. Additionally, expression in lung squamous tumors showed high expression in 3/12 and moderate in 4/12. Contig 11 was negative for 3/4 normal lung samples, with the remaining sample having only low expression. Contig 11 showed low to moderate reactivity to salivary gland, soft palate, bladder, tonsil, skin, esophagus, and large intestine. Contig 13 (SEQ ID NO: 125) was found to be expressed in all head and neck squamous cell tumors tested (17/17): highly expressed in 12/17, and moderately expressed in 5/17. Contig 13 was expressed in 7/12 lung squamous tumors, with high expression in 4/12 and moderate expression in three samples. Analysis of normal lung samples showed negative expression for 2/4 and low to moderate expression in the remaining two samples. Contig 13 did show low to moderate reactivity to resting PBMC, salivary gland, bladder, pancreas, tonsil, skin, esophagus, and large intestine, as well as high expression in soft palate. Contig 16 (SEQ ID NO: 127) was found to be moderately expressed in some head and neck squamous cell tumors (6/17) and one lung squamous tumor; while showing no expression in any normal lung samples tested. Contig 16 did show low reactivity to resting PBMC, large intestine, skin, salivary gland, and soft palate. Contig 17 (SEQ ID NO: 128) was shown to be expressed in all head and neck squamous cell tumors tested (17/17): highly expressed in 5/17, and moderately expressed in 12/17. Expression levels in lung squamous tumors showed one tumor sample with high expression and 3/12 with moderate levels. Contig 17 was negative for 2/4 normal lung samples, with the remaining samples having only low expression. Additionally, low level expression was found in esophagus and soft palate. Contig 19 (SEQ ID NO: 129) was found to be expressed in most head and neck squamous cell tumors tested (11/17): with two samples having high levels, 6/17 showing moderate expression, and low expression being found in 3/17. Testing in lung squamous tumors revealed only moderate expression in 3/12 samples. Expression levels in 2/4 of normal lung samples were negative, the two other samples having only low expression. Contig 19 did show low expression levels in esophagus, resting PBMC, salivary gland, bladder, soft palate and pancreas.

Contig 22, (SEQ ID NO: 131) was shown to be expressed in most head and neck squamous cell tumors tested (13/17) with high expression in four of these samples, moderate expression in 6/17, and low expression in 3/17. Expression levels in lung squamous tumors were found to be moderate to high for 3/12 tissues tested, with negative expression in two normal lung samples and low expression in two other samples (n=4). Contig 22 did show low expression in skin, salivary gland and soft palate. Similarly, Contig 24 (SEQ ID NO: 132) was found to be expressed in most head and neck squamous cell tumors tested (13/17) with high expression in three of these samples, moderate expression in 6/17, and low expression in 4/17. Expression levels in lung squamous tumors were found to be moderate to high for 3/12 tissues tested, with negative expression for three normal lung samples and low expression in one sample (n=4). Contig 24 did show low expression in skin, salivary gland and soft palate. Contig 29 (SEQ ID NO: 133) was expressed in nearly all head and neck squamous cell tumors tested (16/17): highly expressed in 4/17, moderately expressed in 11/17, with low expression in one sample. Also, it was moderately expressed in 3/12 lung squamous tumors, while being negative for 2/4 normal lung samples. Contig 29 showed low to moderate expression in large intestine, skin, salivary gland, pancreas, tonsil, heart and soft palate. Contig 47 (SEQ ID NO: 142) was expressed in most head and neck squamous cell tumors tested (12/17): moderate expression in 10/17, and low expression in two samples. In lung squamous tumors, it was highly expressed in one sample and moderately expressed in two others (n=13). Contig 47 was negative for 2/4 normal lung samples, with the remaining two samples having moderate expression. Also, Contig 47 showed moderate expression in large intestine, and pancreas, and low expression in skin, salivary gland, soft palate, stomach, bladder, resting PBMC, and tonsil.

Contig 48 (SEQ ID NO: 143) was expressed in all head and neck squamous cell tumors tested (17/17): highly expressed in 8/17 and moderately expressed in 7/17, with low expression in two samples. Expression levels in lung squamous tumors were high to moderate in three samples (n=13). Contig 48 was negative for one out of four normal lung samples, the remaining showing low or moderate expression. Contig 48 showed moderate expression in soft palate, large intestine, pancreas, and bladder, and low expression in esophagus, salivary gland, resting PBMC, and heart. Contig 49 (SEQ ID NO: 144) was expressed at low to moderate levels in 6/17 head and neck squamous cell tumors tested. Expression levels in lung squamous tumors were moderate in three samples (n=13). Contig 49 was negative for 2/4 normal lung samples, the remaining samples showing low expression. Moderate expression levels in skin, salivary gland, large intestine, pancreas, bladder and resting PBMC were shown, as well as low expression in soft palate, lymph nodes, and tonsil. Contig 56 (SEQ ID NO: 148) was expressed in low to moderate levels in 3/17 head and neck squamous cell tumors tested, and in lung squamous tumors, showing low to moderate levels in three out of thirteen samples. Notably, low expression levels were detected in one adenocarcinoma lung tumor sample (n=2). Contig 56 was negative for 3/4 normal lung samples, and showed moderate expression levels in only large intestine, and low expression in salivary gland, soft palate, pancreas, bladder, and resting PBMC. Contig 58, also known as L769P, (SEQ ID NO: 150) was expressed at moderate levels in 11/17 head and neck squamous cell tumors tested and low expression in one additional sample. Expression in lung squamous tumors showed low to moderate levels in three out of thirteen samples. Contig 58 was negative for 3/4 normal lung samples, with one sample having low expression. Moderate expression levels in skin, large intestine, and resting PBMC were demonstrated, as well as low expression in salivary gland, soft palate, pancreas, and bladder. Contig 59 (SEQ ID NO: 157) was expressed in some head, neck, and lung squamous tumors. Low level expression of Contig 59 was also detected in salivary gland and large intestine.

Additionally, the full-length cDNA sequence for Contigs 22, referred to as L763P, is provided in SEQ ID NO: 158, with the corresponding predicted amino acid sequence being provided in SEQ ID NO: 159. Also, the full-length cDNA sequence incorporating Contigs 17, 19, and 24, referred to as L762P, is provided in SEQ ID NO: 160, with the corresponding predicted amino acid sequence being provided in SEQ ID NO: 161. Further analysis of L762P has determined it to be a type I membrane protein and two additional variants have been sequenced. Variant 1 (SEQ ID NO: 167 and the corresponding amino acid sequence in SEQ ID NO: 169) is an alternatively spliced form of SEQ ID NO: 160 resulting in deletion of 503 nucleotides, as well as deletion of a short segment of the expressed protein. Variant 2 (SEQ ID NO: 168 and the corresponding amino acid sequence in SEQ ID NO: 170) has a two nucleotide deletion at the 3' coding region in comparison to SEQ ID NO: 160, resulting in a secreted form of the expressed protein.

The full-length cDNA sequence for contig 56 (SEQ ID NO: 148), referred to as L773P, is provided in SEQ ID NO: 171, with the predicted amino acid sequence in SEQ ID NO: 172. Subsequent Northern blot analysis of L773P demonstrates this transcript is differentially over-expressed in squamous tumors and detected at approximately 1.6 Kb in primary lung tumor tissue and approximately 1.3 Kb in primary head and neck tumor tissue.

Subsequent microarray analysis has shown Contig 58, also referred to as L769S (SEQ ID NO: 150), to be over-expressed in breast tumors in addition to lung squamous tumors.

Example 4

Synthesis of Polypeptides

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated polypeptide comprising the amino acid sequence of SEQ ID NO:155.

2. A composition comprising a polypeptide of claim 1 and a physiologically acceptable carrier.

3. A composition comprising a polypeptide of claim 1, and a non-specific immune response enhancer.

4. The composition of claim 3 wherein the non-specific immune response enhancer is an adjuvant.

* * * * *

SEQUENCE LISTING

<160> NUMBER OF SEQ ID NOS: 172

<210> SEQ ID NO 1
<211> LENGTH: 315
<212> TYPE: DNA
<213> ORGANISM: Homo sapien
<220> FEATURE:
<221> NAME/KEY: misc_feature
<222> LOCATION: (1)...(315)
<223> OTHER INFORMATION: n = A,T,C or G

<400> SEQUENCE: 1

| | | |
|---|---|---|
| gcagagacag actggtggtt gaacctggag gtgccaaaaa agccagctgc gggcccagga | 60 |
| cagctgccgt gagactcccg atgtcacagg cagtctgtgt ggttacagcg cccctcagtg | 120 |
| ttcatctcca gcagagacaa cggaggaggc tcccaccagg acggttctca ttatttatat | 180 |
| gttaatatgt ttgtaaactc atgtacagtt ttttttgggg gggaagcaat gggaanggta | 240 |
| naaattacaa atagaatcat ttgctgtaat ccttaaatgg caaacggtca ggccacgtga | 300 |
| aaaaaaaaaa aaaaa | 315 |

<210> SEQ ID NO 2
<211> LENGTH: 380
<212> TYPE: DNA
<213> ORGANISM: Homo sapien

<400> SEQUENCE: 2

| | | |
|---|---|---|
| atttaggctt aagatttttgt ttacccttgt tactaaggag caaattagta ttaaagtata | 60 |
| atatatataa acaaatacaa aaagttttga gtggttcagc ttttttatttt tttttaatgg | 120 |
| cataactttt aacaacactg ctctgtaatg ggttgaactg tggtactcag actgagataa | 180 |
| ctgaaatgag tggatgtata gtgttattgc ataattatcc cactatgaag caaagggact | 240 |
| ggataaattc ccagtctaga ttattagcct ttgttaacca tcaagcacct agaagaagaa | 300 |
| ttattggaaa ttttgtcctc tgtaactggc actttgggt gtgacttatc ttttgccttt | 360 |
| gtaaaaaaaa aaaaaaaaaa | 380 |

<210> SEQ ID NO 3
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 3

| | | |
|---|---|---|
| ttgtaagtat acaattttag aaaggattaa atgttattga tcattttact gaatactgca | 60 |
| catcctcacc atacaccatc cactttccaa taacatttaa tcctttctaa aattgtaagt | 120 |
| atacaattgt actttctttg gattttcata acaaatatac catagactgt taattttatt | 180 |
| gaagtttcct taatggaatg agtcattttt gtcttgtgct tttgaggtta cctttgcttt | 240 |
| gacttccaac aatttgatca tatagtgttg agctgtggaa atctttaagt ttattctata | 300 |
| gcaataattt ctattnnnag annccnggnn naaaannann annaaa | 346 |

<210> SEQ ID NO 4
<211> LENGTH: 372
<212> TYPE: DNA
<213> ORGANISM: Homo sapien

```
<220> FEATURE:
<221> NAME/KEY: misc_feature
<222> LOCATION: (1)...(372)
<223> OTHER INFORMATION: n = A,T,C or G

<400> SEQUENCE: 4
actagtctca ttactccaga attatgctct tgtacctgtg tggctgggtt tcttagtcgt    60
tggtttggtt tggttttttg aactggtatg tagggtggtt cacagttcta atgtaagcac   120
tctcttctcc aagttgtgct tgtggggac aatcattctt tgaacattag agaggaaggc   180
agttcaagct gttgaaaaga ctattgctta ttttttgtttt taaagaccta cttgacgtca   240
tgtggacagt gcacgtgcct tacgctacat cttgttttct aggaagaagg ggatgcnggg   300
aaggantggg tgctttgtga tggataaaac gnctaaataa cacacccttta cattttgaaa   360 aaaacaaaac aa                                                       372

<210> SEQ ID NO 5
<211> LENGTH: 698
<212> TYPE: DNA
<213> ORGANISM: Homo sapien
<220> FEATURE:
<221> NAME/KEY: misc_feature
<222> LOCATION: (1)...(698)
<223> OTHER INFORMATION: n = A,T,C or G

<400> SEQUENCE: 5
actagtanga tagaaacact gtgtcccgag agtaaggaga gaagctacta ttgattagag    60
cctaacccag gttaactgca agaagaggcg ggatactttc agctttccat gtaactgtat   120
gcataaagcc aatgtagtcc agtttctaag atcatgttcc aagctaactg aatcccactt   180
caatacacac tcatgaactc ctgatggaac aataacaggc ccaagcctgt ggtatgatgt   240
gcacacttgc tagactcaga aaaatactac ctctcataaa tgggtgggag tattttgggt   300
gacaacctac tttgcttggc tgagtgaagg aatgatattc atatnttcat ttattccatg   360
gacatttagt tagtgctttt tatataccag gcatgatgct gagtgacact cttgtgtata   420
tntccaaatn ttngtncngt cgctgcacat atctgaaatc ctatattaag antttcccaa   480
natgangtcc ctggtttttc cacgccactt gatcngtcaa ngatctcacc tctgtntgtc   540
ctaaaaccnt ctnctnnang gttagacngg acctctcttc tcccttcccg aanaataag   600 tgtgngaaga nanccncncn cccccctncn tncnncctng ccngctnnnc cncntgtngg   660
gggngccgcc cccgcggggg gaccccccn ttttcccc                            698

<210> SEQ ID NO 6
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 6
actagtcaaa aatgctaaaa taatttggga gaaaatattt tttaagtagt gttatagttt    60
catgtttatc ttttattatg tnttgtgaag ttgtgtcttt tcactaatta cctatactat   120
gccaatattt ccttatatct atccataaca tttatactac atttgtaaga gaatatgcac   180
gtgaaactta acactttata aggtaaaaat gaggtttcca agatttaata atctgatcaa   240
gttcttgtta tttccaaata gaatggactt ggtctgttaa ggggctaagg gagaagaaga   300
```

-continued

```
agataaggtt aaaagttgtt aatgaccaaa cattctaaaa gaaatgcaaa aaaaaattta    360
ttttcaagcc ttcgaactat ttaaggaaag caaaatcatt tcctanatgc atatcatttg    420
tgagantttc tcantaatat cctgaatcat tcatttcagc tnaggcttca tgttgactcg    480

atatgtcatc tagggaaagt ctatttcatg gtccaaacct gttgccatag ttggtnaggc    540
tttcctttaa ntgtgaanta ttnacangaa attttctctt tnanagttct tnatagggtt    600
aggggtgtgg gaaaagcttc taacaatctg tagtgttncg tgttatctgt ncagaaccan    660
aatnacggat cgnangaagg actgggtcta tttacangaa cgaatnatct ngttnnntgt    720
gtnnncaact ccngggagcc                                                740
```

```
<210> SEQ ID NO 7
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 7
gctggggagc tcggcatggc ggtccccgct gcagccatgg ggccctcggc gttgggccag     60
agcggccccg gctcgatggc cccgtggtgc tcagtgagca gcggcccgtc gcgctacgtg    120
cttgggatgc aggagctgtt ccggggccac agcaagaccg cgagttcctg gcgcacagcg    180
ccaaggtgca ctcggtggcc tggagttgcg acgggcgtcg cctacctcgg ggtcttcgac    240
aagacgccac gtcttcttgc tgganaanga ccgttggtca aagaaaacaa ttatcgggga    300
catggggata gtgtggacca ctttgttggc atccaagtaa tcctgaccta tttgttacgg    360
cgtctggaga taaaaccatt cgcatctggg atgtgaggac tacaaaatgc attgccactg    420
tgaacactaa aggggagaac attaatatct gctggantcc tgatgggcan accattgctg    480
tagcnacaag gatgatgtgg tgactttatt gatgccaaga aaccccgttc caaagcaaaa    540
aaacanttcc aanttcgaag tcaccnaaat ctcctggaac aatgaacatn aatatnttct    600
tcctgacaat ggnccttggg tgtntcacat cctcagctnc cccaaaactg aancctgtnc    660
natccacccc                                                           670
```

```

<210> SEQ ID NO 8
<211> LENGTH: 689
<212> TYPE: DNA
<213> ORGANISM: Homo sapien
<220> FEATURE:
<221> NAME/KEY: misc_feature
<222> LOCATION: (1)...(689)
<223> OTHER INFORMATION: n = A,T,C or G

<400> SEQUENCE: 8
actagtatct aggaatgaac agtaaaagag gagcagttgg ctacttgatt acaacagagt     60
aaatgaagta ctggatttgg gaaaacctgg ttttattaga acatatggaa tgaaagccta    120
cacctagcat tgcctactta gccccctgaa ttaacagagc ccaattgaga caaacccctg    180
gcaacaggaa attcaaggga gaaaaagtaa gcaacttggg ctaggatgag ctgactccct    240
tagagcaaag ganagacagc ccccattacc aaataccatt tttgcctggg gcttgtgcag    300
ctggcagtgt tcctgcccca gcatggcacc ttatngtttt gatagcaact tcgttgaatt    360
ttcaccaact tattacttga aattataata tagcctgtcc gtttgctgtn tccaggctgt    420
gatatatntt cctagtggtt tgactttnaa aataaatnag gtttantttt ctccccccnn    480
```

```
cnntnctncc nntcnctcnn cnntccccc cnctcngtcc tccnnnnttn ggggggggccn      540 ccccncggn ggaccccct ttggtccctt agtggaggtt natggcccct ggnnttatcc        600
nggccntann tttccccgtn nnaaatgntt ccccctccca ntcccnccac ctcaanccgg      660
aagcctaagt ttntaccctg ggggtcccc                                       689

<210> SEQ ID NO 9
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 9
gtccactctc ctttgagtgt actgtcttac tgtgcactct gttttcaac tttctagata       60 taaaaaatgc ttgttctata gtggagtaag agctcacaca cccaaggcag caagataact     120
gaaaaaagcg aggcttttt gccaccttgg taaaggccag ttcactgcta tagaactgct      180
ataagcctga agggaagtag ctatgagact ttccattttt cttagttctc ccaataggct     240
ccttcatgga aaaggcttc ctgtaataat tttcacctaa tgaattagca gtgtgattat      300
ttctgaaata agagacaaat tgggccgcag agtcttcctg tgatttaaaa taaacaaccc    360
aaagttttgt ttggtcttca ccaaaggaca tactctaggg ggtatgttgt tgaagacatt     420 caaaacatt agctgttctg tctttcaatt tcaagttatt ttggagactg cctccatgtg      480
agttaattac tttgctctgg aactagcatt attgtcatta tcatcacatt ctgtcatcat    540
catctgaata atattgtgga tttcccctc tgcttgcatc ttcttttgac tcctctggga     600
anaaatgtca aaaaaaagg tcgatctact cngcaaggnc catctaatca ctgcgctgga    660
aggacccnct gccc                                                      674

<210> SEQ ID NO 10
<211> LENGTH: 346
<212> TYPE: DNA
<213> ORGANISM: Homo sapien
<220> FEATURE:
<221> NAME/KEY: misc_feature
<222> LOCATION: (1)...(346)
<223> OTHER INFORMATION: n = A,T,C or G

<400> SEQUENCE: 10
actagtctgc tgatagaaag cactatacat cctattgttt ctttctttcc aaaatcagcc      60
ttctgtctgt aacaaaaatg tactttatag agatggagga aaaggtctaa tactacatag    120
ccttaagtgt ttctgtcatt gttcaagtgt attttctgta acagaaacat atttggaatg    180
tttttctttt cccttataa attgtaattc ctgaaatact gctgcttaa aaagtcccac      240 tgtcagatta tattatctaa caattgaata ttgtaaatat acttgtctta cctctcaata    300
aaagggtact tttctattan nnagnngnnn gnnnnataaa anaaaa                   346

<210> SEQ ID NO 11
<211> LENGTH: 602
<212> TYPE: DNA
<213> ORGANISM: Homo sapien

<400> SEQUENCE: 11
actagtaaaa agcagcattg ccaaataatc cctaattttc cactaaaaat ataatgaaat      60
```

```
gatgttaagc ttttttgaaaa gtttaggtta aacctactgt tgttagatta atgtatttgt    120
tgcttcccct tatctggaat gtggcattag cttttttatt ttaaccctct ttaattctta    180
ttcaattcca tgacttaagg ttggagagct aaacactggg attttttggat aacagactga    240 cagttttgca taattataat cggcattgta catagaaagg atatggctac cttttgttaa    300
atctgcactt tctaaatatc aaaaaaggga atgaagtta taaatcaatt tttgtataat    360
ctgtttgaaa catgagtttt atttgcttaa tattagggct ttgccccttt tctgtaagtc    420
tcttgggatc ctgtgtagaa ctgttctcat taaacaccaa acagttaagt ccattctctg    480
gtactagcta caaattcgt ttcatattct acttaacaat ttaaataaac tgaaatattt    540
ctagatggtc tacttctgtt catataaaaa caaaacttga tttccaaaaa aaaaaaaaaa    600
aa    602
```

<210> SEQ ID NO 12
<211> LENGTH: 685
<212> TYPE: DNA
<213> ORGANISM: Homo sapien
<220> FEATURE:
<221> NAME/KEY: misc_feature
<222> LOCATION: (1)...(685)
<223> OTHER INFORMATION: n = A,T,C or G

<400> SEQUENCE: 12

```
actagtcctg tgaaagtaca actgaaggca gaaagtgtta ggattttgca tctaatgttc    60
attatcatgg tattgatgga cctaagaaaa taaaaattag actaagcccc caaataagct    120
gcatgcattt gtaacatgat tagtagattt gaatatatag atgtagtatn ttgggtatct    180
aggtgtttta tcattatgta aaggaattaa agtaaaggac tttgtagttg ttttattaa    240 atatgcatat agtagagtgc aaaaatatag caaaaatana aactaaaggt agaaaagcat    300
tttagatatg ccttaatnta nnaactgtgc caggtggccc tcggaataga tgccaggcag    360
agaccagtgc ctgggtggtg cctccccttg tctgcccccc tgaagaactt ccctcacgtg    420
angtagtgcc ctcgtaggtg tcacgtggan tantgggganc aggccgnncn gtnanaagaa    480
ancanngtga nagtttcncc gtngangcng aactgtccct gngccnnnac gctcccanaa    540
cntntccaat ngacaatcga gtttccnnnc tccngnaacc tngccgnnnn cnngccnnc    600 cantntgnta accccgcgcc cggatcgctc tcnnntcgtt ctcncncnaa ngggntttcn    660
cnnccgccgt cncnncccccg cnncc    685
```

<210> SEQ ID NO 13
<211> LENGTH: 694
<212> TYPE: DNA
<213> ORGANISM: Homo sapien
<220> FEATURE:
<221> NAME/KEY: misc_feature
<222> LOCATION: (1)...(694)
<223> OTHER INFORMATION: n = A,T,C or G

<400> SEQUENCE: 13

```
cactagtcac tcattagcgt tttcaatagg gctcttaagt ccagtagatt acgggtagtc    60
agttgacgaa gatctggttt acaagaacta attaaatgtt tcattgcatt tttgtaagaa    120
cagaataatt ttataaaatg tttgtagttt ataattgccg aaaataattt aaagacactt    180
tttctctgtg tgtgcaaatg tgtgtttgtg atccattttt ttttttttttt taggacacct    240 gtttactagc tagctttaca atatgccaaa aaaggatttc tccctgaccc catccgtggt    300
tcaccctctt ttccccccat gcttttttgcc ctagtttata acaaaggaat gatgatgatt    360
```

```
taaaaagtag ttctgtatct tcagtatctt ggtcttccag aaccctctgg ttgggaaggg      420
gatcattttt tactggtcat ttccctttgg agtgtactac tttaacagat ggaaagaact      480
cattggccat ggaaacagcc gangtgttgg gagccagcag tgcatggcac cgtccggcat      540
ctggcntgat tggtctggct gccgtcattg tcagcacagt gccatgggac atggggaana      600
ctgactgcac ngccaatggt tttcatgaag aatacngcat ncncngtgat cacgtnancc      660
angacgctat gggggncana gggccanttg cttc                                 694

<210> SEQ ID NO 14
<211> LENGTH: 679
<212> TYPE: DNA
<213> ORGANISM: Homo sapien
<220> FEATURE:
<221> NAME/KEY: misc_feature
<222> LOCATION: (1)...(679)
<223> OTHER INFORMATION: n = A,T,C or G

<400> SEQUENCE: 14
cagccgcctg catctgtatc cagcgccang tcccgccagt cccagctgcg cgcgccccc       60 agtcccgnac ccgttcggcc cangctnagt tagncctcac catnccggtc aaaggangca     120
ccaagtgcat caaatacctg cngtncggat ntaaattcat cttctggctt gccgggattg     180
ctgtccntgc cattggacta nggctccgat ncgactctca gaccnganc atcttcganc      240 naganactaa tnatnattnt tccagcttct acacaggagt ctatattctg atcggatccg     300
gcnccctcnt gatgctggtg ggcttcctga gctgctgcgg ggctgtgcaa gagtcccant     360
gcatgctggg actgttcttc ggcttcntct tggtgatatn cgccattgaa atacctgcgg     420
ccatctgggg atattccact ncgatnatgt gattaaggaa ntccacggag ttttacaagg     480
acacgtacaa cnacctgaaa accnnggatg ancccaccg ggaancnctg aangccatcc      540
actatgcgtt gaactgcaat ggtttggctg gggncttga acaatttaat cncatacatc      600
tggccccann aaaggacntn ctcganncct tcnccgtgna attcngttct gatnccatca     660
cagaagtctc gaacaatcc                                                  679

<210> SEQ ID NO 15
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 15
actagtggat aaaggccagg gatgctgctc aacctcctac catgtacagg gacgtctccc       60 cattcaact acccaatccg aagtgtcaac tgtgtcagga ctaanaaacc ctggttttga      120
ttaaaaaagg gcctgaaaaa aggggagcca caaatctgtc tgcttcctca cnttantcnt      180
tggcaaatna gcattctgtc tcnttggctg cngcctcanc ncaaaaaanc ngaactcnat     240
cnggcccagg aatacatctc ncaatnaacn aaattganca aggcnntggg aaatgccnga     300
tgggattatc ntccgcttgt tganctttcta agtttcnttc ccttcattcn accctgccag    360
ccnagttctg ttagaaaaat gccngaattc naacnccggt tttcntactc ngaatttaga    420
tctncanaaa cttcctggcc acnattcnaa ttnanggnca cgnacanatn ccttccatna    480
ancncacccc acntttgana gccangacaa tgactgcntn aantgaaggc ntgaaggaan    540
```

```
aactttgaaa ggaaaaaaaa ctttgtttcc ggccccttcc aacncttctg tgttnancac      600
tgccttctng naaccctgga agcccngnga cagtgttaca tgttgttcta nnaaacngac      660
ncttnaatnt cnatcttccc nanaacgatt ncncc                                 695
```

<210> SEQ ID NO 16
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G

<400> SEQUENCE: 16

```
cgccgaagca gcagcgcagg ttgtccccgt ttccctccc ccttcccttc tccggttgcc       60
ttcccgggcc ccttacactc cacagtcccg gtcccgccat gtcccagaaa caagaagaag     120
agaaccctgc ggaggagacc ggcgaggaga agcaggacac gcaggagaaa gaaggtattc     180
tgcctgagag agctgaagag gcaaagctaa aggccaaata cccaagccta ggacaaaagc     240
ctggaggctc cgacttcctc atgaagagac tccagaaagg gcaaaagtac tttgactcng     300
gagactacaa catggccaaa gccaacatga agaataagca gctgccaagt gcangaccag     360
acaagaacct ggtgactggt gatcacatcc cacccaca ggatctgccc agagaaagtc       420
ctcgctcgtc accagcaagc ttgcgggtgg ccaagttgaa tgatgctgcc ggggctctgc     480
canatctgag acgcttccct ccctgcccca cccgggtcct gtgctggctc ctgcccttcc     540
tgcttttgca gccangggtc aggaagtggc ncggtngtg gctggaaagc aaaacccttt      600
cctgttggtg tcccacccat ggagccctg gggcgagccc angaacttga nccttttgt      660 tntcttncc                                                              669
```

<210> SEQ ID NO 17
<211> LENGTH: 697
<212> TYPE: DNA
<213> ORGANISM: Homo sapien
<220> FEATURE:
<221> NAME/KEY: misc_feature
<222> LOCATION: (1)...(697)
<223> OTHER INFORMATION: n = A,T,C or G

<400> SEQUENCE: 17

```
gcaagatatg gacaactaag tgagaaggta atnctctact gctctagntn ctccnggcnn      60
gacgcgctga ggagannnac gctggcccan ctgccggcca cacacgggga tctggtnat     120 gcctgcccan gggancccca ncnctcggan cccatntcac accgnnccn tncgcccacn     180 ncctggctcn cncngcccng ccagctcnc gnccccctcc gccnnnctcn ttnncntctc      240
cncnccctcc ncnacnacct cctacccncg gctccctccc cagccccccc ccgcaancct     300
ccacnacncc ntcnncncga ancnccctc gcnctcngcc ccngccccct gcccccgcc       360 cncnacnncg cgntccccg cgcncgcngc ctcnccccct cccacnacag ncncacccgc      420
agncacgcnc tccgcccnct gacgccccnn cccgccgcgc tcaccttcat ggnccnacng    480
ccccgctcnc nccnctgcnc gccgncnngg cgcccgccc cnncgngtn ccncncgnng      540 ccccngcngn angcngtgcg cnncangncc gngccgnncn ncaccctccg nccnccgccc    600
cgcccgctgg gggctcccgc cncgcggntc antcccccnc cntngccca ctntccgntc    660 cnncntcnc gctcgcgcn cgcccnccnc cccccc                                 697
```

<210> SEQ ID NO 18
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 18

```
ctcgtgtgaa gggtgcagta cctaagccgg agcggggtag aggcgggccg gcaccccctt      60
ctgacctcca gtgccgccgg cctcaagatc agacatggcc cagaacttga acgacttggc     120
gggacggctg cccgccgggc cccggggcat gggcacggcc ctgaagctgt tgctgggggc     180
cggcgccgtg gcctacggtg tgcgcgaatc tgtgttcacc gtggaaggcg ggcncagagc     240
catcttcttc aatcggatcg gtggagtgca caggacacta tcctgggccg anggccttca     300
cttcaggatc cttggttcca gtaccccanc atctatgaca ttcgggccag acctcgaaaa     360
aatctcctcc ctacaggctc caaagaccta cagatggtga atatctccct gcgagtgttg     420
tctcgaccaa tgctcangaa cttcctaaca tgttccancg cctaagggct ggactacnaa     480
gaacgantgt tgccgtccat tgtcacgaag tgctcaagaa tttngtggc caagttcaat      540
gncctcacnn ctgatcnccc agcggggcca agttanccct ggttgatccc cggggactg     600
acnnaaaagg gccaaggact tcccctcatc ctggataatg tggccntcac aaagctcaac    660
tttanccacc                                                            670
```

<210> SEQ ID NO 19
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 19

```
actagtgcca acctcagctc ccaggccagt tctctgaatg tcgaggagtt ccaggatctc      60
tggcctcagt tgtccttggt tatttgatggg ggacaaattg gggatggcca gagccccgag    120
tgtcgccttg gctcaactgt ggttgatttg tctgtgcccg gaaagtttgg catcattcgt     180
ccaggctgtg ccctggaaag tactacagcc atcctccaac agaagtacgg actgctcccc    240
tcacatgcgt cctacctgtg aaactctggg aagcaggaag gcccaagacc tggtgctgga    300
tactatgtgt ctgtccactg acgactgtca aggcctcatt tgcagaggcc accggagcta    360
gggcactagc ctgacttttta aggcagtgtg tctttctgag cactgtagac caagcccttg    420
gagctgctgg tttagccttg cacctgggga aaggatgtat ttatttgtat tttcatatat    480
cagccaaaag ctgaatggaa aagttnagaa cattcctagg tggccttatt ctaataagtt    540
tcttctgtct gttttgtttt tcaattgaaa agttattaaa taacagattt agaatctagt    600
gagacc                                                                606
```

<210> SEQ ID NO 20
<211> LENGTH: 449
<212> TYPE: DNA
<213> ORGANISM: Homo sapien

<400> SEQUENCE: 20

```
actagtaaac aacagcagca gaaacatcag tatcagcagc gtcgccagca ggagaatatg      60
```

```
cagcgccaga gccgaggaga accccgctc cctgaggagg acctgtccaa actcttcaaa      120
ccaccacagc cgcctgccag gatggactcg ctgctcattg caggccagat aaacacttac     180
tgccagaaca tcaaggagtt cactgcccaa aacttaggca agctcttcat ggcccaggct     240
cttcaagaat acaacaacta agaaaaggaa gtttccagaa aagaagttaa catgaactct     300
tgaagtcaca ccagggcaac tcttggaaga aatatatttg catattgaaa agcacagagg     360
atttctttag tgtcattgcc gattttggct ataacagtgt cttctagcc ataataaaat      420 aaaacaaaat cttgactgct tgctcaaaa                                       449

<210> SEQ ID NO 21
<211> LENGTH: 409
<212> TYPE: DNA
<213> ORGANISM: Homo sapien

<400> SEQUENCE: 21
tatcaatcaa ctggtgaata attaaacaat gtgtggtgtg atcatacaaa gggtaccact       60
caatgataaa aggaacaagc tgcctatatg tggaacaaca tggatgcatt tcagaaactt     120
tatgttgagt gaaagaacaa acacggagaa catactatgt ggttctcttt atgtaacatt     180
acagaaataa aaacagaggc aaccacctt gaggcagtat ggagtgagat agactggaaa      240
aaggaaggaa ggaaactcta cgctgatgga atgtctgtg tcttcattgg gtggtagtta      300
tgtggggata tacatttgtc aaaatttatt gaactatata ctaaagaact ctgcatttta     360
ttgggatgta ataataacct caattaaaaa gacaaaaaaa aaaaaaaaa                  409

<210> SEQ ID NO 22
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 22
acaattttca ttatcttaag cacattgtac atttctacag aacctgtgat tattctcgca       60
tgataaggat ggtacttgca tatggtgaat tactactgtt gacagtttcc gcagaaatcc     120
tatttcagtg gaccaacatt gtggcatggc agcaaatgcc aacattttgt ggaatagcag     180
caaatctaca agagccctg gttggttttt cgttttgttt tctttgtttt ttcccccttc       240
tcctgaatca gcagggatgg aagagggta gggaagttat gaattactcc ttccagtagt      300
agctctgaag tgtcacattt aatatcagtt tttttttaaac atgattctag ttnaatgtag     360
aagagagaag aaagaggaag tgttcacttt tttaatacac tgatttagaa atttgatgtc     420
ttatatcagt agttctgagg tattgatagc ttgctttatt tctgccttta cgttgacagt     480
gttgaagcag ggtgaataac tagggcata tatatttttt tttttgtaa gctgtttcat       540 gatgttttct ttggaatttc cggataagtt caggaaaaca tctgcatgtt gttatctagt     600
ctgaagttcn tatccatctc attacaacaa aaacncccag aacggnttg                 649

<210> SEQ ID NO 23
<211> LENGTH: 669
<212> TYPE: DNA
<213> ORGANISM: Homo sapien
<220> FEATURE:
<221> NAME/KEY: misc_feature
<222> LOCATION: (1)...(669)
<223> OTHER INFORMATION: n = A,T,C or G
```

<400> SEQUENCE: 23

```
actagtgccg tactggctga atccctgca ggaccaggaa gagaaccagt tcagactttg      60
tactctcagt caccagctct ggaattagat aaattccttg aagatgtcag gaatgggatc    120
tatcctctga cagcctttgg gctgcctcgg ccccagcagc cacagcagga ggaggtgaca    180
tcacctgtcg tgcccccctc tgtcaagact ccgacacctg aaccagctga ggtggagact    240
cgcaaggtgg tgctgatgca gtgcaacatt gagtcggtgg aggagggagt caaacaccac    300
ctgacacttc tgctgaagtt ggaggacaaa ctgaaccggc acctgagctg tgacctgatg    360
ccaaatgaga atatccccga gttggcggct gagctggtgc agctgggctt cattagtgag    420
gctgaccaga gccggttgac ttctctgcta aagagactt gaacaagttc aattttgcca     480
ggaacagtac cctcaactca gccgctgtca ccgtctcctc ttagagctca ctcgggccag    540
gccctgatct gcgctgtggc tgtcctggac gtgctgcacc ctctgtcctt cccccagtc    600
agtattacct gtgaagccct tccctccttt attattcagg anggctgggg gggctccttg    660
nttctaacc                                                            669
```

```
<210> SEQ ID NO 24
<211> LENGTH: 442
<212> TYPE: DNA
<213> ORGANISM: Homo sapien
```

<400> SEQUENCE: 24

```
actagtacca tcttgacaga ggatacatgc tcccaaaacg tttgttacca cacttaaaaa     60
tcactgccat cattaagcat cagtttcaaa attatagcca ttcatgattt acttttttcca   120
gatgactatc attattctag tcctttgaat ttgtaagggg aaaaaaaaca aaaacaaaaa    180
cttacgatgc acttttctcc agcacatcag atttcaaatt gaaaattaaa gacatgctat    240
ggtaatgcac ttgctagtac tacacacttt ggtacaacaa aaaacagagg caagaaacaa    300
cggaaagaga aaagccttcc tttgttggcc cttaaactga gtcaagatct gaaatgtaga    360
gatgatctct gacgatacct gtatgttctt attgtgtaaa taaaattgct ggtatgaaat    420
gacctaaaaa aaaaaaaaga aa                                             442
```

```
<210> SEQ ID NO 25
<211> LENGTH: 656
<212> TYPE: DNA
<213> ORGANISM: Homo sapien
<220> FEATURE:
<221> NAME/KEY: misc_feature
<222> LOCATION: (1)...(656)
<223> OTHER INFORMATION: n = A,T,C or G
```

<400> SEQUENCE: 25

```
tgcaagtacc acacactgtt tgaattttgc acaaaaagtg actgtaggat caggtgatag     60
ccccggaatg tacagtgtct tggtgcacca agatgccttc taaaggctga catacccttgg  120
accctaatgg ggcagagagt atagccctag cccagtggtg acatgaccac tcccttttggg  180
aggcctgagg tagaggggag tggtatgtgt tttctcagtg gaagcagcac atgagtgggt   240
gacaggatgt tagataaagg ctctagttag ggtgtcattg tcatttgaga gactgacaca   300
ctcctagcag ctggtaaagg ggtgctggan gccatggagg anctctagaa acattagcat   360
gggctgatct gattacttcc tggcatcccg ctcacttta tgggaagtct tattagangg    420
atgggacagt tttccatatc cttgctgtgg agctctggaa cactctctaa atttccctct    480
```

```
attaaaaatc actgccctaa ctacacttcc tccttgaagg aatagaaatg gaactttctc      540
tgacatantt cttggcatgg ggagccagcc acaaatgana atctgaacgt gtccaggttt      600
ctcctganac tcatctacat agaattggtt aaaccctccc ttggaataag gaaaaa         656
```

<210> SEQ ID NO 26
<211> LENGTH: 434
<212> TYPE: DNA
<213> ORGANISM: Homo sapien
<220> FEATURE:
<221> NAME/KEY: misc_feature
<222> LOCATION: (1)...(434)
<223> OTHER INFORMATION: n = A,T,C or G

<400> SEQUENCE: 26

```
actagttcag actgccacgc caaccccaga aaataccccca catgccagaa aagtgaagtc     60
ctaggtgttt ccatctatgt ttcaatctgt ccatctacca ggcctcgcga taaaaacaaa    120
acaaaaaaac gctgccaggt tttagaagca gttctggtct caaaaccatc aggatcctgc    180
caccagggtt cttttgaaat agtaccacat gtaaaggga atttggcttt cacttcatct     240
aataactgaa ttgtcaggct ttgattgata attgtagaaa taagtagcct tctgttgtgg    300
gaataagtta taatcagtat tcatctcttt gttttttgtc actcttttct ctctaattgt    360
gtcatttgta ctgtttgaaa aatatttctt ctatnaaatt aaactaacct gccttaaaaa    420
aaaaaaaaaa aaaa                                                      434
```

<210> SEQ ID NO 27
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 27

```
actagtccaa cacagtcaga aacattgttt tgaatcctct gtaaaccaag gcattaatct     60
taataaacca ggatccattt aggtaccact tgatataaaa aggatatcca taatgaatat    120
tttatactgc atcctttaca ttagccacta aatacgttat tgcttgatga agaccttttca   180 cagaatccta tggattgcag catttcactt ggctacttca tacccatgcc ttaaagaggg    240
gcagtttctc aaaagcagaa acatgccgcc agttctcaag ttttcctcct aactccattt    300
gaatgtaagg gcagctggcc cccaatgtgg ggaggtccga acatttttctg aattcccatt   360 ttcttgttcg cggctaaatg acagtttctg tcattactta gattccgatc ttctcccaaag  420 gtgttgattt acaaagaggc cagctaatag cagaaatcat gaccctgaaa gagagatgaa    480
attcaagctg tgagccaggc agganctcag tatgcaaag gtcttgagaa tcngccattt     540
ggtacaaaaa aaattttaaa gcntttatgt tataccatgg aaccatagaa anggcaaggg    600
aattgttaag aanaattta agtgtccaga cccanaanga aaaaaaaaaa aaaa           654
```

<210> SEQ ID NO 28
<211> LENGTH: 670
<212> TYPE: DNA
<213> ORGANISM: Homo sapien
<220> FEATURE:
<221> NAME/KEY: misc_feature
<222> LOCATION: (1)...(670)
<223> OTHER INFORMATION: n = A,T,C or G

<400> SEQUENCE: 28

```
cgtgtgcaca tactgggagg atttccacag ctgcacggtc acagcccctta cggattgcca      60 ggaaggggcg aaagatatgt gggataaact gagaaaagaa nccaaaaacc tcaacatcca     120
aggcagctta ttcgaactct gcggcagcgg caacggggcg gcggggtccc tgctcccggc     180
gttcccggtg ctcctggtgt ctctctcggc agctttagcg acctgncttt ccttctgagc     240
gtggggccag ctcccccccgc ggcgcccacc cacnctcact ccatgctccc ggaaatcgag     300
aggaagatca ttagttcttt ggggacgttn gtgattctct gtgatgctga aaaacactca     360 tagggaat gtgggaaatc ctganctctt tnttatntcg tntgatttct tgtgttttat        420
ttgccaaaat gttaccaatc agtgaccaac cnagcacagc caaaaatcgg acntcngctt     480
tagtccgtct tcacacacag aataagaaaa cggcaaaccc accccacttt tnantttnat     540
tattactaan ttttttctgt tgggcaaaag aatctcagga acngccctgg ggccnccgta     600
ctanagttaa ccnagctagt tncatgaaaa atgatgggct ccnccctcaat gggaaagcca     660 agaaaaagnc                                                            670

<210> SEQ ID NO 29
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 29
actagtcctc cacagcctgt gaatccccct agacctttca agcatagtga gcggagaaga      60
agatctcagc gtttagccac cttacccatg cctgatgatt ctgtagaaaa ggtttcttct     120
ccctctccag ccactgatgg gaaagtattc tccatcagtt ctcaaaatca gcaagaatct     180
tcagtaccag aggtgcctga tgttgcacat ttgccacttg agaagctggg accctgtctc     240
cctcttgact taagtcgtgg ttcagaagtt acagcaccgg tagcctcaga ttcctcttac     300
cgtaatgaat gtcccagggc agaaaaagag gatacncaga tgcttccaaa tccttcttcc     360
aaagcaatag ctgatgggaa gaggagctcc agcagcagca ggaatatcga aaacagaaaa     420
aaaagtgaaa ttgggaagac aaaagctcaa cagcatttgg taaggagaaa aganaagatg     480
aggaaggaag agagaagaga gacnaagatc nctacggacc gnnncggaag aagaagaagn     540
aaaaaanaaa a                                                          551

<210> SEQ ID NO 30
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 30
actagttcta tctggaaaaa gcccggggttg gaagaagctg tggagagtgc gtgtgcaatg      60
cgagactcat ttcttggaag catccctggc aaaaatgcag ctgagtacaa ggttatcact     120
gtgatagaac ctggactgct ttttgagata atagagatgc tgcagtctga agagacttcc     180
agcacctctc agttgaatga attaatgatg gcttctgagt caactttact ggctcaggaa     240
ccacgagaga tgactgcaga tgtaatcgag cttaaaggga aattcctcat caacttagaa     300
```

| | |
|---|---|
| ggtggtgata ttcgtgaaga gtcttcctat aaagtaattg tcatgccgac tacgaaagaa | 360 |
| aaatgccccc gttgttggaa gtatacagcg ggagtcttca gatacactgt gtcctcgatg | 420 |
| tgcagaagtt gtcagtggga aaatagtatt aacagctcac tcgagcaaga accctcctga | 480 |
| cagtactggg ctagaagttt ggatggatta tttacaatat aggaaagaaa gccaagaatt | 540 |
| aggtnatgag tggatgagta atggtggan gatggggaat tcaaatcaga attatggaag | 600 |
| aagttnttcc tgttactata gaaggaatt atgtttattt acatgcagaa aatatanatg | 660 |
| tgtggtgtgt accgtggatg gaan | 684 |

<210> SEQ ID NO 31
<211> LENGTH: 654
<212> TYPE: DNA
<213> ORGANISM: Homo sapien
<220> FEATURE:
<221> NAME/KEY: misc_feature
<222> LOCATION: (1)...(654)
<223> OTHER INFORMATION: n = A,T,C or G

<400> SEQUENCE: 31

| | |
|---|---|
| gcgcagaaaa ggaaccaata tttcagaaac aagcttaata ggaacagctg cctgtacatc | 60 |
| aacatcttct cagaatgacc cagaagttat catcgtggga gctggcgtgc ttggctctgc | 120 |
| tttggcagct gtgctttcca gagatggaag aaaggtgaca gtcattgaga gagacttaaa | 180 |
| agagcctgac agaatagttg gagaattcct gcagccgggt ggttatcatg ttctcaaaga | 240 |
| ccttggtctt ggagatacag tggaaggtct tgatgcccag gttgtaaatg gttacatgat | 300 |
| tcatgatcag ggaaagcaaa tcagangttc agattcctta ccctctgtca gaaaacaatc | 360 |
| aagtgcagag tggaagagct ttccatcacg gaagattcat catgagtctc cggaaagcag | 420 |
| ctatggcaga gcccaatgca aagtttattg aaggtgttgt gttacagtta ttagaggaag | 480 |
| atgatgttgt gatgggagtt cagtacaagg ataaagagac tgggagatat caaggaactc | 540 |
| catgctccac tgactgttgt tgcagatggg cttttctcca anttcaggaa aagcctggtc | 600 |
| tcaataaagt ttctgtatca ctcatttggt tggcttctta tgaagaatgc nccc | 654 |

<210> SEQ ID NO 32
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 32

| | |
|---|---|
| actagtgaag aaaagaaat tctgatacgg gacaaaaatg ctcttcaaaa catcattctt | 60 |
| tatcacctga caccaggagt tttcattgga aaaggatttg aacctggtgt tactaacatt | 120 |
| ttaaagacca cacaaggaag caaatctttt ctgaaagaag taaatgatac acttctggtg | 180 |
| aatgaattga atcaaaaga atctgacatc atgacaacaa atggtgtaat tcatgttgta | 240 |
| gataaactcc tctatccagc agacacacct gttggaaatg atcaactgct ggaaatactt | 300 |
| aataaattaa tcaaatacat ccaaattaag tttgttcgtg gtagcacctt caaagaaatc | 360 |
| cccgtgactg tctatnagcc aattattaaa aaatacacca aaatcattga tgggagtgcc | 420 |
| tgtgggaaat aactgaaaaa gagaccgaga agaacgaatc attacaggtc ctgaaataaa | 480 |
| atacctagga tttctactgg aggtggagaa acagaagaac tctgaagaaa ttgttacaag | 540 |
| aagangtccc aaggtcacca aattcattga aggtggtgat ggtctttatt tgaagatgaa | 600 |

-continued

```
gaaattaaaa gacgcttcag ggagacnccc catgaaggaa ttgccagcca caaaaaatt    660 cagggattag aaa                                                        673

<210> SEQ ID NO 33
<211> LENGTH: 673
<212> TYPE: DNA
<213> ORGANISM: Homo sapien
<220> FEATURE:
<221> NAME/KEY: misc_feature
<222> LOCATION: (1)...(673)
<223> OTHER INFORMATION: n = A,T,C or G

<400> SEQUENCE: 33
actagttatt tactttcctc cgcttcagaa ggtttttcag actgagagcc taagcatact     60
ggatctgttg tttcttttgg gtctcacctc atcagtgtgc atagtggcag aaattataaa    120
gaaggttgaa aggagcaggg aaaagatcca gaagcatgtt agttcgacat catcatcttt    180
tcttgaagta tgatgcatat tgcattattt tatttgcaaa ctaggaattg cagtctgagg    240
atcatttaga agggcaagtt caagaggata tgaagatttg agaactttt aactattcat    300 tgactaaaaa tgaacattaa tgttnaagac ttaagacttt aacctgctgg cagtcccaaa    360
tgaaattatg caactttgat atcatattcc ttgatttaaa ttgggctttt gtgattgant    420
gaaactttat aaagcatatg gtcagttatt tnattaaaaa ggcaaaacct gaaccacctt    480
ctgcacttaa agaagtctaa cagtacaaat acctatctat cttagatgga tntatttntt    540
tntattttta aatattgtac tatttatggt nggtggggct ttcttactaa tacacaaatn    600
aatttatcat ttcaanggca ttctatttgg gtttagaagt tgattccaag nantgcatat    660
ttcgctactg tnt                                                        673

<210> SEQ ID NO 34
<211> LENGTH: 684
<212> TYPE: DNA
<213> ORGANISM: Homo sapien
<220> FEATURE:
<221> NAME/KEY: misc_feature
<222> LOCATION: (1)...(684)
<223> OTHER INFORMATION: n = A,T,C or G

<400> SEQUENCE: 34
actagtttat tcaagaaaag aacttactga ttcctctgtt cctaaagcaa gagtggcagg     60
tgatcagggc tggtgtagca tccggttcct ttagtgcagc taactgcatt tgtcactgat    120
gaccaaggag gaaatcacta agacatttga gaagcagtgg tatgaacgtt cttggacaag    180
ccacagttct gagccttaac cctgtagttt gcacacaaga acgagctcca cctccccttc    240
ttcaggagga atctgtgcgg atagattggc tggactttc aatggttctg ggttgcaagt    300
gggcactgtt atggctgggt atggagcgga cagcccagg aatcagagcc tcagcccggc    360
tgcctggttg gaaggtacag gtgttcagca ccttcggaaa aagggcataa agtngtgggg    420
gacaattctc agtccaagaa gaatgcattg accattgctg gctatttgct tncctagtan    480
gaattggatn cattttgac cangatnntt ctnctatgct ttnttgcaat gaaatcaaat    540
cccgcattat ctacaagtgg tatgaagtcc tgcnnccccc agagaggctg ttcaggcnat    600
gtcttccaag ggcagggtgg gttacaccat tttacctccc ctctccccc agattatgna    660 cncagaagga atttntttcc tccc                                            684

<210> SEQ ID NO 35
```

```
<211> LENGTH: 614
<212> TYPE: DNA
<213> ORGANISM: Homo sapien
<220> FEATURE:
<221> NAME/KEY: misc_feature
<222> LOCATION: (1)...(614)
<223> OTHER INFORMATION: n = A,T,C or G

<400> SEQUENCE: 35
actagtccaa cgcgttngcn aatattcccc tggtagccta cttccttacc cccgaatatt    60
ggtaagatcg agcaatggct tcaggacatg ggttctcttc tcctgtgatc attcaagtgc   120
tcactgcatg aagactggct tgtctcagtg tntcaacctc accagggctg tctcttggtc   180
cacacctcgc tccctgttag tgccgtatga cagcccccat canatgacct tggccaagtc   240
acggtttctc tgtggtcaat gttggtnggc tgattggtgg aaagtanggt ggaccaaagg   300
aagncncgtg agcagncanc nccagttctg caccagcagc gcctccgtcc tactnggtg    360 ttccngtttc tcctggccct gngtgggcta nggcctgatt cgggaanatg cctttgcang   420
gaaggganga taantgggat ctaccaattg attctggcaa aacnatntct aagattnttn   480
tgctttatgt ggganacana tctanctctc atttnntgct gnanatnaca ccctactcgt   540
gntcgancnc gtcttcgatt ttcgganaca cnccantnaa tactggcgtt ctgttgttaa   600
aaaaaaaaaa aaaa                                                     614

<210> SEQ ID NO 36
<211> LENGTH: 686
<212> TYPE: DNA
<213> ORGANISM: Homo sapien
<220> FEATURE:
<221> NAME/KEY: misc_feature
<222> LOCATION: (1)...(686)
<223> OTHER INFORMATION: n = A,T,C or G

<400> SEQUENCE: 36
gtggctggcc cggttctccg cttctcccca tccctactt  tcctccctcc ctccctttcc    60
ctccctcgtc gactgttgct tgctggtcgc agactccctg accctcccct caccctcc     120 taacctcggt gccaccggat tgcccttctt ttcctgttgc ccagcccagc cctagtgtca   180
gggcgggggc ctggagcagc ccgaggcact gcagcagaag ananaaaaga cacgacnaac   240
ctcagctcgc cagtccggtc gctngcttcc cgccgcatgg caatnagaca dacgccgctc   300
acctgctctg ggcacacgcg acccgtggtt gatttggcct tcagtggcat cacccttatg   360
ggtatttctt aatcagcgct tgcaaagatg gttaacctat gctacgccag ggagatacag   420
gagactggat tggaacattt ttggggtcta aaggtctgtt tggggtgcaa cactgaataa   480
ggatgccacc aaagcagcta cagcagctgc agatttcaca gcccaagtgt gggatgctgt   540
ctcagganat naattgataa cctggctcat aacacattgt caagaatgtg gatttcccca   600
ggatattatt atttgtttac cggggganag gataactgtt tcncntattt taattgaaca   660
aactnaaaca aaanctaagg aaatcc                                       686

<210> SEQ ID NO 37
<211> LENGTH: 681
<212> TYPE: DNA
<213> ORGANISM: Homo sapien
<220> FEATURE:
<221> NAME/KEY: misc_feature
<222> LOCATION: (1)...(681)
<223> OTHER INFORMATION: n = A,T,C or G

<400> SEQUENCE: 37
```

```
gagacanacn naacgtcang agaanaaaag angcatggaa cacaanccag gcncgatggc    60
caccttccca ccagcancca gcgcccccca gcngccccca ngnccggang accangactc   120
cancctgnat caatctganc tctattcctg gcccatncct acctcggagg tggangccgn   180
aaaggtcgca cnnncagaga agctgctgcc ancaccancc gccccnnccc tgncgggctn   240
nataggaaac tggtgaccnn gctgcanaat tcatacagga gcacgcgang ggcacnnnct   300
cacactgagt tnnngatgan gcctnaccan ggacctnccc cagcnnattg annacnggac   360
tgcggaggaa ggaagacccc gnacnggatc ctggccggcn tgccacccccc caccccctag   420 gattatnccc cttgactgag tctctgaggg gctacccgaa cccgcctcca ttccctacca   480
natnntgctc natcgggact dacangctgg ggatnggagg ggctatcccc cancatcccc   540
tnanaccaac agcnacngan natngggggct ccccnggggtc ggngcaacnc tcctncaccc   600
cggcgcnggc cttcggtgnt gtcctccntc aacnaattcc naaanggcgg gccccccngt   660
ggactcctcn ttgttccctc c                                             681
```

<210> SEQ ID NO 38
<211> LENGTH: 687
<212> TYPE: DNA
<213> ORGANISM: Homo sapien
<220> FEATURE:
<221> NAME/KEY: misc_feature
<222> LOCATION: (1)...(687)
<223> OTHER INFORMATION: n = A,T,C or G

<400> SEQUENCE: 38

```
canaaaaaaa aaaacatggc cgaaaccagn aagctgcgcg atggcgccac ggcccctctt    60
ctcccggcct gtgtccggaa ggtttccctc cgaggcgccc cggctcccgc aagcggagga   120
gagggcggga cntgccgggg ccggagctca naggccctgg ggccgctctg ctctcccgcc   180
atcgcaaggg cggcgctaac ctnaggcctc cccgcaaagg tccccnangc ggnggcggcg   240 ggggggctgtg anaaccgcaa aaanaacgct gggcgcgcng cgaacccgtc caccccccgcg   300 aaggananac ttccacagan gcagcgtttc cacagcccan agccacnttt ctagggtgat   360
gcaccccagt aagttcctgn cggggaagct caccgctgtc aaaaaanctc ttcgctccac   420
cggcgcacna agggganggan ggcangangc tgccgcccgc acaggtcatc tgatcacgtc   480
gcccgcccta ntctgctttt gtgaatctcc actttgttca accccacccg ccgttctctc   540
ctccttgcgc cttcctctna ccttaanaac cagcttcctc tacccnatng tanttnctct   600
gcncnngtng aaattaattc ggtccnccgg aacctcttnc ctgtggcaac tgctnaaaga   660
aactgctgtt ctgnttactg cngtccc                                       687
```

<210> SEQ ID NO 39
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 39

```
actagtctgg cctacaatag tgtgattcat gtaggacttc tttcatcaat tcaaaccccc    60
tagaaaaacg tatacagatt atataagtag ggataagatt tctaacattt ctgggctctc   120
tgacccctgc gctagactgt ggaaagggag tattattata gtatacaaca ctgctgttgc   180
```

```
cttattagtt ataacatgat aggtgctgaa ttgtgattca caatttaaaa acactgtaat      240 ccaaacttt tttttttaact gtagatcatg catgtgaatg ttaatgttaa tttgttcaan      300
gttgttatgg gtagaaaaaa ccacatgcct taaaatttta aaaagcaggg cccaaactta      360
ttagtttaaa attagggggta tgtttccagt ttgttattaa ntggttatag ctctgtttag     420
aanaaatcna ngaacangat ttngaaantt aagntgacat tatttnccag tgacttgtta      480
atttgaaatc anacacggca ccttccgttt tggtnctatt ggnntttgaa tccaancngg      540
ntccaaatct tnttggaaac ngtccnttta acttttttac nanatcttat tttttattt      600 tggaatggcc ctatttaang ttaaaagggg ggggnnccac naccattcnt gaataaaact     660
naatatatat ccttggtccc ccaaaattta aggng                                695
```

```
<210> SEQ ID NO 40
<211> LENGTH: 674
<212> TYPE: DNA
<213> ORGANISM: Homo sapien
<220> FEATURE:
<221> NAME/KEY: misc_feature
<222> LOCATION: (1)...(674)
<223> OTHER INFORMATION: n = A,T,C or G

<400> SEQUENCE: 40
actagtagtc agttgggagt ggttgctata ccttgacttc atttatatga atttccactt       60
tattaaataa tagaaaagaa atcccggtg cttgcagtag agttatagga cattctatgc      120
ttacagaaaa tatagccatg attgaaatca aatagtaaag gctgttctgg cttttttatct     180 tcttagctca tcttaaataa gtagtacact tgggatgcag tgcgtctgaa gtgctaatca     240
gttgtaacaa tagcacaaat cgaacttagg atgtgtttct tctcttctgt gtttcgattt     300
tgatcaattc tttaattttg ggaacctata atacagtttt cctattcttg gagataaaaa     360
ttaaatggat cactgatatt taagtcattc tgcttctcat ctnaatattc catattctgt     420
attagganaa antacctccc agcacagccc cctctcaaac cccacccaaa accaagcatt     480
tggaatgagt ctcctttatt tccgaantgt ggatggtata acccatatcn ctccaatttc    540
tgnttgggtt gggtattaat ttgaactgtg catgaaaagn ggnaatcttt nctttgggtc     600
aaantttncc ggttaatttg nctngncaaa tccaatttnc tttaagggtg tctttataaa     660
atttgctatt cngg                                                      674
```

```
<210> SEQ ID NO 41
<211> LENGTH: 657
<212> TYPE: DNA
<213> ORGANISM: Homo sapien
<220> FEATURE:
<221> NAME/KEY: misc_feature
<222> LOCATION: (1)...(657)
<223> OTHER INFORMATION: n = A,T,C or G

<400> SEQUENCE: 41
gaaacatgca agtaccacac actgtttgaa ttttgcacaa aaagtgactg tagggatcag       60
gtgatagccc cggaatgtac agtgtcttgg tgcaccaaga tgccttctaa aggctgacat     120
accttgggac cctaatgggg cagagagtat agccctagcc cagtggtgac atgaccactc     180 cctttggag gctgaagtta aagggaatgg tatgtgtttt ctcatggaag cagcacatga     240
atnggtnaca ngatgttaaa ntaaggntct antttgggtg tcttgtcatt tgaaaaantg     300
acacactcct ancanctggt aaaggggtgc tggaagccat ggaagaactc taaaaacatt     360
agcatgggct gatctgatta cttcctggca tcccgctcac ttttatggga agtcttatta     420
```

| | |
|---|---|
| naaggatggg ananttttcc atatccttgc tgttggaact ctggaacact ctctaaattt | 480 |
| ccctctatta aaaatcactg nccttactac acttcctcct tganggaata gaaatggacc | 540 |
| tttctctgac ttagttcttg gcatgggganc cagcccaaat taaaatctga cttntccggt | 600 |
| ttctccngaa ctcacctact tgaattggta aaacctcctt tggaattagn aaaaacc | 657 |

<210> SEQ ID NO 42
<211> LENGTH: 389
<212> TYPE: DNA
<213> ORGANISM: Homo sapien
<220> FEATURE:
<221> NAME/KEY: misc_feature
<222> LOCATION: (1)...(389)
<223> OTHER INFORMATION: n = A,T,C or G

<400> SEQUENCE: 42

| | |
|---|---|
| actagtgctg aggaatgtaa acaagtttgc tgggccttgc gagacttcac caggttgttt | 60 |
| cgatagctca cactcctgca ctgtgcctgt cacccaggaa tgtctttttt aattagaaga | 120 |
| caggaagaaa acaaaaacca gactgtgtcc cacaatcaga aacctccgtt gtggcagang | 180 |
| ggccttcacc gccaccaggg tgtcccgcca gacagggaga gactccagcc ttctgaggcc | 240 |
| atcctgaaga attcctgttt ggggttgtg aaggaaaatc accggatt aaaagatgc | 300 |
| tgttgcctgc ccgcgtngtn gggaagggac tggtttcctg gtgaatttct aaaagaaaa | 360 |
| atattttaag ttaagaaaaa aaaaaaaaa | 389 |

<210> SEQ ID NO 43
<211> LENGTH: 279
<212> TYPE: DNA
<213> ORGANISM: Homo sapien

<400> SEQUENCE: 43

| | |
|---|---|
| actagtgaca agctcctggt cttgagatgt cttctcgtta aggagatggg cctttggag | 60 |
| gtaaaggata aaatgaatga gttctgtcat gattcactat tctagaactt gcatgaccctt | 120 |
| tactgtgtta gctcttgaa tgttcttgaa attttagact ttctttgtaa acaaataata | 180 |
| tgtccttatc attgtataaa agctgttatg tgcaacagtg tggagatcct tgtctgattt | 240 |
| aataaaatac ttaaacactg aaaaaaaaaa aaaaaaaa | 279 |

<210> SEQ ID NO 44
<211> LENGTH: 449
<212> TYPE: DNA
<213> ORGANISM: Homo sapien
<220> FEATURE:
<221> NAME/KEY: misc_feature
<222> LOCATION: (1)...(449)
<223> OTHER INFORMATION: n = A,T,C or G

<400> SEQUENCE: 44

| | |
|---|---|
| actagtagca tctttctac aacgttaaaa ttgcagaagt agcttatcat taaaaaacaa | 60 |
| caacaacaac aataacaata aatcctaagt gtaaatcagt tattctaccc cctaccaagg | 120 |
| atatcagcct gttttttccc tttttctcc tgggaataat tgtgggcttc ttcccaaatt | 180 |
| tctacagcct ctttcctctt ctcatgcttg agcttcctg tttgcacgca tgcgttgtgc | 240 |
| aagantgggc tgtttngctt ggantncggt ccnagtggaa ncatgctttc ccttgttact | 300 |
| gttggaagaa actcaaacct tcnaccccta ggtgttncca ttttgtcaag tcatcactgt | 360 |
| atttttgtac tggcattaac aaaaaaagaa atnaaatatt gttccattaa actttaataa | 420 |

```
aactttaaaa gggaaaaaaa aaaaaaaaa                                449
```

<210> SEQ ID NO 45
<211> LENGTH: 559
<212> TYPE: DNA
<213> ORGANISM: Homo sapien
<220> FEATURE:
<221> NAME/KEY: misc_feature
<222> LOCATION: (1)...(559)
<223> OTHER INFORMATION: n = A,T,C or G

<400> SEQUENCE: 45

```
actagtgtgg gggaatcacg gacacttaaa gtcaatctgc gaaataattc ttttattaca     60
cactcactga agtttttgag tcccagagag ccattctatg tcaaacattc caagtactct    120
ttgagagccc agcattacat caacatgccc gtgcagttca aaccgaagtc cgcaggcaaa    180
tttgaagctt tgcttgtcat tcaaacagat gaaggcaaga gtattgctat tcgactaatt    240
ggtgaagctc ttggaaaaaa ttnactagaa tacttttgt gttaagttaa ttacataagt     300
tgtattttgt taactttatc tttctacact acaattatgc ttttgtatat atattttgta    360
tgatggatat ctataattgt agattttgtt tttacaagct aatactgaag actcgactga    420
aatattatgt atctagccca tagtattgta cttaactttt acagggtgaa aaaaaaattc    480
tgtgtttgca ttgattatga tattctgaat aaatatggga atatatttta atgtgggtaa    540
aaaaaaaaaa aaaaaggaa                                                 559
```

<210> SEQ ID NO 46
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 46

```
actagttcta gtaccatggc tgtcatagat gcaaccatta tattccattt agtttcttcc     60
tcaggttccc taacaattgt tgaaactga atatatatgt ttatgtatgt gtgtgtgttc     120
actgtcatgt atatggtgta tatgggatgt gtgcagtttt cagttatata tatattcata    180
tatacatatg catatatatg tataatatac atatatacat gcatacactt gtataatata    240
catatatata cacatatatg cacacatatn atcactgagt tccaaagtga gtctttattt    300
ggggcaattg tattctctcc ctctgtctgc tcactgggcc tttgcaagac atagcaattg    360
cttgatttcc tttggataag agtcttatct tcggcactct tgactctagc cttaacttta    420
gatttctatt ccagaataccc tctcatatct atcttaaaac ctaaganggg taagangtc    480 ataagattgt agtatgaaag antttgctta gttaaattat atctcaggaa actcattcat    540
ctacaaatta aattgtaaaa tgatggtttg ttgtatctga aaaatgtttt agaacaagaa    600
atgtaactgg gtacctgtta tatcaaagaa cctcnattta ttaagtctcc tcatagccan    660
atccttatat ngccctctct gacctgantt aatananact tgaataatga atagttaatt    720
taggnttggg c                                                         731
```

<210> SEQ ID NO 47
<211> LENGTH: 640
<212> TYPE: DNA
<213> ORGANISM: Homo sapien
<220> FEATURE:
<221> NAME/KEY: misc_feature
<222> LOCATION: (1)...(640)
<223> OTHER INFORMATION: n = A,T,C or G

<400> SEQUENCE: 47

| | | | | | |
|---|---|---|---|---|---|
| tgcgngccgg | tttggcccttt | ctttgtanga | cactttcatc | cgccctgaaa | tcttcccgat | 60 |
| cgttaataac | tcctcaggtc | cctgcctgca | cagggttttt | tcttantttg | ttgcctaaca | 120 |
| gtacaccaaa | tgtgacatcc | tttcaccaat | atngattnct | tcataccaca | tcntcnatgg | 180 |
| anacgactnc | aacaattttt | tgatnacccn | aaanactggg | ggctnnaana | agtacantct | 240 |
| ggagcagcat | ggacctgtcn | gcnactaang | gaacaaangt | nntgaacatt | tacacaacct | 300 |
| ttggtatgtc | ttactgaaag | anagaaacat | gcttctnncc | ctagaccacg | aggncaaccg | 360 |
| caganattgc | caatgccaag | tccgagcggt | tagatcaggt | aatacattcc | atggatgcat | 420 |
| tacatacntt | gtccccgaaa | nanaagatgc | cctaanggct | tcttcanact | ggtccngaaa | 480 |
| acanctacac | ctggtgcttg | ganaacanac | tctttggaag | atcatctggc | acaagttccc | 540 |
| cccagtgggt | tttnccttgg | cacctanctt | accanatcna | ttcggaancc | attctttgcc | 600 |
| ntggcnttnt | nttgggacca | ntcttctcac | aactgnaccc | | | 640 |

<210> SEQ ID NO 48
<211> LENGTH: 257
<212> TYPE: DNA
<213> ORGANISM: Homo sapien

<400> SEQUENCE: 48

| | | | | | |
|---|---|---|---|---|---|
| actagtatat | gaaaatgtaa | atatcacttg | tgtactcaaa | caaaagttgg | tcttaagctt | 60 |
| ccaccttgag | cagccttgga | aacctaacct | gcctctttta | gcataatcac | attttctaaa | 120 |
| tgatttttctt | tgttcctgaa | aaagtgatttt | gtattagttt | tacatttgtt | ttttggaaga | 180 |
| ttatatttgt | atatgtatca | tcataaaata | tttaaataaa | aagtatcttt | agagtgaaaa | 240 |
| aaaaaaaaaa | aaaaaaa | | | | | 257 |

<210> SEQ ID NO 49
<211> LENGTH: 652
<212> TYPE: DNA
<213> ORGANISM: Homo sapien
<220> FEATURE:
<221> NAME/KEY: misc_feature
<222> LOCATION: (1)...(652)
<223> OTHER INFORMATION: n = A,T,C or G

<400> SEQUENCE: 49

| | | | | | |
|---|---|---|---|---|---|
| actagttcag | atgagtggct | gctgaagggg | ccccttgtc | attttcatta | taacccaatt | 60 |
| tccacttatt | tgaactctta | agtcataaat | gtataatgac | ttatgaatta | gcacagttaa | 120 |
| gttgacacta | gaaactgccc | atttctgtat | tacactatca | aataggaaac | attggaaaga | 180 |
| tggggaaaaa | aatcttattt | taaaatggct | tagaaagttt | tcagattact | ttgaaaattc | 240 |
| taaacttctt | tctgtttcca | aaacttgaaa | atatgtagat | ggactcatgc | attaagactg | 300 |
| ttttcaaagc | tttcctcaca | tttttaaagt | gtgatttttcc | ttttaatata | catatttatt | 360 |
| ttctttaaag | cagctatatc | ccaacccatg | actttggaga | tataccctatn | aaaccaatat | 420 |
| aacagcangg | ttattgaagc | agctttctca | aatgttgctt | cagatgtgca | agttgcaaat | 480 |
| tttattgtat | ttgtanaata | caattttttgt | tttaaactgt | atttcaatct | atttctccaa | 540 |
| gatgcttttc | atatagagtg | aaatatccca | ngataactgc | ttctgtgtcg | tcgcatttga | 600 |
| cgcataactg | cacaaatgaa | cagtgtatac | ctcttggttg | tgcattnacc | cc | 652 |

<210> SEQ ID NO 50
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 50

| | | | | | | |
|---|---|---|---|---|---|---|
| ttgcgctttg | atttttttag | ggcttgtgcc | ctgtttcact | tatagggtct | agaatgcttg | 60 |
| tgttgagtaa | aaaggagatg | cccaatattc | aaagctgcta | atgttctct | ttgccataaa | 120 |
| gactccgtgt | aactgtgtga | acacttggga | tttttctcct | ctgtcccgag | gtcgtcgtct | 180 |
| gcttctttt | ttgggttctt | tctagaagat | tgagaaatgc | atatgacagg | ctgagancac | 240 |
| ctccccaaac | acacaagctc | tcagccacan | gcagcttctc | cacagcccca | gcttcgcaca | 300 |
| ggctcctgga | nggctgcctg | ggggaggcag | acatgggagt | gccaaggtgg | ccagatggtt | 360 |
| ccaggactac | aatgtcttta | tttttaactg | tttgccactg | ctgccctcac | ccctgcccgg | 420 |
| ctctggagta | ccgtctgccc | canacaagtg | ggantgaaat | gggggtgggg | gggaacactg | 480 |
| attcccantt | aggggtgcc | taactgaaca | gtagggatan | aaggtgtgaa | cctgngaant | 540 |
| gcttttataa | attatnttcc | ttgttanatt | tatttttaa | tttaatctct | gttnaactgc | 600 |
| ccngggaaaa | gggaaaaaa | aaaaaaaat | tctntttaaa | cacatgaaca | | 650 |

<210> SEQ ID NO 51
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 51

| | | | | | | |
|---|---|---|---|---|---|---|
| tggcgtgcaa | ccagggtagc | tgaagtttgg | gtctgggact | ggagattggc | cattaggcct | 60 |
| cctganattc | cagctcccctt | ccaccaagcc | cagtcttgct | acgtggcaca | gggcaaacct | 120 |
| gactcccttt | gggcctcagt | ttcccctccc | cttcatgana | tgaaaagaat | actactttt | 180 |
| cttgttggtc | taacnttgct | ggacncaaag | tgtngtcatt | attgttgtat | tgggtgatgt | 240 |
| gtncaaaact | gcagaagctc | actgcctatg | agaggaanta | agagagatag | tggatganag | 300 |
| ggacanaagg | agtcattatt | tggtatagat | ccacccntcc | caacctttct | ctcctcagtc | 360 |
| cctgcncctc | atgtntctgg | tntggtgagt | cctttgtgcc | accanccatc | atgctttgca | 420 |
| ttgctgccat | cctgggaagg | gggtgnatcg | tctcacaact | tgttgtcatc | gtttganatg | 480 |
| catgctttct | tnatnaaaca | aanaaannaa | tgtttgacag | ngtttaaaat | aaaaaanaaa | 540 |
| caaaa | | | | | | 545 |

<210> SEQ ID NO 52
<211> LENGTH: 678
<212> TYPE: DNA
<213> ORGANISM: Homo sapien
<220> FEATURE:
<221> NAME/KEY: misc_feature
<222> LOCATION: (1)...(678)
<223> OTHER INFORMATION: n = A,T,C or G

<400> SEQUENCE: 52

| | | | | | | |
|---|---|---|---|---|---|---|
| actagtagaa | gaactttgcc | gcttttgtgc | ctctcacagg | cgcctaaagt | cattgccatg | 60 |

```
ggaggaagac gatttggggg gggaggggg ggggcangg tccgtgggc tttccctant      120
ntatctccat ntccantgnn cnntgtcgcc tcttccctcg tcncattnga anttantccc    180
tggnccccnn nccctctccn ncctncncct cccccctccg ncnctccnn cttttntan     240
ncttccccat ctccntcccc cctnanngtc ccaacnccgn cagcaatnnc ncacttnctc    300
nctccncncc tccnnccgtt cttctnttct cnacntntnc ncnnntnccn tgccnntnaa    360
annctctccc cnctgcaanc gattctctcc ctccncnnan ctntccactc cntncttctc    420
ncncgtcct nttcntcnnc ccacctctcn ccttcgnccc cantacnctc nccnccttn      480
cgnntcnttn nnntcctcnn accncccncc tcccttcncc cctcttctcc ccggtntntc    540
tctctcccnc nncncnncct cnnccntcc nngcgnccnt ttccgccccn cnccnccntt    600
ccttcntcnc cantccatcn cntntnccat nctncctncc nctcacnccc gctncccccn    660
ntctctttca cacngtcc                                                  678

<210> SEQ ID NO 53
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 53
tgaagatcct ggtgtcgcca tgggccgccg ccccgcccgt tgttaccggt attgtaagaa     60
caagccgtac ccaaagtctc gcttctgccg aggtgtccct gatgccaaaa ttcgcatttt   120
tgacctgggg cggaaaaaag caaaantgga tgagtctccg cttgtggcc acatggtgtc    180
agatcaatat gagcagctgt cctctgaagc cctgnangct gcccgaattt gtgccaataa   240
gtacatggta aaaagtngtg cnaagatgc ttccatatcc gggtgcggnt ccaccccttc    300
cacgtcatcc gcatcaacaa gatgttgtcc tgtgctgggg ctgacaggct cccaacaggc    360
atgcgaagtg cctttggaaa acccanggca ctgtggccag ggttcacatt gggccaattn    420
atcatgttca tccgcaccaa ctgcagaaca angaacntgt naattnaagc cctgcccagg    480
gncaanttca aatttcccgg cc                                             502

<210> SEQ ID NO 54
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 54
actagtccaa gaaaatatg cttaatgtat attacaaagg ctttgtatat gttaacctgt      60
tttaatgcca aaagtttgct tgtccacaa tttccttaag acctcttcag aaagggattt    120
gtttgcctta atgaatactg ttgggaaaaa acacagtata atgagtgaaa agggcagaag    180
caagaaattt ctacatctta gcgactccaa gaagaatgag tatccacatt tagatggcac    240
attatgagga ctttaatctt tccttaaaca caataatgtt ttcttttttc ttttattcac    300
atgatttcta agtatatttt tcatgcagga cagttttca accttgatgt acagtgactg      360
tgttaaattt ttctttcagt ggcaacctct ataatcttta aaatatggtg agcatcttgt    420
ctgttttgaa ngggatatga cnatnaatct atcagatggg aaatcctgtt tccaagttag    480
```

```
<210> SEQ ID NO 55
<211> LENGTH: 606
<212> TYPE: DNA
<213> ORGANISM: Homo sapien
<220> FEATURE:
<221> NAME/KEY: misc_feature
<222> LOCATION: (1)...(606)
<223> OTHER INFORMATION: n = A,T,C or G

<400> SEQUENCE: 55
actagtaaaa agcagcattg ccaaataatc cctaattttc cactaaaaat ataatgaaat      60
gatgttaagc tttttgaaaa gtttaggtta aacctactgt tgttagatta atgtatttgt     120
tgcttccctt tatctggaat gtggcattag cttttttatt ttaaccctct ttaattctta     180
ttcaattcca tgacttaagg ttggagagct aaacactggg attttttggat aacagactga    240
cagttttgca taattataat cggcattgta catagaaagg atatggctac cttttgttaa     300
atctgcactt tctaaatatc aaaaaggga aatgaagtat aaatcaattt ttgtataatc      360
tgtttgaaac atganttta tttgcttaat attanggctt tgcccttttc tgttagtctc      420
ttgggatcct gtgtaaaact gttctcatta aacaccaaac agttaagtcc attctctggt    480
actagctaca aattccgttt catattctac ntaacaattt aaattaactg aaatatttct    540
anatggtcta cttctgtcnt ataaaaacna aacttgantt nccaaaaaaa aaaaaaaaa    600
aaaaaa                                                                606

<210> SEQ ID NO 56
<211> LENGTH: 183
<212> TYPE: DNA
<213> ORGANISM: Homo sapien

<400> SEQUENCE: 56
actagtatat ttaaacttac aggcttattt gtaatgtaaa ccaccatttt aatgtactgt     60
aattaacatg gttataatac gtacaatcct tccctcatcc catcacacaa cttttttttgt   120
gtgtgataaa ctgattttgg tttgcaataa aaccttgaaa aataaaaaaa aaaaaaaaaa    180
aaa                                                                   183

<210> SEQ ID NO 57
<211> LENGTH: 622
<212> TYPE: DNA
<213> ORGANISM: Homo sapien
<220> FEATURE:
<221> NAME/KEY: misc_feature
<222> LOCATION: (1)...(622)
<223> OTHER INFORMATION: n = A,T,C or G

<400> SEQUENCE: 57
actagtcact actgtcttct ccttgtagct aatcaatcaa tattcttccc ttgcctgtgg     60
gcagtggaga gtgctgctgg gtgtacgctg cacctgccca ctgagttggg gaaagaggat    120
aatcagtgag cactgttctg ctcagagctc ctgatctacc ccaccccta ggatccagga     180
ctgggtcaaa gctgcatgaa accaggccct ggcagcaacc tgggaatggc tggaggtggg    240
agagaacctg acttctcttt ccctctccct cctccaacat tactggaact ctatcctgtt    300
agggatcttc tgagcttgtt tccctgctgg gtgggacaga agacaaagga gaagggangg    360
tctacaanaa gcagcccttc tttgtcctct ggggttaatg agcttgacct ananttcatg    420
```

| gaganaccan aagcctctga tttttaattt ccntnaaatg tttgaagtnt atatntacat | 480 |
| atatatattt ctttnaatnt ttgagtcttt gatatgtctt aaaatccant ccctctgccn | 540 |
| gaaacctgaa ttaaaaccat gaanaaaaat gtttncctta aagatgttan taattaattg | 600 |
| aaacttgaaa aaaaaaaaa aa | 622 |

<210> SEQ ID NO 58
<211> LENGTH: 433
<212> TYPE: DNA
<213> ORGANISM: Homo sapien

<400> SEQUENCE: 58

| gaacaaattc tgattggtta tgtaccgtca aaagacttga agaaatttca tgattttgca | 60 |
| gtgtggaagc gttgaaaatt gaagttact gcttttccac ttgctcatat agtaaaggga | 120 |
| tcctttcagc tgccagtgtt gaataatgta tcatccagag tgatgttatc tgtgacagtc | 180 |
| accagcttta agctgaacca ttttatgaat accaaataaa tagacctctt gtactgaaaa | 240 |
| catatttgtg actttaatcg tgctgcttgg atagaaatat ttttactggt tcttctgaat | 300 |
| tgacagtaaa cctgtccatt atgaatggcc tactgttcta ttatttgttt tgacttgaat | 360 |
| ttatccacca aagacttcat ttgtgtatca tcaataaagt tgtatgtttc aactgaaaaa | 420 |
| aaaaaaaaaa aaa | 433 |

<210> SEQ ID NO 59
<211> LENGTH: 649
<212> TYPE: DNA
<213> ORGANISM: Homo sapien
<220> FEATURE:
<221> NAME/KEY: misc_feature
<222> LOCATION: (1)...(649)
<223> OTHER INFORMATION: n = A,T,C or G

<400> SEQUENCE: 59

| actagttatt atctgacttt cnggttataa tcattctaat gagtgtgaag tagcctctgg | 60 |
| tgtcatttgg atttgcattt ctctgatgag tgatgctatc aagcaccttt gctggtgctg | 120 |
| ttggccatat gtgtatgttc cctggagaag tgtctgtgct gagccttggc ccactttta | 180 |
| attaggcgtn tgtctttta ttactgagtt gtaaganttc tttatatatt ctggattcta | 240 |
| gacccttatc agatacatgg tttgcaaata ttttctccca ttctgtgggt tgtgttttca | 300 |
| ctttatcgat aatgtcctta gacatataat aaatttgtat tttaaagtg acttgatttg | 360 |
| ggctgtgcaa ggtgggctca cgcttgtaat cccagcactt tgggagactg aggtgggtgg | 420 |
| atcatatgan gangctagga gttcgaggtc agcctggcca gcatagcgaa aacttgtctc | 480 |
| tacnaaaaat acaaaaatta gtcaggcatg gtggtgcacg tctgtaatac cagcttctca | 540 |
| ggangctgan gcacaaggat cacttgaacc ccagaangaa gangttgcag tganctgaag | 600 |
| atcatgccag ggcaacaaaa atgagaactt gtttaaaaaa aaaaaaaa | 649 |

<210> SEQ ID NO 60
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 60

| actagttcag gccttccagt tcactgacaa acatgggaa gtgtgcccag ctggctggaa | 60 |

-continued

```
acctggcagt gataccatca agcctgatgt ccaaaagagc aaagaatatt tctccaagca     120
gaagtgagcg ctgggctgtt ttagtgccag gctgcggtgg gcagccatga gaacaaaacc     180
tcttctgtat ttttttttc cattagtana acacaagact cngattcagc cgaattgtgg      240
tgtcttacaa ggcagggctt tcctacaggg ggtgganaaa acagcctttc ttcctttggt     300
aggaatggcc tgagttggcg ttgtgggcag gctactggtt tgtatgatgt attagtagag     360
caacccatta atcttttgta gtttgtatna aacttganct gagaccttaa acaaaaaaaa     420
aaa                                                                   423

<210> SEQ ID NO 61
<211> LENGTH: 423
<212> TYPE: DNA
<213> ORGANISM: Homo sapien
<220> FEATURE:
<221> NAME/KEY: misc_feature
<222> LOCATION: (1)...(423)
<223> OTHER INFORMATION: n = A,T,C or G

<400> SEQUENCE: 61
cgggactgga atgtaaagtg aagttcggag ctctgagcac gggctcttcc cgccgggtcc      60
tccctcccca gacccagag ggagaggccc acccgccca gccccgcccc agccctgct       120 caggtctgag tatggctggg agtcggggc cacaggcctc tagctgtgct gctcaagaag     180
actggatcag ggtanctaca agtggccggg ccttgccttt gggattctac cctgttccta     240
atttggtgtt ggggtgcggg gtccctggcc ccttttcca cactncctcc ctccngacag     300
caacctccct tggggcaatt gggcctggnt ctccncccgn tgttgcnacc ctttgttggt     360 ttaaggncttt taaaaatgtt annttttccc ntgccngggt taaaaaagga aaaactnaa     420 aaa                                                                   423

<210> SEQ ID NO 62
<211> LENGTH: 683
<212> TYPE: DNA
<213> ORGANISM: Homo sapien
<220> FEATURE:
<221> NAME/KEY: misc_feature
<222> LOCATION: (1)...(683)
<223> OTHER INFORMATION: n = A,T,C or G

<400> SEQUENCE: 62
gctggagagg ggtacggact ttcttggagt tgtcccaggt tggaatgaga ctgaactcaa       60
gaagagaccc taagagactg gggaatggtt cctgccttca ggaaagtgaa agacgcttag     120
gctgtcaaca cttaaaggaa gtccccttga agcccagagt ggacagacta gacccattga     180
tggggccact ggccatggtc cgtggacaag acattccngt gggccatggc acaccggggg     240
ggatcaaaat gtgtacttgt ggggtctcgc cccttgccaa aaccaaacca ntcccactcc     300
tgtcnttgga ctttcttccc attccctcct ccccaaatgc acttcccctc ctccctctgc     360
ccctcctgtg ttttttggaat tctgtttccc tcaaaattgt taattttta nttttngacc     420 atgaacttat gtttggggtc nangttcccc ttnccaatgc atactaatat attaatggtt     480
atttattttt gaatatttt ttaatgaact tggaaaaaat tnntggaatt tccttncttc      540
cnttttnttt ggggggggtg ggggntggg ttaaaatttt tttggaancc cnatnggaaa     600
ttnttacttg gggcccccct naaaaaantn anttccaatt cttnnatngc ccctnttccn     660
ctaaaaaaaa ananannaaa aan                                             683
```

<210> SEQ ID NO 63
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 63

| | | | | | |
|---|---|---|---|---|---|
| actagtcata | aagggtgtgc | gcgtcttcga | cgtggcggtc | ttggcgccac | tgctgcgaga | 60 |
| cccggccctg | gacctcaagg | tcatccactt | ggtgcgtgat | ccccgcgcgg | tggcgagttc | 120 |
| acggatccgc | tcgcgccacg | gcctcatccg | tgagagccta | caggtggtgc | gcagccgaga | 180 |
| ccgcgagctc | accgcatgcc | cttcttggag | gccgcgggcc | acaagcttgg | cgcccanaaa | 240 |
| gaaggcgtng | ggggcccgca | aantaccacg | ctctgggcgc | tatggaangt | cctcttgcaa | 300 |
| taatattggt | tnaaaanctg | canaanagcc | cctgcanccc | cctgaactgg | gntgcagggc | 360 |
| cncttacctn | gtttggntgc | ggttacaaag | aacctgtttn | ggaaaaccct | nccnaaaacc | 420 |
| ttccgggaaa | attntncaaa | tttttnttgg | ggaattnttg | ggtaaacccc | ccnaaaatgg | 480 |
| gaaacntttt | tgccctnnaa | antaaaccat | tnggttccgg | gggccccccc | ncaaaccct | 540 |
| tttttntttt | tttntgcccc | cantnnccc | ccggggcccc | ttttttttgg | ggaaaanccc | 600 |
| cccccctncc | nananttta | aaagggnggg | anaatttttn | nttnccccc | gggnccccn | 660 |
| ggngntaaaa | nggtttcncc | cccccgaggg | gnggggnnnc | ctcnnaaacc | cntntcnnna | 720 |
| ccncnttttn | n | | | | | 731 |

<210> SEQ ID NO 64
<211> LENGTH: 313
<212> TYPE: DNA
<213> ORGANISM: Homo sapien
<220> FEATURE:
<221> NAME/KEY: misc_feature
<222> LOCATION: (1)...(313)
<223> OTHER INFORMATION: n = A,T,C or G

<400> SEQUENCE: 64

| | | | | | |
|---|---|---|---|---|---|
| actagttgtg | caaaccacga | ctgaagaaag | acgaaaagtg | ggaaataact | tgcaacgtct | 60 |
| gttagagatg | gttgctacac | atgttgggtc | tgtagagaaa | catcttgagg | agcagattgc | 120 |
| taaagttgat | agagaatatg | aagaatgcat | gtcagaagat | ctctcggaaa | atattaaaga | 180 |
| gattagagat | aagtatgaga | agaaagctac | tctaattaag | tcttctgaag | aatgaagatn | 240 |
| aaatgttgat | catgtatata | tatccatagt | gaataaaatt | gtctcagtaa | agttgtaaaa | 300 |
| aaaaaaaaaa | aaa | | | | | 313 |

<210> SEQ ID NO 65
<211> LENGTH: 420
<212> TYPE: DNA
<213> ORGANISM: Homo sapien
<220> FEATURE:
<221> NAME/KEY: misc_feature
<222> LOCATION: (1)...(420)
<223> OTHER INFORMATION: n = A,T,C or G

<400> SEQUENCE: 65

| | | | | | |
|---|---|---|---|---|---|
| actagttccc | tggcaggcaa | gggcttccaa | ctgaggcagt | gcatgtgtgg | cagagagagg | 60 |
| caggaagctg | gcagtggcag | cttctgtgtc | tagggagggg | tgtggctccc | tccttccctg | 120 |
| tctgggaggt | tggagggaag | aatctaggcc | ttagcttgcc | ctcctgccac | ccttcccctt | 180 |

```
gtagatactg ccttaacact ccctcctctc tcagctgtgg ctgccaccca agccaggttt      240
ctccgtgctc actaatttat ttccaggaaa ggtgtgtgga agacatgagc cgtgtataat      300
atttgtttta acattttcat tgcaagtatt gaccatcatc cttggttgtg tatcgttgta      360
acacaaatta atgatattaa aaagcatcca acaaagccn annnnnaana nnannngaaa      420
```

<210> SEQ ID NO 66
<211> LENGTH: 676
<212> TYPE: DNA
<213> ORGANISM: Homo sapien
<220> FEATURE:
<221> NAME/KEY: misc_feature
<222> LOCATION: (1)...(676)
<223> OTHER INFORMATION: n = A,T,C or G

<400> SEQUENCE: 66

```
actagtttcc tatgatcatt aaactcattc tcagggttaa gaaaggaatg taaatttctg       60
cctcaatttg tacttcatca ataagttttt gaagagtgca gatttttagt caggtcttaa      120
aaataaactc acaatctgg atgcatttct aaattctgca aatgtttcct ggggtgactt       180
aacaaggaat aatcccacaa tatacctagc tacctaatac atggagctgg ggctcaaccc      240
actgttttta aggatttgcg cttacttgtg gctgaggaaa aataagtagt tccgagggaa      300
gtagttttta aatgtgagct tatagatngg aaacagaata tcaacttaat tatggaaatt      360
gttagaaacc tgttctcttg ttatctgaat cttgattgca attactattg tactggatag      420
actccagccc attgcaaagt ctcagatatc ttanctgtgt agttgaattc cttggaaatt      480 cttttttaaga aaaaattgga gttttnaaaga aataaacccc tttgttaaat gaagcttggc      540
tttttggtga aaaanaatca tcccgcaggg cttattgttt aaaaanggaa ttttaagcct      600
ccctggaaaa anttgttaat taaatgggga aaatgntggg naaaaattat ccgttagggt      660
ttaaagggaa aactta                                                      676
```

<210> SEQ ID NO 67
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 67

```
caccattaaa gctgcttacc aagaacttcc ccagcatttt gacttccttg tttgatagct       60
gaattgtgag caggtgatag aagagccttt ctagttgaac atacagataa tttgctgaat      120
acattccatt taatgaaggg gttacatctg ttacgaagct actaagaagg agcaagagca      180
taggggaaaa aaatctgatc agaacgcatc aaactcacat gtgcccctc tactacaaac       240 agattgtagt gctgtggtgg tttattccgt tgtgcagaac ttgcaagctg agtcactaaa      300
cccaaagaga ggaaattata ggttagttaa acattgtaat cccaggaact aagtttaatt      360
cacttttgaa gtgttttgtt ttttattttt ggtttgtctg atttactttg ggggaaaang      420
ctaaaaaaaa agggatatca atctctaatt cagtgcccac taaagttgt ccctaaaaag       480 tctttactgg aanttatggg actttttaag ctccaggtnt tttggtcctc caaattaacc      540
ttgcatgggc cccttaaaat tgttgaangg cattcctgcc tctaagtttg gggaaaattc      600
ccccnttttn aaaatttgga                                                  620
```

```
<210> SEQ ID NO 68
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 68
actagtagct ggtacataat cactgaggag ctatttctta acatgctttt atagaccatg      60
ctaatgctag accagtattt aagggctaat ctcacacctc cttagctgta agagtctggc     120
ttagaacaga cctctctgtg caataacttg tggccactgg aaatccctgg gccggcattt     180
gtattggggt tgcaatgact cccaagggcc aaaagagtta aaggcacgac tgggatttct     240
tctgagactg tggtgaaact ccttccaagg ctgaggcggt cagtangtgc tctgggaggg     300
actcggcacc actttgatat tcaacaagcc acttgaagcc caattataaa attgttattt     360
tacagctgat ggaactcaat ttgaaccttc aaaactttgt tagtttatcc tattatattg     420
ttaaacctaa ttcatttgt ctagcattgg atttggttcc tgtngcatat gttttttttcn     480 cctatgtgct cccctccccc nnatcttaat ttaaaccnca attttgcnat tcnccnnnnn     540
nannnannna a                                                         551

<210> SEQ ID NO 69
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 69
cagaaatgga aagcagagtt ttcatttctg tttataaacg tctccaaaca aaaatggaaa      60
gcagagtttt cattaaatcc ttttacctt ttttttttctt ggtaatcccc tcaaataaca     120
gtatgtggga tattgaatgt taaagggata ttttttttcta ttattttat aattgtacaa     180 aattaagcaa atgttaaaag ttttatatgc tttattaatg ttttcaaaag gtatnataca     240
tgtgatacat tttttaagct tcagttgctt gtcttctggt actttctgtt atgggctttt     300
ggggagccan aaaccaatct acnatctctt tttgtttgcc aggacatgca ataaaattta     360
aaaaataaat aaaactatt nagaaattga aaaaaa                               396

<210> SEQ ID NO 70
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 70
actagtgcaa aagcaaatat aaacatcgaa aaggcgttcc tcacgttagc tgaagatatc      60
cttcgaaaga cccctgtaaa agagcccaac agtgaaaatg tagatatcag cagtggagga     120
ggcgtgacag gctggaagag caaatgctgc tgagcattct cctgttccat cagttgccat     180
ccactacccc gttttctctt cttgctgcaa aataaaccac tctgtccatt tttaactcta     240
aacagatatt tttgtttctc atcttaacta tccaagccac ctatttttatt tgttctttca     300
```

```
tctgtgactg cttgctgact ttatcataat tttcttcaaa caaaaaaatg tatagaaaaa    360
tcatgtctgt gacttcattt ttaaatgnta cttgctcagc tcaactgcat ttcagttgtt    420
ttatagtcca gttcttatca acattnaaac ctatngcaat catttcaaat ctattctgca    480
aattgtataa gaataaaagt tagaatttaa caattaaaaa aaaaaaaaa aaaaaa        536
```

<210> SEQ ID NO 71
<211> LENGTH: 865
<212> TYPE: DNA
<213> ORGANISM: Homo sapien
<220> FEATURE:
<221> NAME/KEY: misc_feature
<222> LOCATION: (1)...(865)
<223> OTHER INFORMATION: n = A,T,C or G

<400> SEQUENCE: 71

```
gacaaagcgt taggagaaga anagaggcag ggaanactnc ccaggcacga tggccncctt     60
cccaccagca accagcgccc cccaccagcc cccaggcccg gacgacgaag actccatcct    120
ggattaatct nacctctntc gcctgnccca ttcctacctc ggaggtggag gccgaaagg    180 tcncaccaag aganaanctg ctgccaacac caaccgcccc agccctggcg ggcacganag    240
gaaactggtg accaatctgc agaattctna gaggaaaag cnaggggccc cgcgctnaga    300
cagagctgga tatgangcca gaccatggac nctacncccn ncaatncana cgggactgcg    360
gaagatggan gacccncgac nngatcaggc cngctnncca nccccccacc cctatgaatt    420
attcccgctg aangaatctc tganngcctt ccannaaagc gcctcccnc cnaacgnaan    480 tncaacatng ggattanang ctgggaactg naaggggcaa ancctnnaat atccccagaa    540
acaanctctc ccnaanaaac tggggcncct catnggtggn accaactatt aactaaaccg    600
cacgccaagn aantataaaa gggggcccc tccncggnng acccccttt gtcccttaat     660 ganggttatc cnccttgcgt accatggtnc ccnnttctgt ntgnatgttt ccnctcccct    720
ccncctatnt cnagccgaac tcnnattnc ccggggtgc natcnantng tncnccttn     780 ttngttgncc cngcccttc cgncggaacn cgtttccccg ttantaacgg cacccggggn    840
aagggtgntt ggccccctcc ctccc                                         865
```

<210> SEQ ID NO 72
<211> LENGTH: 560
<212> TYPE: DNA
<213> ORGANISM: Homo sapien
<220> FEATURE:
<221> NAME/KEY: misc_feature
<222> LOCATION: (1)...(560)
<223> OTHER INFORMATION: n = A,T,C or G

<400> SEQUENCE: 72

```
cctggacttg tcttggttcc agaacctgac gacccggcga cggcgacgtc tcttttgact     60
aaaagacagt gtccagtgct ccngcctagg agtctacggg gaccgcctcc cgcgccgcca    120
ccatgcccaa cttctctggc aactggaaaa tcatccgatc ggaaaacttc gangaattgc    180
tcnaantgct gggggtgaat gtgatgctna ngaanattgc tgtggctgca gcgtccaagc    240
cagcagtgga gatcnacag gagggagaca ctttctacat caaaacctcc accaccgtgc    300
gcaccacaaa gattaacttc nnngttgggg aggantttga ggancaaact gtggatngga    360
ngcctgtnaa aacctggtga aatgggagaa tganaataaa atggtctgtg ancanaaact    420
cctgaaagga gaaggccccc anaactcctg gaccngaaaa actgacccnc cnatnggga    480
```

```
actgatncttgaaccctgaacgggcgggatganccttttttnttgccncnaangggttc540
tttccntttccccaaaaaaa560
```

<210> SEQ ID NO 73
<211> LENGTH: 379
<212> TYPE: DNA
<213> ORGANISM: Homo sapien
<220> FEATURE:
<221> NAME/KEY: misc_feature
<222> LOCATION: (1)...(379)
<223> OTHER INFORMATION: n = A,T,C or G

<400> SEQUENCE: 73

```
ctggggancc ggcggtnngc nccatntcnn gncgcgaagg tggcaataaa aanccnctga      60
aaccgcncaa naaacatgcc naagatatgg acgaggaaga tngngctttc nngnacaanc     120
gnanngagga acanaacaaa ctcnangagc tctcaagcta atgccgcggg aaggggccc      180
ttggccacnn gtggaattaa gaaatctggc aaanngtann tgttccttgt gcctnangag     240
ataagngacc ctttatttca tctgtattta aacctctctn ttccctgnca taacttcttt    300
tnccacgtan agntggaant anttgttgtc ttggactgtt gtncatttta gannaaactt    360
ttgttcaaaa aaaaaataa                                                  379
```

<210> SEQ ID NO 74
<211> LENGTH: 437
<212> TYPE: DNA
<213> ORGANISM: Homo sapien
<220> FEATURE:
<221> NAME/KEY: misc_feature
<222> LOCATION: (1)...(437)
<223> OTHER INFORMATION: n = A,T,C or G

<400> SEQUENCE: 74

```
actagttcag actgccacgc aacccccaga aaatacccca catgccagaa aagtgaagtc      60
ctaggtgttt ccatctatgt ttcaatctgt ccatctacca ggcctcgcga taaaaacaaa    120
acaaaaaaac gctgccaggt tttanaagca gttctggtct caaaaccatc aggatcctgc    180
caccagggtt cttttgaaat agtaccacat gtaaaaggga atttggcttt cacttcatct    240
aatcactgaa ttgtcaggct ttgattgata attgtagaaa taagtagcct tctgttgtgg    300
gaataagtta taatcagtat tcatctcttt gttttttgtc actcttttct ctctnattgt    360
gtcatttgta ctgtttgaaa aatatttctt ctataaaatt aaactaacct gccttaaaaa    420
aaaaaaaaaa aaaaaaa                                                   437
```

<210> SEQ ID NO 75
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 75

```
ctccgtcgcc gccaagatga tgtgcggggc gccctccgcc acgcagccgg ccaccgccga      60
gacccagcac atcgccgacc aggtgaggtc ccagcttgaa gagaaagaaa acaagaagtt    120
ccctgtgttt aaggccgtgt cattcaagag ccaggtggtc gcgggacaa actacttcat     180
caaggtgcac gtcggcgacg aggacttcgt cacacctgcga gtgttccaat ctctccctca    240
tgaaaacaag cccttgacct tatctaacta ccagaccaac aaagccaagc atgatgagct    300
```

```
gacctatttc tgatcctgac tttggacaag gcccttcagc cagaagactg acaaagtcat    360
cctccgtcta ccagagcgtg cacttgtgat cctaaaataa gcttcatctc cgggctgtgc    420
ccttggggtg aaggggcan gatctgcact gcttttgcat ttctcttcct aaatttcatt     480
gtgttgattc tttccttcca ataggtgatc ttnattactt tcagaatatt ttccaaatna    540
gatatatttt naaaatcctt aaaaaaaaaa aaaaaaaa                             579

<210> SEQ ID NO 76
<211> LENGTH: 666
<212> TYPE: DNA
<213> ORGANISM: Homo sapien
<220> FEATURE:
<221> NAME/KEY: misc_feature
<222> LOCATION: (1)...(666)
<223> OTHER INFORMATION: n = A,T,C or G

<400> SEQUENCE: 76
gtttatccta tctctccaac cagattgtca gctccttgag ggcaagagcc acagtatatt     60
tccctgtttc ttccacagtg cctaataata ctgtggaact aggttttaat aattttttaa    120
ttgatgttgt tatgggcagg atggcaacca gaccattgtc tcagagcagg tgctggctct    180
ttcctggcta ctccatgttg gctagcctct ggtaacctct tacttattat cttcaggaca    240
ctcactacag ggaccaggga tgatgcaaca tccttgtctt tttatgacag gatgtttgct    300
cagcttctcc aacaataaaa agcacgtggt aaaacacttg cggatattct ggactgtttt    360
taaaaaatat acagtttacc gaaaatcata ttatcttaca atgaaaagga ntttatagat    420
cagccagtga acaaccttt cccaccatac aaaaattcct tttcccgaan gaaaanggct     480
ttctcaataa ncctcactt cttaanatct tacaagatag ccccganatc ttatcgaaac     540
tcattttagg caaatatgan ttttattgtn cgttacttgt ttcaaaattt ggtattgtga    600
atatcaatta ccaccccat ctcccatgaa anaaanggga aanggtgaan ttcntaancg     660
cttaaa                                                               666

<210> SEQ ID NO 77
<211> LENGTH: 396
<212> TYPE: DNA
<213> ORGANISM: Homo sapien
<220> FEATURE:
<221> NAME/KEY: misc_feature
<222> LOCATION: (1)...(396)
<223> OTHER INFORMATION: n = A,T,C or G

<400> SEQUENCE: 77
ctgcagcccg ggggatccac taatctacca nggttatttg gcagctaatt ctanatttgg     60
atcattgccc aaagttgcac ttgctggtct cttgggattt ggccttggaa aggtatcata    120
catanganta tgccanaata aattccattt ttttgaaaat canctccntg gggctggttt    180
tggtccacag cataacangc actgcctcct tacctgtgag gaatgcaaaa taaagcatgg    240
attaagtgag aagggagact ctcagccttc agcttcctaa attctgtgtc tgtgactttc    300
gaagtttttt aaacctctga atttgtacac atttaaaatt tcaagtgtac tttaaaataa    360
aatacttcta atgggaacaa aaaaaaaaaa aaaaaa                              396

<210> SEQ ID NO 78
<211> LENGTH: 793
<212> TYPE: DNA
<213> ORGANISM: Homo sapien
<220> FEATURE:
```

<221> NAME/KEY: misc_feature
<222> LOCATION: (1)...(793)
<223> OTHER INFORMATION: n = A,T,C or G

<400> SEQUENCE: 78

```
gcatcctagc cgccgactca cacaaggcag gtgggtgagg aaatccagag ttgccatgga      60
gaaaattcca gtgtcagcat tcttgctcct tgtggccctc tcctacactc tggccagaga    120
taccacagtc aaacctggag ccaaaaagga cacaaaggac tctcgaccca aactgcccca    180
gaccctctcc agaggttggg gtgaccaact catctggact cagacatatg aagaagctct    240
atataaatcc aagacaagca acaaacccct gatgattatt catcacttgg atgagtgccc    300
acacagtcna gctttaaaga aagtgtttgc tgaaaataaa gaaatccaga aattggcaga    360
gcagtttgtc ctcctcaatc tggtttatga acaactgac aaacacctt tcctgatgg       420
ccagtatgtc ccaggattat gtttgttgac ccatctctga cagttgaagc cgatatcctg    480
ggaagatatt cnaaccgtct ctatgcttac aaactgcaga tacgctctgt tgcttgacac    540
atgaaaaagc tctcaagttg ctnaaaatga attgtaagaa aaaaaatctc cagccttctg    600
tctgtcggct tgaaaattga aaccagaaaa atgtgaaaaa tggctattgt ggaacanatn    660
gacacctgat taggttttgg ttatgttcac cactatttt aanaaaanan nttttaaaat      720
ttggttcaat tntcttttn aaacaatntg tttctacntt gnganctgat ttctaaaaaa    780
aataatnttt ggc                                                        793
```

<210> SEQ ID NO 79
<211> LENGTH: 456
<212> TYPE: DNA
<213> ORGANISM: Homo sapien
<220> FEATURE:
<221> NAME/KEY: misc_feature
<222> LOCATION: (1)...(456)
<223> OTHER INFORMATION: n = A,T,C or G

<400> SEQUENCE: 79

```
actagtatgg ggtgggaggc cccacccttc tccctaggc gctgttcttg ctccaaaggg       60
ctccgtggag agggactggc agagctgang ccacctgggg ctggggatcc cactcttctt    120
gcagctgttg agcgcaccta accactggtc atgcccccac ccctgctctc cgcacccgct    180
tcctcccgac cccangacca ggctacttct cccctcctct tgcctccctc ctgcccctgc    240
tgcctctgat cgtangaatt gangantgtc ccgccttgtg gctganaatg gacagtggca    300
ggggctggaa atgggtgtgt gtgtgtgtgt gtgtgtgtgt gtgtgtgtgt gcncccccc     360
tgcaagaccg agattgaggg aaancatgtc tgctgggtgt gaccatgttt cctctccata    420
aantnccct gtgacnctca naaaaaaaa aaaaaa                                456
```

<210> SEQ ID NO 80
<211> LENGTH: 284
<212> TYPE: DNA
<213> ORGANISM: Homo sapien
<220> FEATURE:
<221> NAME/KEY: misc_feature
<222> LOCATION: (1)...(284)
<223> OTHER INFORMATION: n = A,T,C or G

<400> SEQUENCE: 80

```
ctttgtacct ctagaaaaga taggtattgt gtcatgaaac ttgagtttaa atttatata      60
taaaactaaa agtaatgctc actttagcaa cacatactaa aattggaacc atactgagaa    120
gaatagcatg acctccgtgc aaacaggaca agcaaatttg tgatgtgttg attaaaaaga   180
```

```
aataaataaa tgtgtatatg tgtaacttgt atgtttatgt ggaatacaga ttgggaaata      240
aaatgtattt cttactgtga aaaaaaaaaa aaaaaaaaa aana                        284
```

<210> SEQ ID NO 81
<211> LENGTH: 671
<212> TYPE: DNA
<213> ORGANISM: Homo sapien
<220> FEATURE:
<221> NAME/KEY: misc_feature
<222> LOCATION: (1)...(671)
<223> OTHER INFORMATION: n = A,T,C or G

<400> SEQUENCE: 81

```
gccaccaaca ttccaagcta ccctgggtac ctttgtgcag tagaagctag tgagcatgtg      60
agcaagcggt gtgcacacgg agactcatcg ttataattta ctatctgcca agagtagaaa     120
gaaaggctgg ggatatttgg gttggcttgg ttttgatttt ttgcttgttt gtttgttttg     180
tactaaaaca gtattatctt ttgaatatcg tagggacata agtatataca tgttatccaa     240
tcaagatggc tagaatggtg cctttctgag tgtctaaaac ttgacacccc tggtaaatct     300
ttcaacacac ttccactgcc tgcgtaatga agttttgatt catttttaac cactggaatt     360
tttcaatgcc gtcattttca gttagatnat tttgcacttt gagattaaaa tgccatgtct     420
atttgattag tcttattttt ttatttttac aggcttatca gtctcactgt tggctgtcat     480
tgtgacaaag tcaaataaac ccccnaggac aacacacagt atgggatcac atattgtttg     540
acattaagct ttggccaaaa aatgttgcat gtgttttacc tcgacttgct aaatcaatan     600
canaaaggct ggctnataat gttggtggtg aaataattaa tnantaacca aaaaaaaaan     660
aaaaaaaaaa a                                                          671
```

<210> SEQ ID NO 82
<211> LENGTH: 217
<212> TYPE: DNA
<213> ORGANISM: Homo sapien
<220> FEATURE:
<221> NAME/KEY: misc_feature
<222> LOCATION: (1)...(217)
<223> OTHER INFORMATION: n = A,T,C or G

<400> SEQUENCE: 82

```
ctgcagatgt ttcttgaatg ctttgtcaaa ttaanaaagt taaagtgcaa taatgtttga      60
agacaataag tggtggtgta tcttgtttct aataagataa acttttttgt ctttgcttta     120
tcttattagg gagttgtatg tcagtgtata aaacatactg tgtggtataa caggcttaat     180
aaattcttta aaggaaaaa aaaaaaaaa aaaaaaa                                217
```

<210> SEQ ID NO 83
<211> LENGTH: 460
<212> TYPE: DNA
<213> ORGANISM: Homo sapien
<220> FEATURE:
<221> NAME/KEY: misc_feature
<222> LOCATION: (1)...(460)
<223> OTHER INFORMATION: n = A,T,C or G

<400> SEQUENCE: 83

```
cgcgagtggg agcaccagga tctcgggctc ggaacgagac tgcacggatt gttttaagaa      60
aatggcagac aaaccagaca tgggggaaat cgccagcttc gatnaggcca agctgaanaa     120
aacggagacg caggagaaga acaccctgcc gaccaaagag accattgagc angaagcg      180
```

```
gagtgaaatt tcctaagatc ctggaggatt tcctaccccc gtcctcttcg agacccagt    240 cgtgatgtgg aggaagagcc acctgcaaga tggacacgag ccacaagctg cactgtgaac   300
ctgggcactc cgcgccgatg ccaccggcct gtgggtctct gaagggaccc ccccaatcg    360 gactgccaaa ttctccggtt tgccccggga tattatacaa nattatttgt atgaataatg   420
annataaaac acacctcgtg gcancaaana aaaaaaaaa                          460
```

<210> SEQ ID NO 84
<211> LENGTH: 323
<212> TYPE: DNA
<213> ORGANISM: Homo sapien
<220> FEATURE:
<221> NAME/KEY: misc_feature
<222> LOCATION: (1)...(323)
<223> OTHER INFORMATION: n = A,T,C or G

<400> SEQUENCE: 84

```
tggtggatct tggctctgtg gagctgctgg gacgggatct aaaagactat tctggaagct    60
gtggtccaan gcattttgct ggcttaacgg gtcccggaac aaaggacacc agctctctaa   120
aattgaagtt tacccganat aacaatcttt tgggcagaga tgcctatttt aacaaacncc   180
gtccctgcgc aacaacnaac aatctctggg aaataccggc catgaacntg ctgtctcaat   240
cnancatctc tctagctgac cgatcatatc gtcccagatt actacanatc ataataattg   300
atttcctgta naaaaaaaaa aaa                                           323
```

<210> SEQ ID NO 85
<211> LENGTH: 771
<212> TYPE: DNA
<213> ORGANISM: Homo sapien
<220> FEATURE:
<221> NAME/KEY: misc_feature
<222> LOCATION: (1)...(771)
<223> OTHER INFORMATION: n = A,T,C or G

<400> SEQUENCE: 85

```
aaactgggta ctcaacactg agcagatctg ttctttgagc taaaaaccat gtgctgtacc    60
aanagtttgc tcctggctgc tttgatgtca gtgctgctac tccacctctg cggcgaatca   120
gaagcaagca actttgactg ctgtcttgga tacacagacc gtattcttca tcctaaattt   180
attgtgggct tcacacggca gctggccaat gaaggctgtg acatcaatgc tatcatcttt   240
cacacaaaga aaaagttgtc tgtgtgcgca aatccaaaac agacttgggt gaaatatatt   300
gtgcgtctcc tcagtaaaaa agtcaagaac atgtaaaaac tgtggctttt ctggaatgga   360
attggacata gcccaagaac agaaagaact tgctggggtt ggaggtttca cttgcacatc   420
atgganggtt tagtgcttat cttatttgtg cctcctggac ttgtccaatt natgaagtta   480
atcatattgc atcatantt gctttgttta acatcacatt naaattaaac tgtatttat    540 gttatttata gctntaggtt ttctgtgttt aacttttat acnaantttc ctaaactatt    600
ttggtntant gcaanttaaa aattatattt gggggggggaa taaatattgg antttctgca   660
gccacaagct tttttttaaaa aaccantaca nccnngttaa atggtnggtc ccnaatggtt   720 tttgctttt antagaaaat ttnttagaac natttgaaaa aaaaaaaaa a              771
```

<210> SEQ ID NO 86
<211> LENGTH: 628
<212> TYPE: DNA
<213> ORGANISM: Homo sapien
<220> FEATURE:
<221> NAME/KEY: misc_feature

```
<222> LOCATION: (1)...(628)
<223> OTHER INFORMATION: n = A,T,C or G

<400> SEQUENCE: 86
actagtttgc tttacatttt tgaaaagtat tattttttgtc caagtgctta tcaactaaac      60
cttgtgttag gtaagaatgg aatttattaa gtgaatcagt gtgacccttc ttgtcataag     120
attatcttaa agctgaagcc aaaatatgct tcaaaagaaa angactttat tgttcattgt     180
agttcataca ttcaaagcat ctgaactgta gtttctatag caagccaatt acatccataa     240
gtggagaang aaatagatta atgtcnaagt atgattggtg gagggagcaa ggttgaagat     300
aatctggggt tgaaattttc tagttttcat tctgtacatt tttagttnga catcagattt     360
gaaatattaa tgtttacctt tcaatgtgtg gtatcagctg gactcantaa cacccctttc     420
ttccctnggg gatggggaat ggattattgg aaaatggaaa gaaaaaagta cttaaagcct     480
tcctttcnca gtttctggct cctaccctac tgatttancc agaataagaa aacattttat     540
catcntctgc tttattccca ttaatnaant tttgatgaat aaatctgctt ttatgcnnac     600
ccaaggaatt nagtggnttc ntcnttgt                                        628

<210> SEQ ID NO 87
<211> LENGTH: 518
<212> TYPE: DNA
<213> ORGANISM: Homo sapien
<220> FEATURE:
<221> NAME/KEY: misc_feature
<222> LOCATION: (1)...(518)
<223> OTHER INFORMATION: n = A,T,C or G

<400> SEQUENCE: 87 tttttttattt ttttttagaga gtagttcagc ttttatttat aaatttattg cctgttttat     60
tataacaaca ttatactgtt tatggtttaa tacatatggt tcaaaatgta taatacatca    120
agtagtacag ttttaaaatt ttatgcttaa aacaagtttt gtgtaaaaaa tgcagataca    180
ttttacatgg caaatcaatt tttaagtcat cctaaaaatt gatttttttt tgaaatttaa    240
aaacacattt aatttcaatt tctctcttat ataaccttta ttactatagc atggtttcca    300
ctacagttta acaatgcagc aaaattccca tttcacggta aattgggttt taagcggcaa    360
ggttaaaatg ctttgaggat cctnaatacc ctttgaactt caaatgaagg ttatggttgt    420
naatttaacc ctcatgccat aagcagaagc acaagtttag ctgcattttg ctctaaactg    480
taaaancgag cccccgttg aaaaagcaaa agggaccc                             518

<210> SEQ ID NO 88
<211> LENGTH: 1844
<212> TYPE: DNA
<213> ORGANISM: Homo sapien

<400> SEQUENCE: 88
gagacagtga atcctagtat caaaggattt ttggcctcag aaaaagttgt tgattatttt      60
tattttatt tattttttcga gactccgtct caaaaaaaaa aaaaaaaaaa agaatcacaa    120
ggtatttgct aaagcatttt gagctgcttg gaaaaaggga agtagttgca gtagagtttc    180
ttccatcttc ttggtgctgg gaagccatat atgtgtcttt tactcaagct aaggggtata    240
agcttatgtg ttgaatttgc tacatctata tttcacatat tctcacaata agagaatttt    300
gaaatagaaa tatcatagaa catttaagaa agtttagtat aaataatatt ttgtgtgttt    360
taatccctt gaagggatct atccaaagaa aatatttac actgagctcc ttcctacacg    420
```

```
tctcagtaac agatcctgtg ttagtctttg aaaatagctc attttttaaa tgtcagtgag    480
tagatgtagc atacatatga tgtataatga cgtgtattat gttaacaatg tctgcagatt    540
ttgtaggaat acaaaacatg gccttttta taagcaaaac gggccaatga ctagaataac    600
acatagggca atctgtgaat atgtattata agcagcattc cagaaaagta gttggtgaaa    660
taattttcaa gtcaaaaagg gatatggaaa gggaattatg agtaacctct atttttaag    720 ccttgctttt aaattaaacg ctacagccat ttaagccttg aggataataa agcttgagag    780
taataatgtt aggttagcaa aggtttagat gtatcacttc atgcatgcta ccatgatagt    840
aatgcagctc ttcgagtcat ttctggtcat tcaagatatt cacccttttg cccatagaaa    900
gcaccctacc tcacctgctt actgacattg tcttagctga tcacaagatc attatcagcc    960
tccattattc cttactgtat ataaaataca gagttttata ttttcctttc ttcgtttttc   1020
accatattca aaacctaaat ttgttttttgc agatggaatg caaagtaatc aagtgttcgt   1080
gctttcacct agaagggtgt ggtcctgaag gaaagaggtc cctaaatatc ccccaccctg   1140
ggtgctcctc cttccctggt accctgacta ccagaagtca ggtgctagag cagctggaga   1200
agtgcagcag cctgtgcttc cacagatggg ggtgctgctg caacaaggct ttcaatgtgc   1260
ccatcttagg gggagaagct agatcctgtg cagcagcctg gtaagtcctg aggaggttcc   1320
attgctcttc ctgctgctgt cctttgcttc tcaacggggc tcgctctaca gtctagagca   1380
catgcagcta acttgtgcct ctgcttatgc atgagggtta aattaacaac cataaccttc   1440
atttgaagtt caaaggtgta ttcaggatcc tcaaagcatt ttaaccttgc cgcttaaaac   1500
ccaatttacc gtgaaatggg aattttgctg cattgttaaa ctgtagtgga aaccatgcta   1560
tagtaataaa ggttatataa gagagaaatt gaaattaaat gtgttttttaa atttcaaaaa   1620 aaaatcaatc tttaggatga cttaaaaatt gatttgccat gtaaaatgta tctgcatttt   1680
ttacacaaaa cttgttttaa gcataaaatt ttaaaactgt actacttgat gtattataca   1740
ttttgaacca tatgtattaa accataaaca gtataatgtt gttataataa aacaggcaat   1800
aaatttataa ataaaagctg aaaaaaaaaa aaaaaaaaa aaaa                     1844
```

<210> SEQ ID NO 89
<211> LENGTH: 523
<212> TYPE: DNA
<213> ORGANISM: Homo sapien
<220> FEATURE:
<221> NAME/KEY: misc_feature
<222> LOCATION: (1)...(523)
<223> OTHER INFORMATION: n = A,T,C or G

<400> SEQUENCE: 89

```
tttttttttt ttttttttagt caatccacat ttattgatca cttattatgt accaggcact     60
gggataaaga tgactgttag tcactcacag taaggaagaa aactagcaaa taagacgatt    120
acaatatgat gtagaaaatg ctaagccaga gatatagaaa ggtcctattg ggtccttctg    180
tcaccttgtc tttccacatc cctacccttc acaggccttc cctccagctt cctgcccccg    240
ctccccactg cagatcccct gggattttgc ctagagctaa acgagganat gggcccctg     300 gccctggcat gacttgaacc caaccacaga ctgggaaagg gagcctttcg anagtggatc    360
actttgatna gaaacacat agggaattga agagaaantc cccaaatggc cacccgtgct    420
ggtgctcaag aaaagtttgc agaatggata aatgaaggat caagggaatt aatanatgaa    480
taattgaatg gtggctcaat aagaatgact ncnttgaatg acc                      523
```

<210> SEQ ID NO 90
<211> LENGTH: 604
<212> TYPE: DNA
<213> ORGANISM: Homo sapien
<220> FEATURE:
<221> NAME/KEY: misc_feature
<222> LOCATION: (1)...(604)
<223> OTHER INFORMATION: n = A,T,C or G

<400> SEQUENCE: 90

| | | | | | | |
|---|---|---|---|---|---|---|
| ccagtgtggt | ggaatgcaaa | gattaccccg | gaagctttcg | agaagctggg | attccctgca | 60 |
| gcaaaggaaa | tagccaatat | gtgtcgtttc | tatgaaatga | agccagaccg | agatgtcaat | 120 |
| ctcacccacc | aactaaatcc | caaagtcaaa | agcttcagcc | agtttatctc | agagaaccag | 180 |
| gggagccttc | aagggcatgt | agaaaatcag | ctgttcagat | aggcctctgc | accacacagc | 240 |
| ctctttcctc | tctgatcctt | ttcctcttta | cggcacaaca | ttcatgtttg | acagaacatg | 300 |
| ctggaatgca | attgtttgca | acaccgaagg | atttcctgcg | gtcgcctctt | cagtaggaag | 360 |
| cactgcattg | gtgataggac | acggtaattt | gattcacatt | taacttgcta | gttagtgata | 420 |
| aggggtggta | cacctgtttg | gtaaaatgag | aagcctcgga | aacttgggag | cttctctcct | 480 |
| accactaatg | gggagggcag | attattactg | ggatttctcc | tggggtgaat | taatttcaag | 540 |
| ccctaattgc | tgaaattccc | ctnggcaggc | tccagttttc | tcaactgcat | tgcaaaattc | 600 |
| cccc | | | | | | 604 |

<210> SEQ ID NO 91
<211> LENGTH: 858
<212> TYPE: DNA
<213> ORGANISM: Homo sapien
<220> FEATURE:
<221> NAME/KEY: misc_feature
<222> LOCATION: (1)...(858)
<223> OTHER INFORMATION: n = A,T,C or G

<400> SEQUENCE: 91

| | | | | | | |
|---|---|---|---|---|---|---|
| tttttttttt | ttttttttta | tgattattat | ttttttttatt | gatctttaca | tcctcagtgt | 60 |
| tggcagagtt | tctgatgctt | aataaacatt | tgttctgatc | agataagtgg | aaaaaattgt | 120 |
| catttcctta | ttcaagccat | gcttttctgt | gatattctga | tcctagttga | acatacagaa | 180 |
| ataaatgtct | aaaacagcac | ctcgattctc | gtctataaca | ggactaagtt | cactgtgatc | 240 |
| ttaaataagc | ttggctaaaa | tgggacatga | gtggaggtag | tcacacttca | gcgaagaaag | 300 |
| agaatctcct | gtataatctc | accaggagat | tcaacgaatt | ccaccacact | ggactagtgg | 360 |
| atcccccggg | ctgcaggaat | tcgatatcaa | gcttatcgat | accgtcgacc | tcgaggggg | 420 |
| gcccggtacc | caattcgccc | tatagtgagt | cgtattacgc | gcgctcactg | gccgtcgttt | 480 |
| tacaacgtcg | tgactgggaa | aaccctggcg | ttacccaact | taatcgcctt | gcagcacatc | 540 |
| ccccttttcgc | cagctggcgt | aatagcgaan | agcccgcacc | gatcgccctt | ncaacagttg | 600 |
| cgcagcctga | atggcgaatg | ggacgcgccc | tgtagcggcg | cattaaagcg | cggcngggtg | 660 |
| tggnggntcc | cccacgtgac | cgntacactt | ggcagcgcct | tacgccggtc | nttcgctttc | 720 |
| ttcccttcct | ttctcgcacc | gttcgccggg | tttccccgnn | agctnttaat | cgggggnctc | 780 |
| cctttanggg | tncnaattaa | nggnttacng | gaccttngan | cccaaaaact | ttgattaggg | 840 |
| ggaaggtccc | cgaagggg | | | | | 858 |

<210> SEQ ID NO 92
<211> LENGTH: 585
<212> TYPE: DNA

```
<213> ORGANISM: Homo sapien
<220> FEATURE:
<221> NAME/KEY: misc_feature
<222> LOCATION: (1)...(585)
<223> OTHER INFORMATION: n = A,T,C or G

<400> SEQUENCE: 92
gttgaatctc ctggtgagat tatacaggag attctctttc ttcgctgaag tgtgactacc      60
tccactcatg tcccatttta gccaagctta tttaagatca cagtgaactt agtcctgtta     120
tagacgagaa tcgaggtgct gttttagaca tttatttctg tatgttcaac taggatcaga     180
atatcacaga aaagcatggc ttgaataagg aaatgacaat ttttccact tatctgatca      240
gaacaaatgt ttattaagca tcagaaactc tgccaacact gaggatgtaa agatcaataa     300
aaaaataat aatcatnann naananann nngaagggcg gccgccaccg cggtggagct       360
ccagcttttg ttccctttag tgagggttaa ttgcgcgctt ggcgttaatc atggtcatag     420
ctgtttcctg tgtgaaattg ttatccggct cacaattccn cncaacatac gagccgggaa     480
gcntnangtg taaaagcctg ggggtgccta attgagtgag ctnactcaca ttaattgngt     540
tgcgctccac ttgcccgctt ttccantccg ggaaacctgt tcgnc                    585

<210> SEQ ID NO 93
<211> LENGTH: 567
<212> TYPE: DNA
<213> ORGANISM: Homo sapien
<220> FEATURE:
<221> NAME/KEY: misc_feature
<222> LOCATION: (1)...(567)
<223> OTHER INFORMATION: n = A,T,C or G

<400> SEQUENCE: 93
cggcagtgtt gctgtctgcg tgtccacctt ggaatctggc tgaactggct gggaggacca      60
agactgcggc tggggtgggc anggaaggga accgggggct gctgtgaagg atcttggaac    120
ttccctgtac ccaccttccc cttgcttcat gtttgtanag gaaccttgtg ccggccaagc    180
ccagtttcct tgtgtgatac actaatgtat ttgctttttt tgggaaatan anaaaaatca    240
attaaattgc tantgtttct ttgaannnnn nnnnnnnnn nnnnnnnggg ggggncgccc     300
ccncggngga aacnccccct tttgttccct ttaattgaaa ggttaattng cncncntggc    360
gttaanccnt gggccaaanc tngttnccg tgntgaaatt gttatcccc tcccaaattc     420
cccccnncc ttccaaaccc ggaaanccta annntgttna ancccggggg gttgcctaan    480
ngnaattnaa ccnaaccccc ntttaaatng nntttgcncn ccacnngccc cnctttccca    540
nttcggggaa aaccctntcc gtgccca                                       567

<210> SEQ ID NO 94
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 94
actagtcaaa aatgctaaaa taatttggga gaaaatattt ttaagtagt gttatagttt      60
catgtttatc ttttattatg ttttgtgaag ttgtgtcttt tcactaatta cctatactat    120
gccaatattt cctatatatct atccataaca tttatactac atttgtaana naatatgcac   180
gtgaaactta acactttata aggtaaaaat gaggtttcca anatttaata atctgatcaa    240
```

-continued

```
gttcttgtta tttccaaata gaatggactt ggtctgttaa gggctaagga gaagaggaag      300
ataaggttaa aagttgttaa tgaccaaaca ttctaaaaga aatgcaaaaa aaaagtttat      360
tttcaagcct tcgaactatt taaggaaagc aaaatcattt cctaaatgca tatcatttgt      420
gagaatttct cattaatatc ctgaatcatt catttcacta aggctcatgt tnactccgat      480
atgtctctaa gaaagtacta tttcatggtc caaacctggt tgccatantt gggtaaaggc      540
tttcccttaa gtgtgaaant atttaaaatg aaattttcct cttttttaaaa attctttana    600 agggttaagg gtgttggga                                                  620
```

<210> SEQ ID NO 95
<211> LENGTH: 470
<212> TYPE: DNA
<213> ORGANISM: Homo sapien
<220> FEATURE:
<221> NAME/KEY: misc_feature
<222> LOCATION: (1)...(470)
<223> OTHER INFORMATION: n = A,T,C or G

<400> SEQUENCE: 95

```
ctcgaccttc tctgcacagc ggatgaaccc tgagcagctg aagaccagaa aagccactat     60
nactttntgc ttaattcang agcttacang attcttcaaa gagtgngtcc agcatccttt   120
gaaacatgag ttcttaccag cagaagcaga ccctttacccc accacctcag cttcaacagc  180
agcaggtgaa acaacccatc cagcctccac ctnaggaaat atttgttccc acaaccaagg   240
agccatgcca ctcaaaggtt ccacaacctg naaacaaaa nattccagag ccaggctgta    300
ccaaggtccc tgagccaggg ctgtaccaan gtccctgagc caggttgtac caangtccct   360
gagccaggat gtaccaaggt ccctgancca ggttgtccaa ggtccctgag ccaggctaca   420
ccaagggcct gngccaggca gcatcaangt ccctgaccaa ggcttatcaa                470
```

<210> SEQ ID NO 96
<211> LENGTH: 660
<212> TYPE: DNA
<213> ORGANISM: Homo sapien
<220> FEATURE:
<221> NAME/KEY: misc_feature
<222> LOCATION: (1)...(660)
<223> OTHER INFORMATION: n = A,T,C or G

<400> SEQUENCE: 96

```
tttttttttt ttttttttt ggaattaaaa gcaatttaat gagggcagag caggaaacat     60
gcatttcttt tcattcgaat cttcagatga accctgagca gccgaagacc agaaaagcca   120
tgaagacttt ctgcttaatt caggggctta caggattctt cagagtgtgt gtgaacaaaa   180
gctttatagt acgtattttt aggatacaaa taagagagag actatggctt ggggtgagaa   240
tgtactgatt acaaggtcta cagacaatta agacacagaa acagatggga agagggtgnc   300
cagcatctgg nggttggctt ctcaagggct tgtctgtgca ccaaattact tctgcttggn   360
cttctgctga gctgggcctg gagtgaccgt tgaaggacat ggctctggta cctttgtgta   420
gcctgncaca ggaactttgg tgtatccttg ctcaggaact ttgatggcac ctggctcagg  480
aaacttgatg aagccttggt caagggacct tgatgcttgc tggctcaggg acctggngn    540 ancctgggct canggacctt tgcncncaacc ttggcttcaa gggacccttg gnacatcctg   600
gcnnagggac ccttgggncc aaccctgggc ttnagggacc ctttggntnc nanccttggc    660
```

<210> SEQ ID NO 97

```
<211> LENGTH: 441
<212> TYPE: DNA
<213> ORGANISM: Homo sapien
<220> FEATURE:
<221> NAME/KEY: misc_feature
<222> LOCATION: (1)...(441)
<223> OTHER INFORMATION: n = A,T,C or G

<400> SEQUENCE: 97
gggaccatac anagtattcc tctcttcaca ccaggaccag ccactgttgc agcatgagtt      60
cccagcagca gaagcagccc tgcatcccac cccctcagct tcagcagcag caggtgaaac     120
agccttgcca gcctccacct caggaaccat gcatccccaa aaccaaggag ccctgccacc     180
ccaaggtgcc tgagccctgc caccccaaag tgcctgagcc ctgccagccc aaggttccag     240
agccatgcca ccccaaggtg cctgagccct gcccttcaat agtcactcca gcaccagccc     300
agcagaanac caagcagaag taatgtggtc cacagccatg cccttgagga gccggccacc     360
agatgctgaa tccctatcc cattctgtgt atgagtccca tttgccttgc aattagcatt     420
ctgtctcccc caaaaaaaaa a                                              441

<210> SEQ ID NO 98
<211> LENGTH: 600
<212> TYPE: DNA
<213> ORGANISM: Homo sapien
<220> FEATURE:
<221> NAME/KEY: misc_feature
<222> LOCATION: (1)...(600)
<223> OTHER INFORMATION: n = A,T,C or G

<400> SEQUENCE: 98
gtattcctct cttcacacca ggaccagcca ctgttgcagc atgagttccc agcagcagaa      60
gcagccctgc atcccacccc ctcagcttca gcagcagcag gtgaaacagc cttgccagcc     120
tccacctcag gaaccatgca tccccaaaac caaggagccc tgccacccca aggtgcctga     180
gccctgccac cccaaagtgc ctgagccctg ccagcccaag gttccagagc catgccaccc     240
caaggtgcct gagccctgcc ttcaatagt cactccagca ccagcccagc agaaaccaa     300 gcagaagtaa tgtggtccac agccatgccc ttgaggagcc ggccaccana tgctgaatcc     360
cctatcccat tctgtgtatg agtcccattt gccttgcaat tagcattctg tctcccccaa     420
aaaagaatgt gctatgaagc tttctttcct acacactctg agtctctgaa tgaagctgaa     480
ggtcttaant acaganctag ttttcagctg ctcagaattc tctgaagaaa agatttaaga     540
tgaaaggcaa atgattcagc tcctattac cccattaaat tcnctttcaa ttccaaaaaa     600

<210> SEQ ID NO 99
<211> LENGTH: 667
<212> TYPE: DNA
<213> ORGANISM: Homo sapien
<220> FEATURE:
<221> NAME/KEY: misc_feature
<222> LOCATION: (1)...(667)
<223> OTHER INFORMATION: n = A,T,C or G

<400> SEQUENCE: 99
actagtgact gagttcctgg caaagaaatt tgacctggac cagttgataa ctcatgtttt      60
accatttaaa aaaatcagtg aaggatttga gctgctcaat tcaggacaaa gcattcgaac     120
ggtcctgacg ttttgagatc caaagtggca ggaggtctgt gttgtcatgg tgaactggag     180
tttctcttgt gagagttccc tcatctgaaa tcatgtatct gtctcacaaa tacaagcata     240
agtagaagat tgttgaaga catagaaccc ttataaagaa ttattaacct ttataaacat     300
```

-continued

```
ttaaagtctt gtgagcacct gggaattagt ataataacaa tgttnatatt tttgatttac      360
attttgtaag gctataattg tatcttttaa gaaaacatac cttggatttc tatgttgaaa      420
tggagatttt taagagtttt aaccagctgc tgcagatata ttactcaaaa cagatatagc      480
gtataaagat atagtaaatg catctcctag agtaatattc acttaacaca ttggaaacta      540
ttatttttta gatttgaata tnaatgttat tttttaaaca cttgttatga gttacttggg      600
attacatttt gaaatcagtt cattccatga tgcanattac tgggattaga ttaagaaaga      660
cggaaaa                                                                667
```

<210> SEQ ID NO 100
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 100

```
gttttgtttg taagatgatc acagtcatgt tacactgatc taaaggacat atatataacc       60
ctttaaaaaa aaaatcactg cctcattctt atttcaagat gaatttctat acagactaga      120 tgttttctg aagatcaatt agacattttg aaaatgattt aaagtgtttt ccttaatgtt       180
ctctgaaaac aagtttcttt tgtagttttta accaaaaaag tgcccttttt gtcactggat      240
tctcctagca ttcatgattt ttttttcata caatgaaatt aaaattgcta aaatcatgga      300
ctggctttct ggttggattt caggtaagat gtgtttaagg ccagagcttt tctcagtatt      360 tgatttttt ccccaatatt tgatttttta aaaatataca catnggtgct gcatttatat      420
ctgctggttt aaaattctgt catatttcac ttctagcctt ttagttatgg caaatcatat      480 tttacttttta cttaaagcat ttggtnattt ggantatctg gttctannct aaaaaaanta      540
attctatnaa ttgaanttttt ggtactcnnc catatttgga tcc                       583
```

<210> SEQ ID NO 101
<211> LENGTH: 592
<212> TYPE: DNA
<213> ORGANISM: Homo sapien
<220> FEATURE:
<221> NAME/KEY: misc_feature
<222> LOCATION: (1)...(592)
<223> OTHER INFORMATION: n = A,T,C or G

<400> SEQUENCE: 101

```
gtggagacgt acaaagagca gccgctcaag acacctggga agaaaagaa aggcaagccc        60 gggaaacgca aggagcagga aaagaaaaaa cggcgaactc gctctgcctg gttagactct      120
ggagtgactg ggagtgggct agaaggggac cacctgtctg acacctccac aacgtcgctg      180
gagctcgatt cacggaggca ttgaaatttt cagcagganac cttccaagga catattgcag      240
gattctgtaa tagtgaacat atggaaagta ttagaaatat ttattgtctg taaatactgt      300
aaatgcattg gaataaaact gtctccccca ttgctctatg aaactgcaca ttggtcattg      360
tgaatatttt ttttttgcc aaggctaatc caattattat tatcacattt accataattt      420
attttgtcca ttgatgtatt tattttgtaa atgtatcttg gtgctgctga atttctatat      480 ttttgtaca atgcnttt anataacct atcaagtttg ttgataaatg acncaatgaa      540
gtgncncnan ttggnggttg aatttaatga atgcctaatt ttattatccc aa              592
```

<210> SEQ ID NO 102
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 102

| | | | | | |
|---|---|---|---|---|---|
| cgtcctaagc | acttagacta | catcagggaa | gaacacagac | cacatccctg | tcctcatgcg | 60 |
| gcttatgttt | tctggaagaa | agtggagacc | nagtccttgg | ctttagggct | ccccggctgg | 120 |
| gggctgtgca | ntccggtcag | ggcgggaagg | gaaatgcacc | gctgcatgtg | aacttacagc | 180 |
| ccaggcggat | gccccttccc | ttagcactac | ctggcctcct | gcatccctc | gcctcatgtt | 240 |
| cctcccacct | tcaaanaatg | aanaacccca | tgggcccagc | ccttgccct | ggggaaccaa | 300 |
| ggcagccttc | caaaactcag | gggctgaagc | anactattag | ggcaggggct | gactttgggt | 360 |
| gacactgccc | attccctctc | agggcagctc | angtcacccn | ggnctcttga | acccagcctg | 420 |
| ttcctttgaa | aaagggcaaa | actgaaaagg | gcttttccta | naaaaagaaa | aaccagggaa | 480 |
| ctttgccagg | gcttcnntnt | taccaaaacn | ncttctcnng | gattttaat | tccccattng | 540 |
| gcctccactt | accngggggcn | atgccccaaa | attaanaatt | tcccatc | | 587 |

<210> SEQ ID NO 103
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 103

| | | | | | |
|---|---|---|---|---|---|
| anaggactgg | ccctacntgc | tctctctcgt | cctacctatc | aatgcccaac | atggcagaac | 60 |
| ctgcanccct | tggncactgc | anatggaaac | ctctcagtgt | cttgacatca | ccctacccnt | 120 |
| gcggtgggtc | tccaccacaa | ccactttgac | tctgtggtcc | ctgnanggtg | gnttctcctg | 180 |
| actggcagga | tggaccttan | ccnacatatc | cctctgttcc | ctctgctnag | anaaagaatt | 240 |
| cccttaacat | gatataatcc | acccatgcaa | ntngctactg | gcccagctac | catttaccat | 300 |
| ttgcctacag | aatttcattc | agtctacact | ttggcattct | ctctggcgat | agagtgtggc | 360 |
| tgggctgacc | gcaaaaggtg | ccttacacac | tggcccccac | cctcaaccgt | tgacncatca | 420 |
| gangcttgcc | tcctccttct | gattnncccc | catgttggat | atcagggtgc | tcnagggatt | 480 |
| ggaaaagaaa | caaaac | | | | | 496 |

<210> SEQ ID NO 104
<211> LENGTH: 575
<212> TYPE: DNA
<213> ORGANISM: Homo sapien
<220> FEATURE:
<221> NAME/KEY: misc_feature
<222> LOCATION: (1)...(575)
<223> OTHER INFORMATION: n = A,T,C or G

<400> SEQUENCE: 104

| | | | | | |
|---|---|---|---|---|---|
| gcacctgctc | tcaatccnnc | tctcaccatg | atcctccgcc | tgcanaaact | cctctgccaa | 60 |
| ctatggangt | ggtttcnggg | gtggctcttg | ccaactggga | agaagccgtg | gtgtctctac | 120 |
| ctgttcaact | cngtttgtgt | ctgggggatc | aactngggggc | tatggaagcg | gctnaactgt | 180 |

-continued

```
tgttttggtg aagggctgg taattggctt tgggaagtng cttatngaag ttggcctngg    240
gaagttgcta ttgaaagtng ccntggaagt ngntttggtg gggggttttg ctggtggcct    300
ttgttnaatt tgggtgcttt gtnaatggcg gccccctcnc ctgggcaatg aaaaaaatca    360
ccnatgcngn aaacctcnac nnaacagcct gggcttccct cacctcgaaa aagttgctc     420 ccccccaaa aaaggncaan cccctcaann tggaangttg aaaaaatcct cgaatgggga     480
ncccnaaaac aaaaanccccc ccntttcccn gnaanggggg aaataccncc ccccactta    540 cnaaaccct tntaaaaaac ccccgggaa aaaa                                  575
```

<210> SEQ ID NO 105
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

<400> SEQUENCE: 105

```
cactagtagg atagaaacac tgtgtcccga gagtaaggag agaagctact attgattaga    60
gcctacccca ggttaactgc aagaagaggc gggatacttt cagcttttcca tgtaactgta   120 tgcataaagc caatgtagtc cagtttctaa gatcatgttc caagctaact gaatcccact    180
tcaatacaca ctcatgaact cctgatggaa caataacagg cccaagcctg tggtatgatg    240
tgcacacttg ctagactcan aaaaaatact actctcataa atgggtggga gtattttggt    300
gacaacctac tttgcttggc tgagtgaagg aatgatattc atatattcat ttattccatg    360
gacatttagt tagtgctttt tatataccag gcatgatgct gagtgacact cttgtgtata    420
tttccaaatt tttgtacagt cgctgcacat atttgaaatc atatattaag acttccaaaa    480
aatgaagtcc ctggtttttc atggcaactt gatcagtaaa ggattcncct ctgtttggta    540
cttaaaacat ctactatatn gttnanatga aattcctttt ccccnccctcc cgaaaaaana   600 aagtggtggg gaaaaaaaa                                                 619
```

<210> SEQ ID NO 106
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 106

```
cattggtnct ttcatttgct ntggaagtgt nnatctctaa cagtggacaa agttcccngt    60
gccttaaact ctgtnacact tttgggaant gaaaanttng tantatgata ggttattctg   120
angtanagat gttctggata ccattanatn tgccccccngt gtcagaggct catattgtgt   180
tatgtaaatg gtatntcatt cgctactatn antcaattg aaatanggtc tttgggttat    240
gaatantnng cagcncanct nanangctgt ctgtngtatt cattgtggtc atagcacctc    300
acancattgt aacctcnatc nagtgagaca nactagnaan ttcctagtga tggctcanga   360
ttccaaatgg nctcatntcn aatgtttaaa agttanttaa gtgtaagaaa tacagactgg    420
atgttccacc aactagtacc tgtaatgacn ggcctgtccc aacacatctc ccttttccat    480
gactgtggta ncccgcatcg gaaaaa                                         506
```

<210> SEQ ID NO 107
<211> LENGTH: 452
<212> TYPE: DNA
<213> ORGANISM: Homo sapien
<220> FEATURE:
<221> NAME/KEY: misc_feature
<222> LOCATION: (1)...(452)
<223> OTHER INFORMATION: n = A,T,C or G

<400> SEQUENCE: 107

| | | | | | |
|---|---|---|---|---|---|
| gttgagtctg | tactaaacag | taagatatct | caatgaacca | taaattcaac | tttgtaaaaa | 60 |
| tctttttgaag | catagataat | attgtttggt | aaatgtttct | tttgtttggt | aaatgtttct | 120 |
| tttaaagacc | ctcctattct | ataaaactct | gcatgtagag | gcttgtttac | ctttctctct | 180 |
| ctaaggttta | caataggagt | ggtgatttga | aaaatataaa | attatgagat | tggttttcct | 240 |
| gtggcataaa | ttgcatcact | gtatcatttt | cttttttaac | cggtaagant | ttcagtttgt | 300 |
| tggaaagtaa | ctgtganaac | ccagtttccc | gtccatctcc | cttagggact | acccatagaa | 360 |
| catgaaaagg | tccccacnga | agcaagaaga | taagtctttc | atggctgctg | gttgcttaaa | 420 |
| ccactttaaa | accaaaaaat | tccccttgga | aa | | | 452 |

<210> SEQ ID NO 108
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 108

| | | | | | |
|---|---|---|---|---|---|
| atcttcttcc | cttaattagt | tnttatttat | ntattaaatt | ttattgcatg | tcctggcaaa | 60 |
| caaaaagaga | ttgtagattg | gcttctggct | ccccaaaagc | cataacaga | aagtaccaca | 120 |
| agaccncaac | tgaagcttaa | aaaatctatc | acatgtataa | tacctttnga | agaacattaa | 180 |
| tanagcatat | aaaacttttta | acatntgctt | aatgttgtnc | aattataaaa | ntaatngaaa | 240 |
| aaaatgtccc | tttaacatnc | aatatcccac | atagtgttat | ttnaggggat | taccnngnaa | 300 |
| naaaaaaagg | gtagaaggga | tttaatgaaa | actctgctnn | ccatttctgt | ttanaaacgt | 360 |
| ctccagaaca | aaaacttntc | aantctttca | gctaaccgca | tttgagctna | ggccactcaa | 420 |
| aaactccatt | agncccactt | tctaanggtc | tctanagctt | actaanccttt | ttgaccccttt | 480 |
| accctggnta | ctcctgccct | ca | | | | 502 |

<210> SEQ ID NO 109
<211> LENGTH: 1308
<212> TYPE: DNA
<213> ORGANISM: Homo sapien

<400> SEQUENCE: 109

| | | | | | |
|---|---|---|---|---|---|
| acccgaggtc | tcgctaaaat | catcatggat | tcacttggcg | ccgtcagcac | tcgacttggg | 60 |
| tttgatcttt | tcaaagagct | gaagaaaaca | atgatggca | acatcttctt | ttcccctgtg | 120 |
| ggcatcttga | ctgcaattgg | catggtcctc | ctggggaccc | gaggagccac | cgcttcccag | 180 |
| ttggaggagg | tgtttcactc | tgaaaaagag | acgaagagct | caagaataaa | ggctgaagaa | 240 |
| aaagaggtga | ttgagaacac | agaagcagta | catcaacaat | tccaaaagtt | tttgactgaa | 300 |
| ataagcaaac | tcactaatga | ttatgaactg | aacataacca | acaggctgtt | tggagaaaaa | 360 |
| acatacctct | tccttcaaaa | atacttagat | tatgttgaaa | aatattatca | tgcatctctg | 420 |

-continued

```
gaacctgttg attttgtaaa tgcagccgat gaaagtcgaa agaagattaa ttcctgggtt      480
gaaagcaaaa caaatgaaaa aatcaaggac ttgttcccag atggctctat tagtagctct      540
accaagctgg tgctggtgaa catggtttat tttaaagggc aatgggacag ggagtttaag      600
aaagaaaata ctaaggaaga gaattttggg atgaataaga gcacaagtaa atctgtacag      660
atgatgacac agagccattc ctttagcttc actttcctgg aggacttgca ggccaaaatt      720
ctagggattc catataaaaa caacgaccta agcatgtttg tgcttctgcc caacgacatc      780
gatggcctgg agaagataat agataaaata agtcctgaga aattggtaga gtggactagt      840
ccagggcata tggaagaaag aaaggtgaat ctgcacttgc cccggtttga ggtggaggac      900
agttacgatc tagaggcggt cctggctgcc atggggatgg gcgatgcctt cagtgagcac      960
aaagccgact actcgggaat gtcgtcaggc tccggttgt acgcccagaa gttcctgcac     1020
agttcctttg tggcagtaac tgaggaaggc accgaggctg cagctgccac tggcataggc     1080
tttactgtca catccgcccc aggtcatgaa atgttcact gcaatcatcc cttcctgttc      1140
ttcatcaggc acaatgaatc caacagcatc ctcttcttcg gcagattttc ttctccttaa     1200
gatgatcgtt gccatggcat tgctgctttt agcaaaaaac aactaccagt gttactcata     1260
tgattatgaa aatcgtccat tcttttaaat ggtggctcac ttgcattt                  1308
```

<210> SEQ ID NO 110
<211> LENGTH: 391
<212> TYPE: PRT
<213> ORGANISM: Homo sapien

<400> SEQUENCE: 110

```
Met Asp Ser Leu Gly Ala Val Ser Thr Arg Leu Gly Phe Asp Leu Phe
  1               5                  10                  15

Lys Glu Leu Lys Lys Thr Asn Asp Gly Asn Ile Phe Phe Ser Pro Val
             20                  25                  30

Gly Ile Leu Thr Ala Ile Gly Met Val Leu Leu Gly Thr Arg Gly Ala
         35                  40                  45

Thr Ala Ser Gln Leu Glu Glu Val Phe His Ser Glu Lys Glu Thr Lys
     50                  55                  60

Ser Ser Arg Ile Lys Ala Glu Glu Lys Glu Val Ile Glu Asn Thr Glu
 65                  70                  75                  80

Ala Val His Gln Gln Phe Gln Lys Phe Leu Thr Glu Ile Ser Lys Leu
                 85                  90                  95

Thr Asn Asp Tyr Glu Leu Asn Ile Thr Asn Arg Leu Phe Gly Glu Lys
            100                 105                 110

Thr Tyr Leu Phe Leu Gln Lys Tyr Leu Asp Tyr Val Glu Lys Tyr Tyr
        115                 120                 125

His Ala Ser Leu Glu Pro Val Asp Phe Val Asn Ala Ala Asp Glu Ser
    130                 135                 140

Arg Lys Lys Ile Asn Ser Trp Val Glu Ser Lys Thr Asn Glu Lys Ile
145                 150                 155                 160

Lys Asp Leu Phe Pro Asp Gly Ser Ile Ser Ser Thr Lys Leu Val
                165                 170                 175

Leu Val Asn Met Val Tyr Phe Lys Gly Gln Trp Asp Arg Glu Phe Lys
            180                 185                 190

Lys Glu Asn Thr Lys Glu Glu Lys Phe Trp Met Asn Lys Ser Thr Ser
        195                 200                 205

Lys Ser Val Gln Met Met Thr Gln Ser His Ser Phe Ser Phe Thr Phe
```

```
              210                 215                 220
Leu Glu Asp Leu Gln Ala Lys Ile Leu Gly Ile Pro Tyr Lys Asn Asn
225                 230                 235                 240

Asp Leu Ser Met Phe Val Leu Leu Pro Asn Asp Ile Asp Gly Leu Glu
                245                 250                 255

Lys Ile Ile Asp Lys Ile Ser Pro Glu Lys Leu Val Glu Trp Thr Ser
                260                 265                 270

Pro Gly His Met Glu Glu Arg Lys Val Asn Leu His Leu Pro Arg Phe
            275                 280                 285

Glu Val Glu Asp Ser Tyr Asp Leu Glu Ala Val Leu Ala Ala Met Gly
        290                 295                 300

Met Gly Asp Ala Phe Ser Glu His Lys Ala Asp Tyr Ser Gly Met Ser
305                 310                 315                 320

Ser Gly Ser Gly Leu Tyr Ala Gln Lys Phe Leu His Ser Ser Phe Val
                325                 330                 335

Ala Val Thr Glu Gly Thr Glu Ala Ala Ala Thr Gly Ile Gly
                340                 345                 350

Phe Thr Val Thr Ser Ala Pro Gly His Glu Asn Val His Cys Asn His
            355                 360                 365

Pro Phe Leu Phe Phe Ile Arg His Asn Glu Ser Asn Ser Ile Leu Phe
        370                 375                 380

Phe Gly Arg Phe Ser Ser Pro
385                 390

<210> SEQ ID NO 111
<211> LENGTH: 1419
<212> TYPE: DNA
<213> ORGANISM: Homo sapien

<400> SEQUENCE: 111
ggagaactat aaattaagga tcccagctac ttaattgact tatgcttcct agttcgttgc      60
ccagccacca ccgtctctcc aaaaacccga ggtctcgcta aaatcatcat ggattcactt     120
ggcgccgtca gcactcgact tgggtttgat cttttcaaag agctgaagaa acaaatgat     180
ggcaacatct tcttttcccc tgtgggcatc ttgactgcaa ttggcatggt cctcctgggg     240
acccgaggag ccaccgcttc ccagttggag gaggtgtttc actctgaaaa agagacgaag     300
agctcaagaa taaaggctga agaaaaagag gtggtaagaa taaaggctga aggaaaagag     360
attgagaaca cagaagcagt acatcaacaa ttccaaaagt ttttgactga ataagcaaa     420
ctcactaatg attatgaact gaacataacc aacaggctgt ttggagaaaa aacataccte     480
ttccttcaaa aatacttaga ttatgttgaa aaatattatc atgcatctct ggaacctgtt     540
gattttgtaa atgcagccga tgaaagtcga agaagatta ttcctgggt tgaaagcaaa     600
acaaatgaaa aaatcaagga cttgttccca gatggctcta ttagtagctc taccaagctg     660
gtgctggtga acatggttta ttttaaaggg caatgggaca gggagtttaa gaaagaaaat     720
actaaggaag agaaattttg gatgaataag agcacaagta atctgtaca gatgatgaca     780
cagagccatt cctttagctt cactttcctg gaggacttgc aggccaaaat tctagggatt     840
ccatataaa acaacgacct aagcatgttt gtgcttctgc caacgacat cgatggcctg     900
gagaagataa tagataaaat aagtcctgag aaattggtag agtggactag tccagggcat     960
atggaagaaa gaaaggtgaa tctgcacttg cccggtttg aggtgggga cagttacgat    1020
ctagaggcgg tcctggctgc catggggatg ggcgatgcct tcagtgagca caaagccgac    1080
```

-continued

```
tactcgggaa tgtcgtcagg ctccggggttg tacgcccaga agttcctgca cagttccttt    1140
gtggcagtaa ctgaggaagg caccgaggct gcagctgcca ctggcatagg ctttactgtc    1200
acatccgccc caggtcatga aaatgttcac tgcaatcatc ccttcctgtt cttcatcagg    1260
cacaatgaat ccaacagcat cctcttcttc ggcagatttt cttctcctta agatgatcgt    1320
tgccatggca ttgctgcttt tagcaaaaaa caactaccag tgttactcat atgattatga    1380
aaatcgtcca ttcttttaaa tggtggctca cttgcattt                            1419
```

<210> SEQ ID NO 112
<211> LENGTH: 400
<212> TYPE: PRT
<213> ORGANISM: Homo sapien

<400> SEQUENCE: 112

```
Met Asp Ser Leu Gly Ala Val Ser Thr Arg Leu Gly Phe Asp Leu Phe
  1               5                  10                  15

Lys Glu Leu Lys Lys Thr Asn Asp Gly Asn Ile Phe Phe Ser Pro Val
             20                  25                  30

Gly Ile Leu Thr Ala Ile Gly Met Val Leu Leu Gly Thr Arg Gly Ala
         35                  40                  45

Thr Ala Ser Gln Leu Glu Glu Val Phe His Ser Glu Lys Glu Thr Lys
     50                  55                  60

Ser Ser Arg Ile Lys Ala Glu Glu Lys Glu Val Val Arg Ile Lys Ala
 65                  70                  75                  80

Glu Gly Lys Glu Ile Glu Asn Thr Glu Ala Val His Gln Gln Phe Gln
                 85                  90                  95

Lys Phe Leu Thr Glu Ile Ser Lys Leu Thr Asn Asp Tyr Glu Leu Asn
            100                 105                 110

Ile Thr Asn Arg Leu Phe Gly Glu Lys Thr Tyr Leu Phe Leu Gln Lys
        115                 120                 125

Tyr Leu Asp Tyr Val Glu Lys Tyr Tyr His Ala Ser Leu Glu Pro Val
    130                 135                 140

Asp Phe Val Asn Ala Ala Asp Glu Ser Arg Lys Lys Ile Asn Ser Trp
145                 150                 155                 160

Val Glu Ser Lys Thr Asn Glu Lys Ile Lys Asp Leu Phe Pro Asp Gly
                165                 170                 175

Ser Ile Ser Ser Thr Lys Leu Val Leu Val Asn Met Val Tyr Phe
            180                 185                 190

Lys Gly Gln Trp Asp Arg Glu Phe Lys Lys Glu Asn Thr Lys Glu Glu
        195                 200                 205

Lys Phe Trp Met Asn Lys Ser Thr Ser Lys Ser Val Gln Met Met Thr
    210                 215                 220

Gln Ser His Ser Phe Ser Phe Thr Phe Leu Glu Asp Leu Gln Ala Lys
225                 230                 235                 240

Ile Leu Gly Ile Pro Tyr Lys Asn Asn Asp Leu Ser Met Phe Val Leu
                245                 250                 255

Leu Pro Asn Asp Ile Asp Gly Leu Glu Lys Ile Ile Asp Lys Ile Ser
            260                 265                 270

Pro Glu Lys Leu Val Glu Trp Thr Ser Pro Gly His Met Glu Glu Arg
        275                 280                 285

Lys Val Asn Leu His Leu Pro Arg Phe Glu Val Glu Asp Ser Tyr Asp
    290                 295                 300

Leu Glu Ala Val Leu Ala Ala Met Gly Met Gly Asp Ala Phe Ser Glu
305                 310                 315                 320
```

His Lys Ala Asp Tyr Ser Gly Met Ser Ser Gly Ser Gly Leu Tyr Ala
            325                 330                 335

Gln Lys Phe Leu His Ser Ser Phe Val Ala Val Thr Glu Glu Gly Thr
            340                 345                 350

Glu Ala Ala Ala Ala Thr Gly Ile Gly Phe Thr Val Thr Ser Ala Pro
            355                 360                 365

Gly His Glu Asn Val His Cys Asn His Pro Phe Leu Phe Phe Ile Arg
        370                 375                 380

His Asn Glu Ser Asn Ser Ile Leu Phe Phe Gly Arg Phe Ser Ser Pro
385                 390                 395                 400

<210> SEQ ID NO 113
<211> LENGTH: 957
<212> TYPE: DNA
<213> ORGANISM: Homo sapien

<400> SEQUENCE: 113

```
ctcgaccttc tctgcacagc ggatgaaccc tgagcagctg aagaccagaa aagccactat     60
gactttctgc ttaattcagg agcttacagg attcttcaaa gagtgtgtcc agcatccttt    120
gaaacatgag ttcttaccag cagaagcaga cctttacccc accacctcag cttcaacagc    180
agcaggtgaa acaacccagc cagcctccac ctcaggaaat atttgttccc acaaccaagg    240
agccatgcca ctcaaaggtt ccacaacctg aaacacaaa gattccagag ccaggctgta    300
ccaaggtccc tgagccaggc tgtaccaagg tccctgagcc aggttgtacc aaggtccctg    360
agccaggatg taccaaggtc cctgagccag gttgtaccaa ggtccctgag ccaggctaca    420
ccaaggtccc tgagccaggc agcatcaagg tccctgacca aggcttcatc aagtttcctg    480
agccaggtgc catcaaagtt cctgagcaag gatacaccaa agttcctgtg ccaggctaca    540
caaaggtacc agagccatgt ccttcaacgg tcactccagg cccagctcag cagaagacca    600
agcagaagta atttggtgca cagacaagcc cttgagaagc caaccaccag atgctggaca    660
ccctcttccc atctgttcct gtgtcttaat tgtctgtaga ccttgtaatc agtacattct    720
caccccaagc catagtctct ctcttatttg tatcctaaaa atacggtact ataaagcttt    780
tgttcacaca cactctgaag aatcctgtaa gcccctgaat taagcagaaa gtcttcatgg    840
cttttctggt cttcggctgc tcagggttca tctgaagatt cgaatgaaaa gaaatgcatg    900
tttcctgctc tgccctcatt aaattgcttt taattccaaa aaaaaaaaaa aaaaaaa      957
```

<210> SEQ ID NO 114
<211> LENGTH: 161
<212> TYPE: PRT
<213> ORGANISM: Homo sapien

<400> SEQUENCE: 114

Met Ser Ser Tyr Gln Gln Lys Gln Thr Phe Thr Pro Pro Gln Leu
1               5                   10                  15

Gln Gln Gln Gln Val Lys Gln Pro Ser Gln Pro Pro Gln Glu Ile
            20                  25                  30

Phe Val Pro Thr Thr Lys Glu Pro Cys His Ser Lys Val Pro Gln Pro
        35                  40                  45

Gly Asn Thr Lys Ile Pro Glu Pro Gly Cys Thr Lys Val Pro Glu Pro
        50                  55                  60

Gly Cys Thr Lys Val Pro Glu Pro Gly Cys Thr Lys Val Pro Glu Pro
65                  70                  75                  80

```
Gly Cys Thr Lys Val Pro Glu Pro Gly Cys Thr Lys Val Pro Glu Pro
                85                  90                  95
Gly Tyr Thr Lys Val Pro Glu Pro Gly Ser Ile Lys Val Pro Asp Gln
            100                 105                 110
Gly Phe Ile Lys Phe Pro Glu Pro Gly Ala Ile Lys Val Pro Glu Gln
        115                 120                 125
Gly Tyr Thr Lys Val Pro Val Pro Gly Tyr Thr Lys Val Pro Glu Pro
    130                 135                 140
Cys Pro Ser Thr Val Thr Pro Gly Pro Ala Gln Gln Lys Thr Lys Gln
145                 150                 155                 160
Lys

<210> SEQ ID NO 115
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 115
cattggtnct ttcatttgct ntggaagtgt nnatctctaa cagtggacaa agttcccngt      60
gccttaaact ctgtnacact tttgggaant gaaaanttng tantatgata ggttattctg     120
angtanagat gttctggata ccattanatn tgccccngt gtcagaggct catattgtgt      180
tatgtaaatg gtatntcatt cgctactatn antcaattng aaatanggtc tttgggttat    240
gaatantnng cagcncanct nanangctgt ctgtngtatt cattgtggtc atagcacctc    300
acancattgt aacctcnatc nagtgagaca nactagnaan ttcctagtga tggctcanga    360
ttccaaatgg nctcatntcn aatgtttaaa agttanttaa gtgtaagaaa tacagactgg    420
atgttccacc aactagtacc tgtaatgacn ggcctgtccc aacacatctc cctttccat    480 gactgtggta ncccgcatcg gaaaaa                                         506

<210> SEQ ID NO 116

<211> LENGTH: 3079
<212> TYPE: DNA
<213> ORGANISM: Homo sapien

<400> SEQUENCE: 116
ggatccccgg gtttcctaaa cccccacag agtcctgccc aggccaaaga gcaaggaaaa      60
ggtcaaaggg cagaaaaaat gctgagttag gaggagctat ggaaggataa acctggcctt    120
aaagaggtca aagtggttta tagggggcgc tgagggcttc ccacattctc tggcctaaac    180
cttgcaggca gatctgccca gtgggctctg ggatagctgt gccttcccta acaaaaaat     240 tgtgcacaaa aggatgaaac tctatttcc ctctagcaca taaccaagaa tataaggcta     300
cagattgcct ttcccagagg gaaaccctg cagcaacctg ctgcctggaa agtgtaaga     360 gcagatcact ggggaatcgt ttgccccccg ctgatggaca gcttcccaa gctccaaggg    420 caggtgctca gcatgtaccg tactgggatg gttgtcaata ctcctggtcc tgtaagagtc    480
ccaggacact gccatgccaa tgcccccctca gttcctggca tccttttgg gctgctcaca    540 gccccagcct ctatggtgaa gacatacttg ctagcagcgt caccaacttg ttgccaagag    600
atcagtgctc gaaggcaagg ttatttctaa ctgagcagag cctgccagga agaaagcgtt    660
tgcaccccac accactgtgc aggtgtgacc ggtgagctca cagctgcccc ccaggcatgc    720
```

-continued

| | |
|---|---|
| ccagcccact taatcatcac agctcgacag ctctctcgcc cagcccagtt ctggaaggga | 780 |
| taaaaggggg catcaccgtt cctgggtaac agagccacct tctgcgtcct gctgagctct | 840 |
| gttctctcca gcacctccca acccactagt gcctggttct cttgctccac caggaacaag | 900 |
| ccaccatgtc tcgccagtca agtgtgtctt ccggagcggg gggcagtcgt agcttcagca | 960 |
| ccgcctctgc catcaccccg tctgtctccc gcaccagctt cacctccgtg tcccggtccg | 1020 |
| ggggtggcgg tggtggtggc ttcggcaggg tcagccttgc gggtgcttgt ggagtgggtg | 1080 |
| gctatggcag ccggagcctc tacaacctgg ggggctccaa gaggatatcc atcagcacta | 1140 |
| gtggtggcag cttcaggaac cggtttggtg ctggtgctgg aggcggctat ggctttggag | 1200 |
| gtggtgccgg tagtggattt ggtttcggcg gtggagctgg tggtggcttt gggctcggtg | 1260 |
| gcggagctgg cttttggaggt ggcttcggtg gccctggctt tcctgtctgc cctcctggag | 1320 |
| gtatccaaga ggtcactgtc aaccagagtc tcctgactcc cctcaacctg caaatcgacc | 1380 |
| ccagcatcca gagggtgagg accgaggagc gcgagcagat caagaccctc aacaataagt | 1440 |
| ttgcctcctt catcgacaag gtgcggttcc tggagcagca gaacaaggtt ctggaaacaa | 1500 |
| agtggaccct gctgcaggag cagggcacca agactgtgag gcagaacctg gagccgttgt | 1560 |
| tcgagcagta catcaacaac ctcaggaggc agctggacag catcgtgggg gaacggggcc | 1620 |
| gcctggactc agagctgaga aacatgcagg acctggtgga agacttcaag aacaagtatg | 1680 |
| aggatgaaat caacaagcgt accactgctg agaatgagtt tgtgatgctg aagaaggatg | 1740 |
| tagatgctgc ctacatgaac aaggtggagc tggaggccaa ggttgatgca ctgatggatg | 1800 |
| agattaactt catgaagatg ttctttgatg cggagctgtc ccagatgcag acgcatgtct | 1860 |
| ctgacaccct cagtggtcct ccatggaca acaaccgcaa cctggacctg gatagcatca | 1920 |
| tcgctgaggt caaggcccag tatgaggaga ttgccaaccg cagccggaca gaagccgagt | 1980 |
| cctggtatca gaccaagtat gaggagctgc agcagacagc tggccggcat ggcgatgacc | 2040 |
| tccgcaacac caagcatgag atctctgaga tgaaccggat gatccagagg ctgagagccg | 2100 |
| agattgacaa tgtcaagaaa cagtgcgcca atctgcagaa cgccattgcg gatgccgagc | 2160 |
| agcgtgggga gctggccctc aaggatgcca ggaacaagct ggccgagctg gaggaggccc | 2220 |
| tgcagaaggc caagcaggac atggcccggc tgctgcgtga gtaccaggag ctcatgaaca | 2280 |
| ccaagctggc cctggacgtg gagatcgcca cttaccgcaa gctgctggag ggcgaggaat | 2340 |
| gcagactcag tggagaagga gttggaccag tcaacatctc tgttgtcaca agcagtgttt | 2400 |
| cctctggata tggcagtggc agtggctatg gcggtggcct cggtggaggt cttggcggcg | 2460 |
| gcctcggtgg aggtcttgcc ggaggtagca gtggaagcta ctactccagc agcagtgggg | 2520 |
| gtgtcggcct aggtggtggg ctcagtgtgg ggggctctgg cttcagtgca agcagtagcc | 2580 |
| gagggctggg ggtgggcttt ggcagtgcg ggggtagcag ctccagcgtc aaatttgtct | 2640 |
| ccaccacctc ctcctcccgg aagagcttca agagctaaga acctgctgca agtcactgcc | 2700 |
| ttccaagtgc agcaacccag cccatggaga ttgcctcttc taggcagttg ctcaagccat | 2760 |
| gttttatcct tttctggaga gtagtctaga ccaagccaat tgcagaacca cattctttgg | 2820 |
| ttccaggag agcccattc ccagccctg gtctcccgtg ccgcagttct atattctgct | 2880 |
| tcaaatcagc cttcaggttt cccacagcat ggccctgct gacacgagaa cccaaagttt | 2940 |
| tcccaaatct aaatcatcaa aacagaatcc ccaccccaat cccaattttt gttttggttc | 3000 |
| taactacctc cagaatgtgt tcaataaaat gttttataat ataagctggt gtgcagaatt | 3060 |

-continued

| | |
|---|---|
| gtttttttttt tctacccaa | 3079 |

<210> SEQ ID NO 117
<211> LENGTH: 6921
<212> TYPE: DNA
<213> ORGANISM: Homo sapien

<400> SEQUENCE: 117

| | |
|---|---|
| gaattctgac tgtccactca aaacttctat tccgatcaaa gctatctgtg actacagaca | 60 |
| aattgagata accatttaca aagacgatga atgtgttttg gcgaataact ctcatcgtgc | 120 |
| taaatggaag gtcattagtc ctactgggaa tgaggctatg gtcccatctg tgtgcttcac | 180 |
| cgttcctcca ccaaacaaag aagcggtgga ccttgccaac agaattgagc aacagtatca | 240 |
| gaatgtcctg actctttggc atgagtctca cataaacatg aagagtgtag tatcctggca | 300 |
| ttatctcatc aatgaaattg atagaattcg agctagcaat gtggcttcaa taaagacaat | 360 |
| gctacctggt gaacatcagc aagttctaag taatctacaa tctcgttttg aagattttct | 420 |
| ggaagatagc caggaatccc aagtcttttc aggctcagat ataacacaac tggaaaagga | 480 |
| ggttaatgta tgtaagcagt attatcaaga acttcttaaa tctgcagaaa gagaggagca | 540 |
| agaggaatca gtttataatc tctacatctc tgaagttcga acattagac ttcggttaga | 600 |
| gaactgtgaa gatcggctga ttagacagat tcgaactccc ctggaaagag atgatttgca | 660 |
| tgaaagtgtg ttcagaatca cagaacagga gaaactaaag aaagagctgg aacgacttaa | 720 |
| agatgatttg ggaacaatca caaataagtg tgaggagttt ttcagtcaag cagcagcctc | 780 |
| ttcatcagtc cctaccctac gatcagagct taatgtggtc cttcagaaca tgaaccaagt | 840 |
| ctattctatg tcttccactt acatagataa gttgaaaact gttaacttgg tgttaaaaaa | 900 |
| cactcaagct gcagaagccc tcgtaaaact ctatgaaact aaactgtgtg aagaagaagc | 960 |
| agttatagct gacaagaata atattgagaa tctaataagt actttaaagc aatggagatc | 1020 |
| tgaagtagat gaaaagagac aggtattcca tgccttagag gatgagttgc agaaagctaa | 1080 |
| agccatcagt gatgaaatgt ttaaaacgta taaagaacgg gaccttgatt ttgactggca | 1140 |
| caaagaaaaa gcagatcaat tagttgaaag gtggcaaaat gttcatgtgc agattgacaa | 1200 |
| caggttacgg gacttagagg gcattggcaa atcactgaag tactacagag cacttacca | 1260 |
| tcctttagat gattggatcc agcaggttga aactactcag agaaagattc aggaaaatca | 1320 |
| gcctgaaaat agtaaaaccc tagccacaca gttgaatcaa cagaagatgc tggtgtccga | 1380 |
| aatagaaatg aaacagagca aaatggacga gtgtcaaaaa tatgcagaac agtactcagc | 1440 |
| tacagtgaag gactatgaat acaaacaat gacctaccgg gccatggtag attcacaaca | 1500 |
| aaaatctcca gtgaaacgcc gaagaatgca gagttcagca gatctcatta ttcaagagtt | 1560 |
| catggaccta aggactcgat atactgccct ggtcactctc atgacacaat atattaaatt | 1620 |
| tgctggtgat tcattgaaga ggctggaaga ggaggagatt aaaaggtgta aggagacttc | 1680 |
| tgaacatggg gcatattcag atctgcttca gcgtcagaag gcaacagtgc ttgagaatag | 1740 |
| caaacttaca ggaaagataa gtgagttgga aagaatggta gctgaactaa agaaacaaaa | 1800 |
| gtcccgagta gaggaagaac ttccgaaggt cagggaggct gcagaaaatg aattgagaaa | 1860 |
| gcagcagaga aatgtagaag atatctctct gcagaagata agggctgaaa gtgaagccaa | 1920 |
| gcagtaccgc agggaacttg aaaccattgt gagagagaag gaagccgctg aaagagaact | 1980 |
| ggagcgggtg aggcagctca ccatagaggc cgaggctaaa agagctgccg tggaagagaa | 2040 |
| cctcctgaat tttcgcaatc agttggagga aaacacctttt accagacgaa cactggaaga | 2100 |

-continued

```
tcatcttaaa agaaaagatt taagtctcaa tgatttggag caacaaaaaa ataaattaat    2160
ggaagaatta agaagaaaga gagacaatga ggaagaactc ttgaagctga taaagcagat    2220
ggaaaaagac cttgcatttc agaaacaggt agcagagaaa cagttgaaag aaaagcagaa    2280
aattgaattg gaagcaagaa gaaaaataac tgaaattcag tatacatgta gagaaaatgc    2340
attgccagtg tgtccgatca cacaggctac atcatgcagg gcagtaacgg gtctccagca    2400
agaacatgac aagcagaaag cagaagaact caaacagcag gtagatgaac taacagctgc    2460
caatagaaag gctgaacaag acatgagaga gctgacatat gaacttaatg ccctccagct    2520
tgaaaaaacg tcatctgagg aaaaggctcg tttgctaaaa gataaactag atgaaacaaa    2580
taatacactc agatgcctta agttggagct ggaaaggaag gatcaggcgg agaaagggta    2640
ttctcaacaa ctcagagagc ttggtaggca attgaatcaa accacaggta agctgaaga     2700
agccatgcaa gaagctagtg atctcaagaa aataaagcgc aattatcagt tagaattaga    2760
atctcttaat catgaaaaag ggaaactaca agagaagta gacagaatca caagggcaca     2820
tgctgtagct gagaagaata ttcagcattt aaattcacaa attcattctt ttcgagatga    2880
gaaagaatta gaaagactac aaatctgcca gagaaaatca gatcatctaa aagaacaatt    2940
tgagaaaagc catgagcagt tgcttcaaaa tatcaaagct gaaaagaaa ataatgataa      3000
aatccaaagg ctcaatgaag aattggagaa aagtaatgag tgtgcagaga tgctaaaaca    3060
aaaagtagag gagcttacta ggcagaataa tgaaaccaaa ttaatgatgc agagaattca    3120
ggcagaatca gagaatatag ttttagagaa acaaactatc cagcaaagat gtgaagcact    3180
gaaaattcag gcagatggtt ttaaagatca gctacgcagc acaaatgaac acttgcataa    3240
acagacaaaa acagagcagg attttcaaag aaaaattaaa tgcctagaag aagacctggc    3300
gaaaagtcaa aatttggtaa gtgaatttaa gcaaaagtgt gaccaacaga acattatcat    3360
ccagaatacc aagaaagaag ttagaaatct gaatgcggaa ctgaatgctt ccaaagaaga    3420
gaagcgacgc ggggagcaga agttcagct acaacaagct caggtgcaag agttaaataa      3480
caggttgaaa aaagtacaag acgaattaca cttaaagacc atagaggagc agatgaccca    3540
cagaaagatg gttctgtttc aggaagaatc tggtaaattc aaacaatcag cagaggagtt    3600
tcggaagaag atggaaaaat taatggagtc caaagtcatc actgaaaatg atatttcagg    3660
cattaggctt gactttgtgt ctcttcaaca agaaaactct agagcccaag aaaatgctaa    3720
gctttgtgaa acaaacatta agaacttga aagcagctt caacagtatc gtgaacaaat      3780
gcagcaaggg cagcacatgg aagcaaatca ttaccaaaaa tgtcagaaac ttgaggatga    3840
gctgatagcc cagaagcgtg aggttgaaaa cctgaagcaa aaaatggacc aacagatcaa    3900
agagcatgaa catcaattag ttttgctcca gtgtgaaatt caaaaaaaga gcacagccaa    3960
agactgtacc ttcaaaccag attttgagat gacagtgaag gagtgccagc actctggaga    4020
gctgtcctct agaaacactg gacaccttca cccaacaccc agatcccctc tgttgagatg    4080
gactcaagaa ccacagccat tggaagagaa gtggcagcat cgggttgttg aacagatacc    4140
caaagaagtc caattccagc caccagggc tccactcgag aaagagaaaa gccagcagtg      4200
ttactctgag tacttttctc agacaagcac cgagttacag ataacttttg atgagacaaa    4260
ccccattaca agactgtctg aaattgagaa gataagagac caagccctga caattctag      4320
accacctgtt aggtatcaag ataacgcatg tgaaatggaa ctggtgaagg ttttgacacc    4380
cttagagata gctaagaaca agcagtatga tatgcataca gaagtcacaa cattaaaaca    4440
```

```
agaaaagaac ccagttccca gtgctgaaga atggatgctt gaagggtgca gagcatctgg    4500
tggactcaag aaagggggatt tccttaagaa gggcttagaa ccagagacct tccagaactt    4560
tgatggtgat catgcatgtt cagtcaggga tgatgaattt aaattccaag ggcttaggca    4620
cactgtgact gccaggcagt tggtggaagc taagcttctg gacatgagaa caattgagca    4680
gctgcgactc ggtcttaaga ctgttgaaga agttcagaaa actcttaaca agtttctgac    4740
gaaagccacc tcaattgcag ggctttacct agaatctaca aaagaaaaga tttcatttgc    4800
ctcagcggcc gagagaatca taatagacaa aatggtggct ttggcatttt tagaagctca    4860
ggctgcaaca ggttttataa ttgatcccat ttcaggtcag acatattctg ttgaagatgc    4920
agttcttaaa ggagttgttg accccgaatt cagaattagg cttcttgagg cagagaaggc    4980
agctgtggga tattcttatt cttctaagac attgtcagtg tttcaagcta tggaaaatag    5040
aatgcttgac agacaaaaag gtaaacatat cttggaagcc cagattgcca gtgggggtgt    5100
cattgaccct gtgagaggca ttcgtgttcc tccagaaatt gctctgcagc aggggttgtt    5160
gaataatgcc atcttacagt ttttacatga gccatccagc aacacaagag ttttccctaa    5220
tcccaataac aagcaagctc tgtattactc agaattactg cgaatgtgtg tatttgatgt    5280
agagtcccaa tgctttctgt ttccatttgg ggagaggaac atttccaatc tcaatgtcaa    5340
gaaaacacat agaatttctg tagtagatac taaaacagga tcagaattga ccgtgtatga    5400
ggctttccag agaaacctga ttgagaaaag tatatatctt gaactttcag ggcagcaata    5460
tcagtggaag gaagctatgt tttttgaatc ctatgggcat tcttctcata tgctgactga    5520
tactaaaaca ggattacact tcaatattaa tgaggctata gagcagggaa caattgacaa    5580
agccttggtc aaaaagtatc aggaaggcct catcacactt acagaacttg ctgattcttt    5640
gctgagccgg ttagtcccca agaaagattt gcacagtcct gttgcagggt attggctgac    5700
tgctagtggg gaaaggatct ctgtactaaa agcctcccgt agaaatttgg ttgatcggat    5760
tactgccctc cgatgccttg aagcccaagt cagtacaggg ggcataattg atcctcttac    5820
tggcaaaaag taccgggtgg ccgaagcttt gcatagagc ctggttgatg aggggtttgc    5880
ccagcagctg cgacagtgtg aattagtaat cacagggatt ggccatccca tcactaacaa    5940
aatgatgtca gtggtggaag ctgtgaatgc aaatattata aataaggaaa tgggaatccg    6000
atgtttggaa tttcagtact tgacaggagg gttgatagag ccacaggttc actctcggtt    6060
atcaatagaa gaggctctcc aagtaggtat tatagatgtc ctcattgcca caaaactcaa    6120
agatcaaaag tcatatgtca gaaatataat atgccctcag acaaaaagaa agttgacata    6180
taaagaagcc ttagaaaaag ctgattttga tttccacaca ggacttaaac tgttagaagt    6240
atctgagccc ctgatgacag gaatttctag cctctactat tcttcctaat gggacatgtt    6300
taaataactg tgcaaggggt gatgcaggct ggttcatgcc actttttcag agtatgatga    6360
tatcggctac atatgcagtc tgtgaattat gtaacatact ctatttcttg agggctgcaa    6420
attgctaagt gctcaaaata gagtaagttt taaattgaaa attacataag atttaatgcc    6480
cttcaaatgg tttcatttag ccttgagaat ggttttttga aacttggcca cactaaaatg    6540
tttttttttt tttacgtaga atgtgggata aacttgatga actccaagtt cacagtgtca    6600
tttcttcaga actccccttc attgaatagt gatcatttat taaatgataa attgcactcg    6660
ctgaaagagc acgtcatgaa gcaccatgga atcaaagaga agatataaa ttcgttccca    6720 cagccttcaa gctgcagtgt tttagattgc ttcaaaaaat gaaaaagttt tgccttttc    6780 gatatagtga ccttctttgc atattaaaat gtttaccaca atgtcccatt tctagttaag    6840
```

```
tcttcgcact tgaaagctaa cattatgaat attatgtgtt ggaggagggg aaggatttc      6900
ttcattctgt gtattttccg g                                                6921
```

<210> SEQ ID NO 118
<211> LENGTH: 946
<212> TYPE: DNA
<213> ORGANISM: Homo sapien

<400> SEQUENCE: 118

```
cttctgactg ggctcaggct gacaggtaga gctcaccatg gcttcttgtg tccttgtccc      60
ctccccatca cagctgtggt gcagtccacc gtctccagtg gctatggcgg tgccagtggt     120
gtcggcagtg gcttaggcct gggtggagga agcagctact cctatggcag tggtcttggc     180
gttggaggtg gcttcagttc cagcagtggc agagccattg ggggtggcct cagctctgtt     240
ggaggcggca gttccaccat caagtacacc accacctcct cctccagcag gaagagctat     300
aagcactaaa gtgcgtctgc tagctctcgg tcccacagtc ctcaggcccc tctctggctg     360
cagagccctc tcctcaggtt gcctgtcctc tcctggcctc cagtctcccc tgctgtccca     420
ggtagagctg gggatgaatg cttagtgccc tcacttcttc tctctctctc tataccatct     480
gagcacccat tgctcaccat cagatcaacc tctgatttta catcatgatg taatcaccac     540
tggagcttca ctgttactaa attattaatt tcttgcctcc agtgttctat ctctgaggct     600
gagcattata agaaaatgac ctctgctcct tttcattgca gaaaattgcc agggcttat      660
ttcagaacaa cttccactta cttttccactg gctctcaaac tctctaactt ataagtgttg    720
tgaacccca cccaggcagt atccatgaaa gcacaagtga ctagtcctat gatgtacaaa      780
gcctgtatct ctgtgatgat ttctgtgctc ttcactgttt gcaattgcta aataaagcag     840
atttataata catatattct tttactttgc cttgctttgg ggccaaagtt ttgggcttaa     900
acttttttat ctgataagtg aatagttgtt tttaaaagat aatcta                    946
```

<210> SEQ ID NO 119
<211> LENGTH: 8948
<212> TYPE: DNA
<213> ORGANISM: Homo sapien

<400> SEQUENCE: 119

```
tcaacagccc ctgctccttg ggcccctcca tgccatgccg taatctctcc cacccgacca      60
acaccaacac ccagctccga cgcagctcct ctgcgccctt gccgccctcc gagccacagc     120
tttcctcccg ctcctgcccc cggcccgtcg ccgtctccgc gctcgcagcg gcctcgggag     180
ggcccaggta gcgagcagcg acctcgcgag ccttccgcac tcccgcccgg ttccccggcc     240
gtccgcctat ccttggcccc ctccgctttc tccgcgccgg cccgcctcgc ttatgcctcg     300
gcgctgagcc gctctcccga ttgcccgccg acatgagctg caacgaggc tcccacccgc      360
ggatcaacac tctgggccgc atgatccgcg ccgagtctgg cccggacctg cgctacgagg     420
tgaccagcgg cggcggggc accagcagga tgtactattc tcggcgcggc gtgatcaccg     480
accagaactc ggacggctac tgtcaaaccg gcacgatgtc caggcaccag aaccagaaca     540
ccatccagga gctgctgcag aactgctccg actgcttgat gcgagcagag ctcatcgtgc     600
agcctgaatt gaagtatgga gatggaatac aactgactcg gagtcgagaa ttggatgagt     660
gttttgccca ggccaatgac caaatggaaa tcctcgacag cttgatcaga gagatgcggc     720
agatgggcca gccctgtgat gcttaccaga aaaggcttct tcagctccaa gagcaaatgc     780
```

| | |
|---|---|
| gagcccttta taaagccatc agtgtccctc gagtccgcag ggccagctcc aagggtggtg | 840 |
| gaggctacac ttgtcagagt ggctctggct gggatgagtt caccaaacat gtcaccagtg | 900 |
| aatgtttggg gtggatgagg cagcaaaggg cggagatgga catggtggcc tggggtgtgg | 960 |
| acctggcctc agtggagcag cacattaaca gccaccgggg catccacaac tccatcggcg | 1020 |
| actatcgctg gcagctggac aaaatcaaag ccgacctgcg cgagaaatct gcgatctacc | 1080 |
| agttggagga ggagtatgaa aacctgctga agcgtccttt gagaggatg gatcacctgc | 1140 |
| gacagctgca gaacatcatt caggccacgt ccagggagat catgtggatc aatgactgcg | 1200 |
| aggaggagga gctgctgtac gactggagcg acaagaacac caacatcgct cagaaacagg | 1260 |
| aggccttctc catacgcatg agtcaactgg aagttaaaga aaagagctc aataagctga | 1320 |
| aacaagaaag tgaccaactt gtcctcaatc agcatccagc ttcagacaaa attgaggcct | 1380 |
| atatggacac tctgcagacg cagtggagtt ggattcttca gatcaccaag tgcattgatg | 1440 |
| ttcatctgaa agaaaatgct gcctactttc agttttttga agaggcgcag tctactgaag | 1500 |
| catacctgaa ggggctccag gactccatca ggaagaagta cccctgcgac aagaacatgc | 1560 |
| ccctgcagca cctgctggaa cagatcaagg agctggagaa agaacgagag aaaatccttg | 1620 |
| aatacaagcg tcaggtgcag aacttggtaa acaagtctaa gaagattgta cagctgaagc | 1680 |
| ctcgtaaccc agactacaga agcaataaac ccattattct cagagctctc tgtgactaca | 1740 |
| aacaagatca gaaaatcgtg cataagggg atgagtgtat cctgaaggac aacaacgagc | 1800 |
| gcagcaagtg gtacgtgacg ggcccgggag gcgttgacat gcttgttccc tctgtggggc | 1860 |
| tgatcatccc tcctccgaac ccactggccg tggacctctc ttgcaagatt gagcagtact | 1920 |
| acgaagccat cttggctctg tggaaccagc tctacatcaa catgaagagc ctggtgtcct | 1980 |
| ggcactactg catgattgac atagagaaga tcagggccat gacaatcgcc aagctgaaaa | 2040 |
| caatgcggca ggaagattac atgaagacga tagccgacct tgagttacat taccaagagt | 2100 |
| tcatcagaaa tagccaaggc tcagagatgt ttggagatga tgacaagcgg aaaatacagt | 2160 |
| ctcagttcac cgatgcccag aagcattacc agaccctggt cattcagctc cctggctatc | 2220 |
| cccagcacca gacagtgacc acaactgaaa tcactcatca tggaacctgc caagatgtca | 2280 |
| accataataa agtaattgaa accaacagag aaaatgacaa gcaagaaaca tggatgctga | 2340 |
| tggagctgca gaagattcgc aggcagatag agcactgcga gggcaggatg actctcaaaa | 2400 |
| acctccctct agcagaccag gggtcttctc accacatcac agtgaaaatt aacgagctta | 2460 |
| agagtgtgca gaatgattca caagcaattg ctgaggttct caaccagctt aaagatatgc | 2520 |
| ttgccaactt cagaggttct gaaaagtact gctatttaca gaatgaagta tttggactat | 2580 |
| ttcagaaact ggaaaatatc aatggtgtta cagatggcta cttaaatagc ttatgcacag | 2640 |
| taagggcact gctccaggct attctccaaa cagaagacat gttaaaggtt tatgaagcca | 2700 |
| ggctcactga ggaggaaact gtctgcctgg acctggataa agtggaagct taccgctgtg | 2760 |
| gactgaagaa aataaaaaat gacttgaact tgaagaagtc gttgttggcc actatgaaga | 2820 |
| cagaactaca gaaagcccag cagatccact ctcagacttc acagcagtat ccactttatg | 2880 |
| atctggactt gggcaagttc ggtgaaaaag tcacacagct gacagaccgc tggcaaagga | 2940 |
| tagataaaca gatcgacttt agattatggg acctggagaa acaaatcaag caattgagga | 3000 |
| attatcgtga taactatcag gctttctgca gtggctctaa tgatcgtaaa cgccgccagg | 3060 |
| attccttaga atccatgaaa tttggagatt ccaacacagt catgcggttt ttgaatgagc | 3120 |
| agaagaactt gcacagtgaa atatctggca aacgagacaa atcagaggaa gtacaaaaaa | 3180 |

```
ttgctgaact ttgcgccaat tcaattaagg attatgagct ccagctggcc tcatacacct   3240
caggactgga aactctgctg aacataccta tcaagaggac catgattcag tcccttctg    3300 gggtgattct gcaagaggct gcagatgttc atgctcggta cattgaacta cttacaagat   3360
ctggagacta ttacaggttc ttaagtgaga tgctgaagag tttggaagat ctgaagctga   3420
aaaataccaa gatcgaagtt ttggaagagg agctcagact ggcccgagat gccaactcgg   3480
aaaactgtaa taagaacaaa ttcctggatc agaacctgca gaaataccag gcagagtgtt   3540
cccagttcaa agcgaagctt gcgagcctgg aggagctgaa gagacaggct gagctggatg   3600
ggaagtcggc taagcaaaat ctagacaagt gctacggcca aataaaagaa ctcaatgaga   3660
agatcacccg actgacttat gagattgaag atgaaaagag aagaagaaaa tctgtggaag   3720
acagatttga ccaacagaag aatgactatg accaactgca gaaagcaagg caatgtgaaa   3780
aggagaacct tggttggcag aaattagagt ctgagaaagc catcaaggag aaggagtacg   3840
agattgaaag gttgagggtt ctactgcagg aagaaggcac ccggaagaga gaatatgaaa   3900
atgagctggc aaaggtaaga aaccactata tgaggagat gagtaattta aggaacaagt    3960
atgaaacaga gattaacatt acgaagacca ccatcaagga gatatccatg caaaaagagg   4020
atgattccaa aaatcttaga aaccagcttg atagactttc aagggaaaat cgagatctga   4080
aggatgaaat tgtcaggctc aatgacagca tcttgcaggc cactgagcag cgaaggcgag   4140
ctgaagaaaa cgcccttcag caaaaggcct gtggctctga gataatgcag aagaagcagc   4200
atctggagat agaactgaag caggtcatgc agcagcgctc tgaggacaat gcccggcaca   4260
agcagtccct ggaggaggct gccaagacca ttcaggacaa aaataaggag atcgagagac   4320
tcaaagctga gtttcaggag gaggccaagc gccgctggga atatgaaaat gaactgagta   4380
aggtaagaaa caattatgat gaggagatca ttagcttaaa aaatcagttt gagaccgaga   4440
tcaacatcac caagaccacc atccaccagc tcaccatgca gaaggaagag gataccagtg   4500
gctaccgggc tcagatagac aatctcaccc gagaaaacag gagcttatct gaagaaataa   4560
agaggctgaa gaacactcta acccagacca cagagaatct caggagggtg gaagaagaca   4620
tccaacagca aaaggccact ggctctgagg tgtctcagag gaaacagcag ctggaggttg   4680
agctgagaca agtcactcag atgcgaacag aggagagcgt aagatataag caatctcttg   4740
atgatgctgc caaaccatc caggataaaa acaaggagat agaaaggtta aaacaactga    4800
tcgacaaaga aacaaatgac cggaaatgcc tggaagatga aaacgcgaga ttacaaaggg   4860
tccagtatga cctgcagaaa gcaaacagta gtgcgacgga gacaataaac aaactgaagg   4920
ttcaggagca agaactgaca cgcctgagga tcgactatga aagggtttcc caggagagga   4980
ctgtgaagga ccaggatatc acgcggttcc agaactctct gaaagagctg cagctgcaga   5040
agcagaaggt ggaagaggag ctgaatcggc tgaagaggac cgcgtcagaa gactcctgca   5100
agaggaagaa gctggaggaa gagctggaag gcatgaggag gtcgctgaag gagcaagcca   5160
tcaaaatcac caacctgacc cagcagctgg agcaggcatc cattgttaag aagaggagtg   5220
aggatgacct ccggcagcag agggacgtgc tggatggcca cctgagggaa aagcagagga   5280
cccaggaaga gctgaggagg ctctcttctg aggtcgaggc cctgaggcgg cagttactcc   5340
aggaacagga aagtgtcaaa caagctcact tgaggaatga gcatttccag aaggcgatag   5400
aagataaaag cagaagctta aatgaaagca aaatagaaat tgagaggctg cagtctctca   5460
cagagaacct gaccaaggag cacttgatgt tagaagaaga actgcggaac ctgaggctgg   5520
```

```
agtacgatga cctgaggaga ggacgaagcg aagcggacag tgataaaaat gcaaccatct   5580
tggaactaag gagccagctg cagatcagca acaaccggac cctggaactg caggggctga   5640
ttaatgattt acagagagag agggaaaatt tgagacagga aattgagaaa ttccaaaagc   5700
aggctttaga ggcatctaat aggattcagg aatcaaagaa tcagtgtact caggtggtac   5760
aggaaagaga gagccttctg gtgaaaatca aagtcctgga gcaagacaag caaggctgc    5820 agaggctgga ggatgagctg aatcgtgcaa aatcaactct agaggcagaa accagggtga   5880
aacagcgcct ggagtgtgag aaacagcaaa ttcagaatga cctgaatcag tggaagactc   5940
aatattcccg caaggaggag gctattagga agatagaatc ggaaagagaa aagagtgaga   6000
gagagaagaa cagtcttagg agtgagatcg aaagactcca agcagagatc aagagaattg   6060
aagagaggtg caggcgtaag ctggaggatt ctaccaggga gacacagtca cagttagaaa   6120
cagaacgctc ccgatatcag agggagattg ataaactcag acagcgccca tatgggtccc   6180
atcgagagac ccagactgag tgtgagtgga ccgttgacac ctccaagctg gtgtttgatg   6240
ggctgaggaa gaaggtgaca gcaatgcagc tctatgagtg tcagctgatc gacaaaacaa   6300
ccttggacaa actattgaag gggaagaagt cagtggaaga agttgcttct gaaatccagc   6360
cattccttcg gggtgcagga tctatcgctg gagcatctgc ttctcctaag gaaaaatact   6420
ctttggtaga ggccaagaga aagaaattaa tcagcccaga atccacagtc atgcttctgg   6480
aggcccaggc agctacaggt ggtataattg atccccatcg gaatgagaag ctgactgtcg   6540
acagtgccat agctcgggac ctcattgact tcgatgaccg tcagcagata tatgcagcag   6600
aaaaagctat cactggtttt gatgatccat tttcaggcaa gacagtatct gtttcagaag   6660
ccatcaagaa aaatttgatt gatagagaaa ccggaatgcg cctgctggaa gcccagattg   6720
cttcaggggg tgtagtagac cctgtgaaca gtgtcttttt gccaaaagat gtcgccttgg   6780
cccgggggct gattgataga gatttgtatc gatccctgaa tgatccccga gatagtcaga   6840
aaaactttgt ggatccagtc accaaaaaga aggtcagtta cgtgcagctg aaggaacggt   6900
gcagaatcga accacatact ggtctgctct tgctttcagt acagaagaga agcatgtcct   6960
tccaaggaat cagacaacct gtgaccgtca ctgagctagt agattctggt atattgagac   7020
cgtccactgt caatgaactg gaatctggtc agatttctta tgacgaggtt ggtgagagaa   7080
ttaaggactt cctccagggt tcaagctgca tagcaggcat atacaatgag accacaaaac   7140
agaagcttgg catttatgag gccatgaaaa ttggcttagt ccgacctggt actgctctgg   7200
agttgctgga agcccaagca gctactggct ttatagtgga tcctgttagc aacttgaggt   7260
taccagtgga ggaagcctac aagagaggtc tggtgggcat tgagttcaaa gagaagctcc   7320
tgtctgcaga acgagctgtc actgggtata atgatcctga acaggaaac atcatctctt    7380 tgttccaagc catgaataag gaactcatcg aaaagggcca cggtattcgc ttattagaag   7440
cacagatcgc aaccggggggg atcattgacc caaggagag ccatcgtta ccagttgaca    7500 tagcatataa gagggctat ttcaatgagg aactcagtga gattctctca gatccaagtg     7560
atgataccaa aggattttt gaccccaaca ctgaagaaaa tcttacctat ctgcaactaa     7620
aagaaagatg cattaaggat gaggaaacag gctctgtctt tctgcctctg aaagaaaga   7680 agaaacaggt gcagacatca caaaagaata ccctcaggaa gcgtagagtg gtcatagttg    7740
acccagaaac caataaagaa atgtctgttc aggaggccta caagaagggc ctaattgatt   7800
atgaaacctt caaagaactg tgtgagcagg aatgtgaatg ggaagaaata accatcacgg   7860
gatcagatgg ctccaccagg gtggtcctgg tagatagaaa gacaggcagt cagtatgata   7920
```

```
ttcaagatgc tattgacaag ggccttgttg acaggaagtt ctttgatcag taccgatccg      7980
gcagcctcag cctcactcaa tttgctgaca tgatctcctt gaaaaatggt gtcggcacca      8040
gcagcagcat gggcagtggt gtcagcgatg atgtttttag cagctcccga catgaatcag      8100
taagtaagat ttccaccata tccagcgtca ggaatttaac cataaggagc agctcttttt      8160
cagacaccct ggaagaatcg agccccattg cagccatctt tgacacagaa aacctggaga      8220
aaatctccat tacagaaggt atagagcggg gcatcgttga cagcatcacg ggtcagaggc      8280
ttctggaggc tcaggcctgc acaggtgcca tcatccaccc aaccacgggc cagaagctgt      8340
cacttcagga cgcagtctcc cagggtgtga ttgaccaaga catggccacc agcgtgaagc      8400
ctgctcagaa agccttcata ggcttcgagg gtgtgaaggg aaagaagaag atgtcagcag      8460
cagaggcagt gaaagaaaaa tggctcccgt atgaggctgg ccagcgcttc ctggagttcc      8520
agtacctcac gggaggtctt gttgacccgg aagtgcatgg gaggataagc accgaagaag      8580
ccatccggaa ggggttcata gatggccgcg ccgcacagag gctgcaagac accagcagct      8640
atgccaaaat cctgacctgc cccaaaacca aattaaaaat atcctataag gatgccataa      8700
atcgctccat ggtagaagat atcactgggc tgcgccttct ggaagccgcc tccgtgtcgt      8760
ccaagggctt acccagccct tacaacatgt cttcggctcc ggggtcccgc tccggctccc      8820
gctcgggatc tcgctccgga tctcgctccg gtcccgcag tgggtcccgg agaggaagct      8880
ttgacgccac agggaattct tcctactctt attcctactc atttagcagt agttctattg      8940
ggcactag                                                              8948
```

<210> SEQ ID NO 120
<211> LENGTH: 587
<212> TYPE: DNA
<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 120

```
cgtcctaagc acttagacta catcagggaa gaacacagac cacatccctg tcctcatgcg       60
gcttatgttt tctggaagaa agtggagacc nagtccttgg ctttagggct ccccggctgg      120
gggctgtgca ntccggtcag ggcgggaagg gaaatgcacc gctgcatgtg aacttacagc      180
ccaggcggat gcccctcc ttagcactac ctggcctcct gcatccctc gcctcatgtt         240 cctcccacct tcaaanaatg aanaacccca tgggcccagc cccttgccct ggggaaccaa      300
ggcagccttc caaaactcag gggctgaagc anactattag ggcaggggct gactttgggt      360
gacactgccc attccctctc agggcagctc angtcacccn ggnctcttga acccagcctg      420
ttcctttgaa aaagggcaaa actgaaaagg gcttttccta naaaaagaaa aaccagggaa      480
ctttgccagg gcttcnntnt taccaaaacn ncttctcnng gattttaat tccccattng       540 gcctccactt accngggggcn atgccccaaa attaanaatt tcccatc                   587
```

<210> SEQ ID NO 121
<211> LENGTH: 619
<212> TYPE: DNA
<213> ORGANISM: Homo sapien
<220> FEATURE:
<221> NAME/KEY: misc_feature
<222> LOCATION: (1)...(619)
<223> OTHER INFORMATION: n = A,T,C or G

```
<400> SEQUENCE: 121
cactagtagg atagaaacac tgtgtcccga gagtaaggag agaagctact attgattaga      60
gcctaaccca ggttaactgc aagaagaggc gggatacttt cagctttcca tgtaactgta     120
tgcataaagc caatgtagtc cagtttctaa gatcatgttc caagctaact gaatcccact     180
tcaatacaca ctcatgaact cctgatggaa caataacagg cccaagcctg tggtatgatg     240
tgcacacttg ctagactcan aaaaaatact actctcataa atgggtggga gtattttggt     300
gacaacctac tttgcttggc tgagtgaagg aatgatattc atatattcat ttattccatg     360
gacatttagt tagtgctttt tatataccag gcatgatgct gagtgacact cttgtgtata     420
tttccaaatt tttgtacagt cgctgcacat atttgaaatc atatattaag acttccaaaa     480
aatgaagtcc ctggtttttc atggcaactt gatcagtaaa ggattcncct ctgtttggta     540
cttaaaacat ctactatatn gttnanatga aattccttt ccccncctcc cgaaaaaana      600
aagtggtggg gaaaaaaaa                                                  619

<210> SEQ ID NO 122
<211> LENGTH: 1475
<212> TYPE: DNA
<213> ORGANISM: Homo sapien

<400> SEQUENCE: 122
tccacctgtc cccgcagcgc cggctcgcgc cctcctgccg cagccaccga gccgccgtct      60
agcgccccga cctcgccacc atgagagccc tgctggcgcg cctgcttctc tgcgtcctgg     120
tcgtgagcga ctccaaaggc agcaatgaac ttcatcaagt tccatcgaac tgtgactgtc     180
taaatggagg aacatgtgtg tccaacaagt acttctccaa cattcactgg tgcaactgcc     240
caaagaaatt cggagggcag cactgtgaaa tagataagtc aaaaacctgc tatgagggga     300
atggtcactt ttaccgagga aaggccagca ctgacaccat gggccggccc tgcctgccct     360
ggaactctgc cactgtcctt cagcaaacgt accatgccca cagatctgat gctcttcagc     420
tgggcctggg gaaacataat tactgcagga acccagacaa ccggaggcga ccctggtgct     480
atgtgcaggt gggcctaaag ccgcttgtcc aagagtgcat ggtgcatgac tgcgcagatg     540
gaaaaaagcc ctcctctcct ccagaagaat taaaatttca gtgtggccaa aagactctga     600
ggccccgctt taagattatt gggggagaat tcaccaccat cgagaaccag ccctggtttg     660
cggccatcta caggaggcac cggggggggct ctgtcaccta cgtgtgtgga ggcagcctca     720
tcagcccttg ctgggtgatc agcgccacac actgcttcat tgattaccca aagaaggagg     780
actacatcgt ctacctgggt cgctcaaggc ttaactccaa cacgcaaggg gagatgaagt     840
ttgaggtgga aaacctcatc ctacacaagg actacagcgc tgacacgctt gctcaccaca     900
acgacattgc cttgctgaag atccgttcca aggaggggcag gtgtgcgcag ccatcccgga     960
ctatacagac catctgcctg ccctcgatgt ataacgatcc ccagtttggc acaagctgtg    1020
agatcactgg cttttggaaaa gagaattcta ccgactatct ctatccggag cagctgaaga    1080
tgactgttgt gaagctgatt cccaccggga gtgtcagca gccccactac tacggctctg    1140
aagtcaccac caaatgctg tgtgctgctg acccacagtg gaaaacagat tcctgccagg    1200
gagactcagg ggaccccctc gtctgttccc tccaaggccg catgacttg actggaattg    1260 tgagctgggg ccgtggatgt gccctgaagg acaagccagg cgtctacacg agagtctcac    1320
acttcttacc ctggatccgc agtcacacca aggaagagaa tggcctggcc ctctgagggt    1380
ccccagggag gaaacgggca ccacccgctt tcttgctggt tgtcattttt gcagtagagt    1440
```
catctccatc agctgtaaga agagactggg aagat 1475

<210> SEQ ID NO 123
<211> LENGTH: 2294
<212> TYPE: DNA
<213> ORGANISM: Homo sapien

<400> SEQUENCE: 123

| | | | | | |
|---|---|---|---|---|---|
| cagcgccggc | tcgcgccctc | ctgccgcagc | caccgagccg | ccgtctagcg | ccccgacctc | 60 |
| gccaccatga | gagccctgct | ggcgcgcctg | cttctctgcg | tcctggtcgt | gagcgactcc | 120 |
| aaaggcagca | atgaacttca | tcaagttcca | tcgaactgtg | actgtctaaa | tggaggaaca | 180 |
| tgtgtgtcca | acaagtactt | ctccaacatt | cactggtgca | actgcccaaa | gaaattcgga | 240 |
| gggcagcact | gtgaaataga | taagtcaaaa | acctgctatg | aggggaatgg | tcacttttac | 300 |
| cgaggaaagg | ccagcactga | caccatgggc | cggccctgcc | tgccctggaa | ctctgccact | 360 |
| gtccttcagc | aaacgtacca | tgcccacaga | tctgatgctc | ttcagctggg | cctggggaaa | 420 |
| cataattact | gcaggaaccc | agacaaccgg | aggcgaccct | ggtgctatgt | gcaggtgggc | 480 |
| ctaaagccgc | ttgtccaaga | gtgcatggtg | catgactgcg | cagatggaaa | aaagccctcc | 540 |
| tctcctccag | aagaattaaa | atttcagtgt | ggccaaaaga | ctctgaggcc | ccgctttaag | 600 |
| attattgggg | gagaattcac | caccatcgag | aaccagccct | ggtttgcggc | catctacagg | 660 |
| aggcaccggg | ggggctctgt | cacctacgtg | tgtggaggca | gcctcatcag | cccttgctgg | 720 |
| gtgatcagcg | ccacacactg | cttcattgat | tacccaaaga | aggaggacta | catcgtctac | 780 |
| ctgggtcgct | caaggcttaa | ctccaacacg | caaggggaga | tgaagtttga | ggtggaaaac | 840 |
| ctaatcctac | acaaggacta | cagcgctgac | acgcttgctc | accacaacga | cattgccttg | 900 |
| ctgaagatcc | gttccaagga | gggcaggtgt | gcgcagccat | cccggactat | acagaccatc | 960 |
| tgcctgccct | cgatgtataa | cgatcccccag | tttggcacaa | gctgtgagat | cactggcttt | 1020 |
| ggaaaagaga | attctaccga | ctatctctat | ccggagcagc | tgaaaatgac | tgttgtgaag | 1080 |
| ctgatttccc | accgggagtg | tcagcagccc | cactactacg | gctctgaagt | caccaccaaa | 1140 |
| atgctgtgtg | ctgctgaccc | acagtggaaa | acagattcct | gccagggaga | ctcaggggga | 1200 |
| cccctcgtct | gttccctcca | aggccgcatg | actttgactg | gaattgtgag | ctggggccgt | 1260 |
| ggatgtgccc | tgaaggacaa | gccaggcgtc | tacacgagag | tctcacactt | cttaccctgg | 1320 |
| atccgcagtc | acaccaagga | agagaatggc | ctggccctct | gagggtcccc | agggaggaaa | 1380 |
| cgggcaccac | ccgctttctt | gctggttgct | attttgcagt | agagtcatct | ccatcagctg | 1440 |
| taagaagagc | tgggaatata | ggctctgcac | agatggattt | gcctgtgcca | ccaccagggc | 1500 |
| gaacgacaat | agctttaccc | tcaggcatag | gcctgggtgc | tggctgccca | gacccctctg | 1560 |
| gccaggatgg | aggggtggtc | ctgactcaac | atgttactga | ccagcaactt | gtcttttttct | 1620 |
| ggactgaagc | ctgcaggagt | taaaaagggc | agggcatctc | ctgtgcatgg | gctcgaaggg | 1680 |
| agagccagct | cccccgaccg | gtgggcattt | gtgaggccca | tggttgagaa | atgaataatt | 1740 |
| tcccaattag | gaagtgtaag | cagctgaggt | ctcttgaggg | agcttagcca | atgtgggagc | 1800 |
| agcggtttgg | ggagcagaga | cactaacgac | ttcagggcag | ggctctgata | ttccatgaat | 1860 |
| gtatcaggaa | atatatatgt | gtgtgtatgt | ttgcacactt | gtgtgtgggc | tgtgagtgta | 1920 |
| agtgtgagta | agagctggtg | tctgattgtt | aagtctaaat | atttccttaa | actgtgtgga | 1980 |
| ctgtgatgcc | acacagagtg | gtctttctgg | agaggttata | ggtcactcct | ggggcctctt | 2040 |

-continued

| | |
|---|---|
| gggtccccca cgtgacagtg cctgggaatg tattattctg cagcatgacc tgtgaccagc | 2100 |
| actgtctcag tttcactttc acatagatgt ccctttcttg ccagttatc ccttccttt | 2160 |
| agcctagttc atccaatcct cactgggtgg ggtgaggacc actcctgtac actgaatatt | 2220 |
| tatatttcac tatttttatt tatattttg taattttaaa taaaagtgat caataaaatg | 2280 |
| tgattttct gatg | 2294 |

<210> SEQ ID NO 124
<211> LENGTH: 956
<212> TYPE: DNA
<213> ORGANISM: Homo sapien

<400> SEQUENCE: 124

| | |
|---|---|
| gatgagttcc gcaccaagtt tgagacagac caggccctgc gcctgagtgt ggaggccgac | 60 |
| atcaatggcc tgcgcagggt gctggatgag ctgaccctgg ccagagccga cctggagatg | 120 |
| cagattgaga acctcaagga ggagctggcc tacctgaaga agaaccacga ggaggagatg | 180 |
| aacgccctgc gaggccaggt gggtggtgag atcaatgtgg agatggacgc tgccccaggc | 240 |
| gtggacctga gccgcatcct caacgagatg cgtgaccagt atgagaagat ggcagagaag | 300 |
| aaccgcaagg atgccgagga ttggttcttc agcaagacag aggaactgaa ccgcgaggtg | 360 |
| gccaccaaca gtgagctggt gcagagtggc aagagtgaga tctcggagct ccggcgcacc | 420 |
| atgcaggcct ggagataga gctgcagtcc cagctcagca tgaaagcatc cctggagggc | 480 |
| aacctggcgg agacagagaa ccgctactgc gtgcagctgt cccagatcca ggggctgatt | 540 |
| ggcagcgtgg aggagcagct ggcccagctt cgctgcgaga tggagcagca gaaccaggaa | 600 |
| tacaaaatcc tgctggatgt gaagacgcgg ctggagcagg agattgccac ctaccgccgc | 660 |
| ctgctggagg gagaggatgc ccacctgact cagtacaaga agaaccggt gaccacccgt | 720 |
| caggtgcgta ccattgtgga agaggtccag gatggcaagg tcatctcctc ccgcgagcag | 780 |
| gtccaccaga ccacccgctg aggactcagc taccccggcc ggccacccag gaggcaggga | 840 |
| cgcagccgcc ccatctgccc cacagtctcc ggcctctcca gcctcagccc cctgcttcag | 900 |
| tcccttcccc atgcttcctt gcctgatgac aataaaagct tgttgactca gctatg | 956 |

<210> SEQ ID NO 125
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 125

| | |
|---|---|
| aaattatata tagtgnttca gctcccattg tggtgttcat agtcttctag gaacagataa | 60 |
| acttaagtat tcaattcact cttggcattt tttctttaat ataggctttt tagcctattt | 120 |
| ttggaaaact gctttctttc tgagaacctt attctgaatg tcatcaactt taccaaacct | 180 |
| tctaagtcca gagctaactt agtactgttt aagttactat tgactgaatt ttcttcattt | 240 |
| tctgtttagc cagtgttacc aaggtaagct ggggaatgaa gtataccaac ttctttcaga | 300 |
| gcatttagg acattatggc agctttagaa ggctgtcttg tttctagcca agggagagcc | 360 |
| agcgcaggtt ttggatacta gagaaagtca tttgcttgta ctattgccat tttagaaagc | 420 |
| tctgatgtga attcaaattt tacctctgtt acttaaagcc aacaatttta aggcagtagt | 480 |
| tttact | 486 |

<210> SEQ ID NO 126
<211> LENGTH: 3552
<212> TYPE: DNA
<213> ORGANISM: Homo sapien

<400> SEQUENCE: 126

| | | | | | |
|---|---|---|---|---|---|
| cggcaggcag | gtctcgtctc | ggcaccctcc | cggcgcccgc | gttctcctgg | ccctgcccgg | 60 |
| catcccgatg | gccgccgctg | ggccccggcg | ctccgtgcgc | ggagccgtct | gcctgcatct | 120 |
| gctgctgacc | ctcgtgatct | tcagtcgtgc | tggtgaagcc | tgcaaaaagg | tgatacttaa | 180 |
| tgtaccttct | aaactagagg | cagacaaaat | aattggcaga | gttaatttgg | aagagtgctt | 240 |
| caggtctgca | gacctcatcc | ggtcaagtga | tcctgatttc | agagttctaa | atgatgggtc | 300 |
| agtgtacaca | gccagggctg | ttgcgctgtc | tgataagaaa | agatcattta | ccatatggct | 360 |
| ttctgacaaa | aggaaacaga | cacagaaaga | ggttactgtg | ctgctagaac | atcagaagaa | 420 |
| ggtatcgaag | acaagacaca | ctagagaaac | tgttctcagg | cgtgccaaga | ggagatgggc | 480 |
| acctattcct | tgctctatgc | aagagaattc | cttgggccct | ttcccattgt | ttcttcaaca | 540 |
| agttgaatct | gatgcagcac | agaactatac | tgtcttctac | tcaataagtg | gacgtggagt | 600 |
| tgataaagaa | cctttaaatt | tgttttatat | agaaagagac | actggaaatc | tattttgcac | 660 |
| tcggcctgtg | gatcgtgaag | aatatgatgt | ttttgatttg | attgcttatg | cgtcaactgc | 720 |
| agatggatat | tcagcagatc | tgccctccc | actacccatc | agggtagagg | atgaaaatga | 780 |
| caaccaccct | gttttcacag | aagcaattta | taattttgaa | gttttggaaa | gtagtagacc | 840 |
| tggtactaca | gtgggggtgg | tttgtgccac | agacagagat | gaaccggaca | caatgcatac | 900 |
| gcgcctgaaa | tacagcattt | tgcagcagac | accaaggtca | cctgggctct | tttctgtgca | 960 |
| tcccagcaca | ggcgtaatca | ccacagtctc | tcattatttg | gacagagagg | ttgtagacaa | 1020 |
| gtactcattg | ataatgaaag | tacaagacat | ggatggccag | ttttttggat | tgataggcac | 1080 |
| atcaacttgt | atcataacag | taacagattc | aaatgataat | gcacccactt | tcagacaaaa | 1140 |
| tgcttatgaa | gcatttgtag | aggaaaatgc | attcaatgtg | gaaatcttac | gaataccgat | 1200 |
| agaagataag | gatttaatta | acactgccaa | ttggagagtc | aattttacca | ttttaaaggg | 1260 |
| aaatgaaaat | ggacatttca | aaatcagcac | agacaaagaa | actaatgaag | gtgttctttc | 1320 |
| tgttgtaaag | ccactgaatt | atgaagaaaa | ccgtcaagtg | aacctggaaa | ttggagtaaa | 1380 |
| caatgaagcg | ccatttgcta | gagatattcc | cagagtgaca | gccttgaaca | gagccttggt | 1440 |
| tacagttcat | gtgagggatc | tggatgaggg | gcctgaatgc | actcctgcag | cccaatatgt | 1500 |
| gcggattaaa | gaaaacttag | cagtgggggtc | aaagatcaac | ggctataagg | catatgaccc | 1560 |
| cgaaaataga | aatggcaatg | gtttaaggta | caaaaaattg | catgatccta | aaggttggat | 1620 |
| caccattgat | gaaatttcag | ggtcaatcat | aacttccaaa | atcctggata | gggaggttga | 1680 |
| aactcccaaa | aatgagttgt | ataatattac | agtcctggca | atagacaaag | atgatagatc | 1740 |
| atgtactgga | acacttgctg | tgaacattga | agatgtaaat | gataatccac | cagaaatact | 1800 |
| tcaagaatat | gtagtcattt | gcaaaccaaa | aatggggtat | accgacattt | tagctgttga | 1860 |
| tcctgatgaa | cctgtccatg | gagctccatt | ttatttcagt | ttgcccaata | cttctccaga | 1920 |
| aatcagtaga | ctgtggagcc | tcaccaaagt | taatgataca | gctgcccgtc | tttcatatca | 1980 |
| gaaaaatgct | ggatttcaag | aatataccat | tcctattact | gtaaaagaca | gggccggcca | 2040 |
| agctgcaaca | aaattattga | gagttaatct | gtgtgaatgt | actcatccaa | ctcagtgtcg | 2100 |

-continued

```
tgcgacttca aggagtacag gagtaatact tggaaaatgg gcaatccttg caatattact      2160
gggtatagca ctgctctttt ctgtattgct aactttagta tgtggagttt ttggtgcaac      2220
taaagggaaa cgttttcctg aagatttagc acagcaaaac ttaattatat caaacacaga      2280
agcacctgga gacgatagag tgtgctctgc caatggattt atgacccaaa ctaccaacaa      2340
ctctagccaa ggttttttgtg gtactatggg atcaggaatg aaaaatggag ggcaggaaac      2400
cattgaaatg atgaaaggag gaaaccagac cttggaatcc tgccgggggg ctgggcatca      2460
tcatacgctg gactcctgca ggggaggaca cacggaggtg gacaactgca gatacactta      2520
ctcggagtgg cacagtttta ctcaaccccg tctcggtgaa aaattgcatc gatgtaatca      2580
gaatgaagac cgcatgccat cccaagatta tgtcctcact tataactatg agggaagagg      2640
atctccagct ggttctgtgg gctgctgcag tgaaaagcag gaagaagatg gccttgactt      2700
tttaaataat ttggaaccca aatttattac attagcagaa gcatgcacaa agagataatg      2760
tcacagtgct acaattaggt ctttgtcaga cattctggag gtttccaaaa ataatattgt      2820
aaagttcaat ttcaacatgt atgtatatga tgatttttt ctcaattttg aattatgcta      2880
ctcaccaatt tatattttta aagcaagttg ttgcttatct tttccaaaaa gtgaaaaatg      2940
ttaaaacaga caactggtaa atctcaaact ccagcactgg aattaaggtc tctaaagcat      3000
ctgctctttt ttttttttac agatatttta gtaataaata tgctggataa atattagtcc      3060
aacaatagct aagttatgct aatatcacat tattatgtat tcactttaag tgatagttta      3120
aaaaataaac aagaaatatt gagtatcact atgtgaagaa agttttggaa agaaacaat      3180 gaagactgaa ttaaattaaa aatgttgcag ctcataaaga attggactca cccctactgc      3240
actaccaaat tcatttgact ttggaggcaa aatgtgttga agtgccctat gaagtagcaa      3300
ttttctatag gaatatagtt ggaaataaat gtgtgtgtgt atattattat taatcaatgc      3360
aatatttaaa tgaaatgaga acaaagagga aaatggtaaa aacttgaaat gaggctgggg      3420
tatagtttgt cctacaatag aaaaaagaga gagcttccta ggcctgggct cttaaatgct      3480
gcattataac tgagtctatg aggaaatagt tcctgtccaa tttgtgtaat ttgtttaaaa      3540
ttgtaaataa at                                                         3552
```

<210> SEQ ID NO 127
<211> LENGTH: 754
<212> TYPE: DNA
<213> ORGANISM: Homo sapien

<400> SEQUENCE: 127

```
ttttttttt ttgtcattgt tcattgattt taatgagaaa gctaagagag gaaataagta       60
gcctttcaaa ggtcacacag aagtaagtga cagatccagg attcatatcc aagcattctg      120
gctctagtgt ccatgcttct caaccattat gacccaatat tcaaccaaat caatactgaa      180
ggacacgtga atgtatccg gtattttact attacaaaca aaaatccaat gaacattctt       240
gaagacatac acaaaaataa tggttacaat agaagttact ggaattgaaa ttttggttca      300
acctatatta aaatgtaagg cttttgatat agctaataga tttttgaaat gatcagtctt      360
aacgtttgta ggggagcaca ctcctgcatg gggaaaagat tcactgtgaa gcacagagca      420 ccttttatggt tggatcatct tgtcattaaa gttcaggcgt tatctatcct gtaagtggca      480
gaatcaagac tgcaatatcg cctgcttttc tttttaactc atgttttccc ttgactacac      540
tggtcctcaa agtaaaaccc ctgtgtcagt gtactattca tggaatactc tgcaattata      600
accaccttct aatactttta atacccaatc aaaatttatt atacatatgt atcatagata      660
```

```
ctcatctgta aagctgtgct tcaaaatagt gatctcttcc caacattaca atatatatta    720
atgatgtcga acctgcccgg gcggccgctc gaag                                754

<210> SEQ ID NO 128
<211> LENGTH: 374
<212> TYPE: DNA
<213> ORGANISM: Homo sapien

<400> SEQUENCE: 128
aggttttgat taaaaaggca aatgatttta ttgttcgata atcttttaaa aaaataagag     60
gaaggagtaa aattaaagat gaaagatgat tttatttcc ttgtgacctc tatatcccc    120 ttcccctgcc cttggtaagt aactcttgat ggagaaagga ttaaagactc ttatttaacc   180
aaaaaacaga gccagctaat catttccaaa ggttagtatc tccctgctga cctcttcttt   240
ggtttaattg aataaaacta tatgttcata tatgtattaa acaactcag aataacatct    300 tttcttcctt agttaaggca ttataagggc tatactatca tccataataa ccaaggcaat   360
aacttaaaaa gctg                                                     374

<210> SEQ ID NO 129
<211> LENGTH: 546
<212> TYPE: DNA
<213> ORGANISM: Homo sapien

<400> SEQUENCE: 129
agtgtgatgg atatctgcag aattcgggct aagcgtggtc gcggcccgag gtctggaact     60
tcccagcacy tgaaaaggag cctcctgagc tgactcggct aaagccccac tttcgctcct   120
cctcatttct gcctactgat ttccttggag cattcatctg aatattaccg tttgctgtgt   180
aacctggtac atacatagca tgactccctg aatagagtg ggctggggtg cttatgctgg    240
gagagtgatt gacatgcact ttcaagctat atctaccatt tgcagcaaag gagaaaaaat   300
acctcgagta aattccatca ttttttataa catcagcacc tgctccatca tcaaggagtc   360
tcagcgtaac aggatctcca gtctctggct caactgtggc agtgacagtg cattaagaa    420 tgggataaaa tccctgtttc acattggcat aaatcatcac aggatgagga aaatggaggc   480
tgtctctttc cacaaaggct tccacagtgg ctgggggcac agacctgccc gggcggccgc   540
tcgaaa                                                              546

<210> SEQ ID NO 130
<211> LENGTH: 5156
<212> TYPE: DNA
<213> ORGANISM: Homo sapien

<400> SEQUENCE: 130
accaaccgag gcgccgggca gcgacccctg cagcggagac agagactgag cggcccggca     60
ccgccatgcc tgcgctctgg ctgggctgct gcctctgctt gtcgctcctc ctgcccgcag   120
cccgggccac ctccaggagg gaagtctgtg attgcaatgg gaagtccagg cagtgtatct   180
ttgatcggga acttcacaga caaactggta atggattccg ctgcctcaac tgcaatgaca   240
acactgatgg cattcactgc gagaagtgca agaatggctt ttaccggcac agagaagggg   300
accgctgttt gccctgcaat tgtaactcca aggttctct tagtgctcga gtgacaact    360 ccggacggtg cagctgtaaa ccaggtgtga caggagccag atgcgaccga tgtctgccag   420
gcttccacat gctcacggat gcggggtgca cccaagacca gagactgcta gactccaagt   480
```

| | |
|---|---|
| gtgactgtga cccagctggc atcgcagggc cctgtgacgc gggccgctgt gtctgcaagc | 540 |
| cagctgtcac tggagaacgc tgtgataggt gtcgatcagg ttactataat ctggatgggg | 600 |
| ggaaccctga gggctgtacc cagtgtttct gctatgggca ttcagccagc tgccgcagct | 660 |
| ctgcagaata cagtgtccat aagatcacct ctacctttca tcaagatgtt gatggctgga | 720 |
| aggctgtcca acgaaatggg tctcctgcaa agctccaatg gtcacagcgc atcaagatg | 780 |
| tgtttagctc agcccaacga ctagaccctg tctattttgt ggctcctgcc aaatttcttg | 840 |
| ggaatcaaca ggtgagctat ggtcaaagcc tgtcctttga ctaccgtgtg acagaggag | 900 |
| gcagacaccc atctgcccat gatgtgattc tggaaggtgc tggtctacgg atcacagctc | 960 |
| ccttgatgcc acttggcaag acactgcctt gtgggctcac caagacttac acattcaggt | 1020 |
| taaatgagca tccaagcaat aattggagcc cccagctgag ttactttgag tatcgaaggt | 1080 |
| tactgcggaa tctcacagcc ctccgcatcc gagctacata tggagaatac agtactgggt | 1140 |
| acattgacaa tgtgaccctg atttcagccc gccctgtctc tggagcccca gcaccctggg | 1200 |
| ttgaacagtg tatatgtcct gttgggtaca aggggcaatt ctgccaggat tgtgcttctg | 1260 |
| gctacaagag agattcagcg agactggggc cttttggcac ctgtattcct tgtaactgtc | 1320 |
| aaggggagg ggcctgtgat ccagacacag gagattgtta ttcaggggat gagaatcctg | 1380 |
| acattgagtg tgctgactgc ccaattggtt tctacaacga tccgcacgac ccccgcagct | 1440 |
| gcaagccatg tccctgtcat aacgggttca gctgctcagt gatgccggag acggaggagg | 1500 |
| tggtgtgcaa taactgccct cccggggtca ccggtgcccg ctgtgagctc tgtgctgatg | 1560 |
| gctactttgg ggacccettt ggtgaacatg gcccagtgag gccttgtcag ccctgtcaat | 1620 |
| gcaacaacaa tgtggacccc agtgcctctg ggaattgtga ccggctgaca ggcaggtgtt | 1680 |
| tgaagtgtat ccacaacaca gccggcatct actgcgacca gtgcaaagca ggctacttcg | 1740 |
| gggacccatt ggctcccaac ccagcagaca agtgtcgagc ttgcaactgt aaccccatgg | 1800 |
| gctcagagcc tgtaggatgt cgaagtgatg gcacctgtgt ttgcaagcca ggatttggtg | 1860 |
| gcccccaactg tgagcatgga gcattcagct gtccagcttg ctataatcaa gtgaagattc | 1920 |
| agatggatca gtttatgcag cagcttcaga gaatggaggc cctgatttca aaggctcagg | 1980 |
| gtggtgatgg agtagtacct gatacagagc tggaaggcag gatgcagcag gctgagcagg | 2040 |
| cccttcagga cattctgaga gatgcccaga tttcagaagg tgctagcaga tcccttggtc | 2100 |
| tccagttggc caaggtgagg agccaagaga acagctacca gagccgcctg gatgacctca | 2160 |
| agatgactgt ggaaagagtt cgggctctgg gaagtcagta ccagaaccga gttcgggata | 2220 |
| ctcacaggct catcactcag atgcagctga gcctggcaga aagtgaagct tccttgggaa | 2280 |
| acactaacat tcctgcctca gaccactacg tggggccaaa tggctttaaa agtctggctc | 2340 |
| aggaggccac aagattagca gaaagccacg ttgagtcagc cagtaacatg gagcaactga | 2400 |
| caagggaaac tgaggactat tccaaacaag ccctctcact ggtgcgcaag gccctgcatg | 2460 |
| aaggagtcgg aagcggaagc ggtagcccgg acggtgctgt ggtgcaaggg cttgtggaaa | 2520 |
| aattggagaa aaccaagtcc ctggcccagc agttgacaag ggaggccact caagcggaaa | 2580 |
| ttgaagcaga taggtcttat cagcacagtc tccgcctcct ggattcagtg tctcggcttc | 2640 |
| agggagtcag tgatcagtcc tttcaggtgg aagaagcaaa gaggatcaaa caaaaagcgg | 2700 |
| attcactctc aagcctggta accaggcata tggatgagtt caagcgtaca cagaagaatc | 2760 |
| tgggaaactg gaaagaagaa gcacagcagc tcttacagaa tggaaaaagt gggagagaga | 2820 |
| aatcagatca gctgctttcc cgtgccaatc ttgctaaaag cagagcacaa gaagcactga | 2880 |

```
gtatgggcaa tgccactttt tatgaagttg agagcatcct taaaaacctc agagagtttg    2940
acctgcaggt ggacaacaga aaagcagaag ctgaagaagc catgaagaga ctctcctaca    3000
tcagccagaa ggtttcagat gccagtgaca agacccagca agcagaaaga gccctgggga    3060
gcgctgctgc tgatgcacag agggcaaaga atggggccgg ggaggccctg gaaatctcca    3120
gtgagattga acaggagatt gggagtctga acttggaagc caatgtgaca gcagatggag    3180
ccttggccat ggaaaaggga ctggcctctc tgaagagtga gatgagggaa gtggaaggag    3240
agctggaaag gaaggagctg gagtttgaca cgaatatgga tgcagtacag atggtgatta    3300
cagaagccca gaaggttgat accagagcca agaacgctgg ggttacaatc caagacacac    3360
tcaacacatt agacggcctc ctgcatctga tggaccagcc tctcagtgta gatgaagagg    3420
ggctggtctt actggagcag aagctttccc gagccaagac ccagatcaac agccaactgc    3480
ggcccatgat gtcagagctg aagagaggg cacgtcagca gaggggccac ctccatttgc    3540
tggagacaag catagatggg attctggctg atgtgaagaa cttggagaac attagggaca    3600
acctgccccc aggctgctac aatacccagg ctcttgagca acagtgaagc tgccataaat    3660
atttctcaac tgaggttctt gggatacaga tctcagggct cgggagccat gtcatgtgag    3720
tgggtgggat ggggacattt gaacatgttt aatgggtatg ctcaggtcaa ctgacctgac    3780
cccattcctg atcccatggc caggtggttg tcttattgca ccatactcct tgcttcctga    3840
tgctgggcaa tgaggcagat agcactgggt gtgagaatga tcaaggatct ggaccccaaa    3900
gaatagactg gatggaaaga caaactgcac aggcagatgt ttgcctcata atagtcgtaa    3960
gtggagtcct ggaatttgga caagtgctgt tgggatatag tcaacttatt ctttgagtaa    4020
tgtgactaaa ggaaaaaact ttgactttgc ccaggcatga aattcttcct aatgtcagaa    4080
cagagtgcaa cccagtcaca ctgtggccag taaaatacta ttgcctcata ttgtcctctg    4140
caagcttctt gctgatcaga gttcctccta cttacaaccc agggtgtgaa catgttctcc    4200
attttcaagc tggaagaagt gagcagtgtt ggagtgagga cctgtaaggc aggcccattc    4260
agagctatgg tgcttgctgg tgcctgccac cttcaagttc tggacctggg catgacatcc    4320
tttcttttaa tgatgccatg gcaacttaga gattgcattt ttattaaagc atttcctacc    4380
agcaaagcaa atgttgggaa agtatttact ttttcggttt caaagtgata gaaagtgtg    4440 gcttgggcat tgaaagaggt aaaattctct agatttatta gtcctaattc aatcctactt    4500
ttagaacacc aaaaatgatg cgcatcaatg tattttatct tattttctca atctcctctc    4560
tctttcctcc acccataata agagaatgtt cctactcaca cttcagctgg gtcacatcca    4620
tccctccatt catccttcca tccatctttc catccattac ctccatccat ccttccaaca    4680
tatatttatt gagtacctac tgtgtgccag gggctggtgg gacagtggtg acatagtctc    4740
tgccctcata gagttgattg tctagtgagg aagacaagca ttttttaaaa ataaatttaa    4800
acttacaaac tttgtttgtc acaagtggtg tttattgcaa taaccgcttg gtttgcaacc    4860
tctttgctca acagaacata tgttgcaaga ccctcccatg ggggcacttg agttttggca    4920
aggctgacag agctctgggt tgtgcacatt tctttgcatt ccagctgtca ctctgtgcct    4980
ttctacaact gattgcaaca gactgttgag ttatgataac accagtggga attgctggag    5040
gaaccagagg cacttccacc ttggctggga agactatggt gctgccttgc ttctgtattt    5100
ccttggattt tcctgaaagt gttttttaaat aaagaacaat tgttagaaaa aaaaaa      5156
```

<210> SEQ ID NO 131

```
<211> LENGTH: 671
<212> TYPE: DNA
<213> ORGANISM: Homo sapien

<400> SEQUENCE: 131
aggtctggag ggcccacagc cggatgtggg acaccgggaa aaagtggtca tagcacacat      60
ttttgcatcc cggttgcagt gtgttgcaga cgaagtcctc ttgctcgtca ccccacactt     120
cctgggcagc caycacgagg atcatgactc ggaaaataaa gatgactgtg atccacacct     180
tcccgatgct ggtggagtgt tgttgacac ccccgatgaa agtgtgcagc gtcccccaat      240
ccattgcgct ggtttatccc tgagtcctgt ttccaacgac tgccagtgtt tcagacccaa     300
agaatgaggg caagatccct ctgcgagggt ttcagacctc cttctcctac cccactggag     360
tgcctagaag ccaatgggtg cacagtgatg atacgaatgt caatctttgc tcggtcagtg     420
aggatgtcgc ctggaatatt caaattgaat tacagatgca tgaagagggc gtacaagtta     480
gaattttct ttcgccatac agaaattgtt tagccagatc ttctgtactt cttttccttc      540
cctgacccctt cctgctcccc aggaagggag gtcagccccg tttgcaaaac acaggatgcc   600
cgtgacaccg gagacaggtc ttcttcaccg acaggaagtg ccttctggtg cctgcacgtt     660
ttaactgcta t                                                         671

<210> SEQ ID NO 132
<211> LENGTH: 590
<212> TYPE: DNA
<213> ORGANISM: Homo sapien

<400> SEQUENCE: 132
ctgaatggaa aagcttatgg ctctgtgatg atattagtga ccagcggaga tgataagctt      60
cttggcaatt gcttacccac tgtgctcagc agtggttcaa caattcactc cattgccctg     120
ggttcatctg cagccccaaa tctggaggaa ttatcacgtc ttacaggagg tttaaagttc     180
tttgttccag atatatcaaa ctccaatagc atgattgatg ctttcagtag aatttcctct     240
ggaactggag acatttttcca gcaacatatt cagcttgaaa gtacaggtga aaatgtcaaa    300
cctcaccatc aattgaaaaa cacagtgact gtggataata ctgtgggcaa cgacactatg     360
tttctagtta cgtggcaggc cagtggtcct cctgagatta tattatttga tcctgatgga     420
cgaaaatact acacaaataa ttttatcacc aatctaactt ttcggacagc tagtctttgg     480
attccaggaa cagctaagcc tgggcactgg acttacaccc tgaacaatac ccatcattct     540
ctgcaagccc tgaaagtgac agtgacctct cgcgcctcca actcagacct                590

<210> SEQ ID NO 133
<211> LENGTH: 581
<212> TYPE: DNA
<213> ORGANISM: Homo sapien

<400> SEQUENCE: 133
aggtcctgtc cgggggcact gagaactccc tctggaattc ttgggggtg ttggggagag       60
actgtgggcc tggagataaa acttgtctcc tctaccacca ccctgtaccc tagcctgcac     120
ctgtcctcat ctctgcaaag ttcagcttcc ttccccaggt ctctgtgcac tctgtcttgg     180
atgctctggg gagctcatgg gtggaggagt ctccaccaga gggaggctca ggggactggt     240
tgggccaggg atgaatattt gagggataaa aattgtgtaa gagccaaaga attggtagta     300
gggggagaac agagaggagc tgggctatgg gaaatgattt gaataatgga gctgggaata     360
tggctggata tctggtacta aaaaagggtc tttaagaacc tacttcctaa tctcttcccc     420
```

```
aatccaaacc atagctgtct gtccagtgct ctcttcctgc ctccagctct gccccaggct    480
cctcctagac tctgtccctg ggctagggca ggggaggagg gagagcaggg ttgggggaga    540
ggctgaggag agtgtgacat gtggggagag gaccagacct c                       581

<210> SEQ ID NO 134
<211> LENGTH: 4797
<212> TYPE: DNA
<213> ORGANISM: Homo sapien
<220> FEATURE:
<221> NAME/KEY: misc_feature
<222> LOCATION: (1)...(4797)
<223> OTHER INFORMATION: n = A,T,C or G

<400> SEQUENCE: 134
cctgggacca aagtgctgcc cagagctgag ggtcctggag ccacatgaga aggcttctcc     60
ctgtgtacct gtgcagcaca gggtagggtg agtccactca gctgtctagg agaggaccca    120
ggagcagcag agacncgcca agcctttact cataccatat tctgatcctt ttccagcaaa    180
ttgtggctac taatttgccc cctgaagatc aagatggctc tggggatgac tctgacaact    240
tctccggctc aggtgcaggt gaggttgtca tggggggccccc ccccacccaa gacggcaaca   300
ggtcatgcct gggggcagtg gtcaggcagt ctcctgtgtt tactgagcat gtactgagtg    360
caccctgcct gccctgtctc cacccagctg gctccaaagg gcaatgctga ggagaggaat    420
ggggtcgtga gctgctgtta aggagagctc atgcttggag gtgaggtgaa ggctgtgagc    480
tccagaaggc cccagggcgc nctgctgcac gcaggctcat attcactagg aatagcttta    540
ctcactaaga aacctctgga accccttca gaaggttatt tgactcctga gcctctattt     600
tctcatctgc aaaatgggaa taataccttg acctgataag cttgtggagc tgtaaggcag    660
cacagagcca gctgggtgt agctcttcca tccaagctcc cttccttact tcccctttcc    720
tgtggggact gggggagaga agtccctgag ctggaggtgg tcagggaagc ttcacagagg    780
aggtggctct tgagtggacc tcaggaagag gggtgagaga gctaaggaag gaggctgagg    840
tcatccctgg ggaagtgacc tagcggaggc ctgagagctg caaggtagga tatctgttgt    900
tggaagtgtc tgttgttgga agtgggggcc ttttttttcag ggagggtggg gccagagaag   960
tgtgtgccct gggataagta ggataaccac agtagttatg cccctaaggg atgcccaccc   1020 caccctgtg gtcacagaaa agctttccca ggtggcctag gcacctgtct cgtggctcca    1080
gagacaggct gcacctgaca cacacaatgg aaggacagct ctccttgtcc attttccaag   1140
gagcttagcc tcagctgcct tgtccaggta ctagcctccc tcatagcctg agcttggcca   1200
gcccaggtgc tctggagcct ccccgaccc acccaacaca ctctgcttct ggtcctcccc   1260 acccccacc tccccaacac actctgcttc tggtcctgca ggtgctttgc aagatatcac   1320
cttgtcacag cagacccct ccacttggaa ggacacgcag ctcctgacgg ctattcccac   1380
gtctccagaa cccaccggcc tggaggctac agctgcctcc acctccaccc tgccggctgg   1440 agagggccc aaggagggag aggctgtagt cctgccagaa gtggagcctg gcctcaccgc   1500
ccgggagcag gaggccaccc cccgacccag ggagaccaca cagctcccga ccactcatca   1560
ggcctcaacg accacagcca ccacggccca ggagcccgcc acctccaccc ccacaggga   1620 catgcagcct ggccaccatg agacctcaac ccctgcagga cccagccaag ctgaccttca   1680
cactccccac acagaggatg gaggtccttc tgccaccgag agggctgctg aggatggagc   1740
ctccagtcag ctcccagcag cagagggctc tggggagcag gtgagtggcc tctgcattcc   1800
```

```
ttgggaaatt gagtgggttg gtcctaatgc ctggcacttg gcaggcccta cacctgtgcc    1860
ctgcgcgatc tcgtattcct caccaggaag acagggcaca ggggccgcct tcccctaccc    1920
ccagggcctc gcagagcagg acagactaac tatgagatca gagcagaagc acccttaaag    1980
atcacccaag agagggctcc caaactcaca atccaaactt gcagccctcg tcgaagagtg    2040
aacgttatac cagtcatttt atttatagct tcgtggattt acgcttacac taaatagtct    2100
gctattcata caaaatgtgt gctttgtatc acttttttgtg atatccatgc catggtccag    2160
ccagggtccg gagttgatgt ggcaagaagg cctggctttc gggccctgtg cgatcctggt    2220
ttgggtgcat ctgagtgggt ggtggcaaag atcaggaggg caggagctgc ttctgggtct    2280
gtagtggagc tggttgctgc tgctggcggt gacctggcca acccaatctg cccctgccct    2340
cccacaggac ttcacctttg aaacctcggg ggagaatacg gctgtagtgg ccgtggagcc    2400
tgaccgccgg aaccagtccc cagtggatca ggggccacg ggggcctcac agggcctcct    2460
ggacaggaaa gaggtgctgg gagtgagtt ttctttcagg ggggtagttt ggggtgaatt    2520
gctgctgtgg ggtcagggtg gggctgacca cagccaaggc cactgctttg ggagggtctg    2580
cacgagagcc caaggagccg ctgagctgag ctggccccgt ctacctgccc tagggtcat    2640
tgccggaggc ctcgtggggc tcatcttgc tgtgtgcctg gtgggtttca tgctgtaccg    2700
catgaagaag aaggacgaag gcagctactc cttggaggag ccgaaacaag ccaacggcgg    2760
ggcctaccag aagcccacca acaggagga attctatgcc tgacgcggga gccatgcgcc    2820
ccctccgccc tgccactcac taggccccca cttgcctctt ccttgaagaa ctgcaggccc    2880
tggcctcccc tgccaccagg ccacctcccc agcattccag cccctctggt cgctcctgcc    2940
cacggagtcg tgggtgtgct gggagctcca ctctgcttct ctgacttctg cctggagact    3000
tagggcacca ggggtttctc gcataggacc tttccaccac agccagcacc tggcatcgca    3060
ccattctgac tcggtttctc caaactgaag cagcctctcc ccaggtccag ctctggaggg    3120
gagggggatc cgactgcttt ggacctaaat ggcctcatgt ggctggaaga tcctgcgggt    3180
ggggcttggg gctcacacac ctgtagcact tactggtagg accaagcatc ttgggggggt    3240
ggccgctgag tggcagggga caggagtcac tttgtttcgt ggggaggtct aatctagata    3300
tcgacttgtt tttgcacatg tttcctctag ttctttgttc atagcccagt agaccttgtt    3360
acttctgagg taagttaagt aagttgattc ggtatccccc catcttgctt ccctaatcta    3420
tggtcgggag acagcatcag ggttaagaag acttttttt tttttttaa actaggagaa    3480
ccaaatctgg aagccaaaat gtaggcttag tttgtgtgtt gtctcttgag tttgtcgctc    3540
atgtgtgcaa cagggtatgg actatctgtc tggtggcccc gttctggtgg tctgttggca    3600
ggctggccag tccaggctgc cgtggggccg ccgcctcttt caagcagtcg tgcctgtgtc    3660
catgcgctca gggccatgct gaggcctggg ccgctgccac gttggagaag cccgtgtgag    3720
aagtgaatgc tgggactcag ccttcagaca gagaggactg tagggagggc ggcaggggcc    3780
tggagatcct cctgcaggct cacgcccgtc ctcctgtggc gccgtctcca gggctgctt    3840
cctcctggaa attgacgagg ggtgtcttgg gcagagctgg ctctgagcgc ctccatccaa    3900
ggccaggttc tccgttagct cctgtggccc caccctgggc cctgggctgg aatcaggaat    3960
attttccaaa gagtgatagt ctttgctttt tggcaaaact ctacttaatc caatgggttt    4020
ttccctgtac agtagatttt ccaaatgtaa taaactttaa tataaagtag tctgtgaatg    4080
ccactgcctt cgcttcttgc ctctgtgctg tgtgtgacgt gaccggactt ttctgcaaac    4140
accaacatgt tgggaaactt ggctcgaatc tctgtgcctt cgtctttccc atggggaggg    4200
```

-continued

| | |
|---|---|
| attctggttc cagggtccct ctgtgtattt gctttttgt tttggctgaa attctcctgg | 4260 |
| aggtcggtag gttcagccaa ggtttataa ggctgatgtc aatttctgtg ttgccaagct | 4320 |
| ccaagcccat cttctaaatg gcaaaggaag gtggatggcc ccagcacagc ttgacctgag | 4380 |
| gctgtggtca cagcggaggt gtggagccga ggcctacccc ncagacacct tggacatcct | 4440 |
| cctcccaccc ggctgcagag gccaganncc agcccaggt cctgcactta cttgcttatt | 4500 |
| tgacaacgtt tcagcgactc cgttggccac tccgagagtg ggccagtctg tggatcagag | 4560 |
| atgcaccacc aagccaaggg aacctgtgtc cggtattcga tactgcgact ttctgcctgg | 4620 |
| agtgtatgac tgcacatgac tcgggggtgg ggaaagggt cggctgacca tgctcatctg | 4680 |
| ctggtccgtg ggacggtncc caagccagag gtgggttcat ttgtgtaacg acaataaacg | 4740 |
| gtacttgtca tttcgggcaa cggctgctgt ggtggtggtt gagtctcttc ttggcct | 4797 |

<210> SEQ ID NO 135
<211> LENGTH: 2856
<212> TYPE: DNA
<213> ORGANISM: Homo sapien

<400> SEQUENCE: 135

| | |
|---|---|
| tagtcgcggg tccccgagtg agcacgccag ggagcaggag accaaacgac gggggtcgga | 60 |
| gtcagagtcg cagtgggagt ccccggaccg gagcacgagc ctgagcggga gagcgccgct | 120 |
| cgcacgcccg tcgccacccg cgtacccggc gcagccagag ccaccagcgc agcgctgcca | 180 |
| tggagcccag cagcaagaag ctgacgggtc gcctcatgct ggctgtggga ggagcagtgc | 240 |
| ttggctccct gcagtttggc tacaacactg gagtcatcaa tgcccccag aaggtgatcg | 300 |
| aggagttcta caaccagaca tgggtccacc gctatgggga gagcatcctg cccaccacgc | 360 |
| tcaccacgct ctggtccctc tcagtggcca tcttttctgt tgggggcatg attggctcct | 420 |
| tctctgtggg ccttttcgtt aaccgctttg gccggcggaa ttcaatgctg atgatgaacc | 480 |
| tgctggcctt cgtgtccgcc gtgctcatgg gcttctcgaa actgggcaag tcctttgaga | 540 |
| tgctgatcct gggccgcttc atcatcggtg tgtactgcgg cctgaccaca ggcttcgtgc | 600 |
| ccatgtatgt gggtgaagtg tcacccacag cctttcgtgg ggccctgggc accctgcacc | 660 |
| agctgggcat cgtcgtcggc atcctcatcg cccaggtgtt cggcctggac tccatcatgg | 720 |
| gcaacaagga cctgtggccc ctgctgctga gcatcatctt catcccggcc ctgctgcagt | 780 |
| gcatcgtgct gccccttctgc cccgagagtc cccgcttcct gctcatcaac cgcaacgagg | 840 |
| agaaccgggc caagagtgtg ctaaagaagc tgcgcgggac agctgacgtg acccatgacc | 900 |
| tgcaggagat gaaggaagag agtcggcaga tgatgcggga gaagaaggtc accatcctgg | 960 |
| agctgttccg ctcccccgcc taccgccagc ccatcctcat cgctgtggtg ctgcagctgt | 1020 |
| cccagcagct gtctggcatc aacgctgtct ctattactc cacgagcatc ttcgagaagg | 1080 |
| cgggggtgca gcagcctgtg tatgccacca ttggctccgg tatcgtcaac acggccttca | 1140 |
| ctgtcgtgtc gctgtttgtg gtggagcgag caggccggcg gacctgcac ctcataggcc | 1200 |
| tcgctggcat ggcgggttgt gccatactca tgaccatcgc gctagcactg ctggagcagc | 1260 |
| taccctggat gtcctatctg agcatcgtgg ccatctttgg cttttgtggcc ttctttgaag | 1320 |
| tgggtcctgg ccccatccca tggttcatcg tggctgaact cttcagccag ggtccacgtc | 1380 |
| cagctgccat tgccgttgca ggcttctcca actggaccct caaatttcatt gtgggcatgt | 1440 |
| gcttccagta tgtggagcaa ctgtgtggtc cctacgtctt catcatcttc actgtgctcc | 1500 |

```
tggttctgtt cttcatcttc acctacttca aagttcctga gactaaaggc cggaccttcg    1560
atgagatcgc ttccggcttc cggcaggggg gagccagcca aagtgataag acacccgagg    1620
agctgttcca tccctgggg gctgattccc aagtgtgagt cgccccagat caccagcccg    1680
gcctgctccc agcagcccta aggatctctc aggagcacag gcagctggat gagacttcca    1740
aacctgacag atgtcagccg agccgggcct ggggctcctt tctccagcca gcaatgatgt    1800
ccagaagaat attcaggact taacggctcc aggattttaa caaaagcaag actgttgctc    1860
aaatctattc agacaagcaa caggtttat aatttttta ttactgattt tgttattttt    1920
atatcagcct gagtctcctg tgcccacatc ccaggcttca ccctgaatgg ttccatgcct    1980
gagggtggag actaagccct gtcgagacac ttgccttctt cacccagcta atctgtaggg    2040
ctggacctat gtcctaagga cacactaatc gaactatgaa ctacaaagct tctatcccag    2100
gaggtggcta tggccacccg ttctgctggc ctggatctcc ccactctagg ggtcaggctc    2160
cattaggatt tgccccttcc catctcttcc tacccaacca ctcaaattaa tctttctta    2220 cctgagacca gttgggagca ctggagtgca gggaggagag gggaagggcc agtctgggct    2280
gccgggttct agtctccttt gcactgaggg ccacactatt accatgagaa gagggcctgt    2340
gggagcctgc aaactcactg ctcaagaaga catggagact cctgccctgt tgtgtataga    2400
tgcaagatat ttatatatat ttttggttgt caatattaaa tacagacact aagttatagt    2460
atatctggac aagccaactt gtaaatacac cacctcactc ctgttactta cctaaacaga    2520
tataaatggc tggtttttag aaacatggtt ttgaaatgct tgtggattga gggtaggagg    2580
tttggatggg agtgagacag aagtaagtgg ggttgcaacc actgcaacgg cttagacttc    2640
gactcaggat ccagtccctt acacgtacct ctcatcagtg tcctcttgct caaaaatctg    2700
tttgatccct gttacccaga gaatatatac attctttatc ttgacattca aggcatttct    2760
atcacatatt tgatagttgg tgttcaaaaa aacactagtt ttgtgccagc cgtgatgctc    2820
aggcttgaaa tcgcattatt ttgaatgtga agggaa                              2856
```

<210> SEQ ID NO 136
<211> LENGTH: 356
<212> TYPE: DNA
<213> ORGANISM: Homo sapien

<400> SEQUENCE: 136

```
ggtggagcca aatgaagaaa atgaagatga aagagacaga cacctcagtt tttctggatc     60
aggcattgat gatgatgaag attttatctc cagcaccatt tcaaccacac cacgggcttt    120
tgaccacaca aaacagaacc aggactggac tcagtggaac ccaagccatt caaatccgga    180
agtgctactt cagacaacca caaggatgac tgatgtagac agaaatggca ccactgctta    240
tgaaggaaac tggaacccag aagcacaccc tcccctcatt caccatgagc atcatgagga    300
agaagagacc ccacattcta caagcacaat ccaggcaact cctagtagta caacgg        356
```

<210> SEQ ID NO 137
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 137

```
gcaggtggag aagacatttt attgttcctg ggtctctgg aggcccattg gtggggctgg       60
```

```
gtcactggct gccccggaa cagggcgctg ctccatggct ctgcttgtgg tagtctgtgg      120
ctatgtctcc cagcaaggac agaaactcag aaaaatcaat cttcttatcc tcattcttgt     180 ccttttctc aaagacatcg gcgaggtaat ttgtgccctt tttacctcgg cccgcgacca      240
cgctaaggcc aaanttccag acanayggcc gggccggtnc natagggan  cccaacttgg    300 ggacccaaac tctggcgcgg aaacacangg gcataagctt gnttcctgtg gggaaa         356
```

<210> SEQ ID NO 138
<211> LENGTH: 353
<212> TYPE: DNA
<213> ORGANISM: Homo sapien

<400> SEQUENCE: 138

```
aggtccagtc ctccacttgg cctgatgaga gtggggagtg gcaagggacg tttctcctgc      60
aatagacact tagatttctc tcttgtggga agaaaccacc tgtccatcca ctgactcttc     120
tacattgatg tggaaattgc tgctgctacc accacctcct gaagaggctt ccctgatgcc     180
aatgccagcc atcttggcat cctggccctc gagcaggctg cggtaagtag cgatctcctg    240
ctccagccgt gtctttatgt caagcagcat cttgtactcc tggttctgag cctccatctc    300
gcatcggagc tcactcagac ctcgsccgsg mssmcgctam gccgaattcc agc            353
```

<210> SEQ ID NO 139
<211> LENGTH: 371
<212> TYPE: DNA
<213> ORGANISM: Homo sapien

<400> SEQUENCE: 139

```
agcgtggtcg cggccgaggt ccatccgaag caagattgca gatggcagtg tgaagagaga      60
agacatattc tacacttcaa gctttggtg  caattcccat cgaccagagt tggtccgacc     120
agccttggaa aggtcactga aaaatcttca attggattat gttgacctct accttattca     180
ttttccagtg tctgtaaagc caggtgagga agtgatccca aaagatgaaa atggaaaaat    240
actatttgac acagtggatc tctgtgccac gtgggaggcc gtggagaagt gtaaagatgc     300
aggattggac ctgcccgggc ggccgctcga agccgaatt  ccagcacact ggcggccgtt    360
actagtggat c                                                          371
```

<210> SEQ ID NO 140
<211> LENGTH: 370
<212> TYPE: DNA
<213> ORGANISM: Homo sapien

<400> SEQUENCE: 140

```
tagcgtggtc gcggccgagg tccatctccc tttgggaact aggggctgc tggtgggaaa      60 tgggagccag ggcagatgtt gcattccttt gtgtccctgt aaatgtggga ctacaagaag    120
aggagctgcc tgagtggtac tttctcttcc tggtaatcct ctggcccagc tcatggcag     180 aatagaggta ttttttaggct atttttgtaa tatgcttct  ggtcaaaatc cctgtgtagc    240
tgaattccca agccctgcat tgtacagccc cccactcccc tcaccaccta ataaggaat     300 agttaacact caaaaaaaaa aaaaaacctg cccgggcggc cgctcgaaag ccgaattcca    360
gcacactggc                                                            370
```

<210> SEQ ID NO 141
<211> LENGTH: 371
<212> TYPE: DNA

<213> ORGANISM: Homo sapien

<400> SEQUENCE: 141

| | | | | | |
|---|---|---|---|---|---|
| tagcgtggtc | gcggccgagg | tcctctgtgc | tgcctgtcac | agcccgatgg | taccagcgca | 60 |
| gggtgtaggc | agtgcaggag | ccctcatcca | gtggcaggga | acagggtca | tcactatccc | 120 |
| aaggagcttc | aggtcctgg | tactcctcca | cagaatactc | ggagtattca | gagtactcat | 180 |
| catcctcagg | gggtacccgc | tcttcctcct | ctgcatgaga | gacgcggagc | acaggcacag | 240 |
| catggagctg | ggagccggca | gtgtctgcag | cataactagg | gagggtcgt | gatccagatg | 300 |
| cgatgaactg | gccctggcag | gcacagtgct | gactcatctc | ttggcgacct | gcccgggcgg | 360 |
| ccgctcgaag | c | | | | | 371 |

<210> SEQ ID NO 142
<211> LENGTH: 343
<212> TYPE: DNA
<213> ORGANISM: Homo sapien

<400> SEQUENCE: 142

| | | | | | |
|---|---|---|---|---|---|
| gcgttttgag | gccaatggtg | taaaaggaaa | tatcttcaca | taaaaactag | atggaagcat | 60 |
| tgtcagaaac | ctctttgtga | tgtttgcttt | caactcacag | agttgaacat | tccttttcat | 120 |
| agagcagttt | tgaaacactc | ttttgtagaa | tttgcaagcg | gatgattgga | tcgctatgag | 180 |
| gtcttcattg | gaaacgggat | acctttacat | aaaaactaga | cagtagcatt | ctcagaaatt | 240 |
| tctttgggat | gtgggcattc | aacccacaga | ggagaacttc | atttgataga | gcagttttga | 300 |
| aacacccttt | ttgtagaatc | tacaggtgga | catttagagt | gct | | 343 |

<210> SEQ ID NO 143
<211> LENGTH: 354
<212> TYPE: DNA
<213> ORGANISM: Homo sapien

<400> SEQUENCE: 143

| | | | | | |
|---|---|---|---|---|---|
| aggtctgatg | gcagaaaaac | tcagactgtc | tgcaactta | cagatggtgc | attggttcag | 60 |
| catcaggagt | gggatgggaa | ggaaagcaca | ataacaagaa | aattgaaaga | tgggaaatta | 120 |
| gtggtggagt | gtgtcatgaa | caatgtcacc | tgtactcgga | tctatgaaaa | agtagaataa | 180 |
| aaattccatc | atcactttgg | acaggagtta | attaagagaa | tgaccaagct | cagttcaatg | 240 |
| agcaaatctc | catactgttt | ctttcttttt | tttttcatta | ctgtgttcaa | ttatctttat | 300 |
| cataaacatt | ttcatgcag | ctatttcaaa | gtgtgttgga | ttaattagga | tcat | 354 |

<210> SEQ ID NO 144
<211> LENGTH: 353
<212> TYPE: DNA
<213> ORGANISM: Homo sapien

<400> SEQUENCE: 144

| | | | | | |
|---|---|---|---|---|---|
| ggtcaaggac | ctgggggacc | cccaggtcca | gcagccacat | gattctgcag | cagacaggga | 60 |
| cctagagcac | atctggatct | cagccccacc | cctggcaacc | tgcctgccta | gagaactccc | 120 |
| aagatgacag | actaagtagg | attctgccat | ttagaataat | tctggtatcc | tgggcgttgc | 180 |
| gttaagttgc | ttaactttca | ttctgtctta | cgatagtctt | cagaggtggg | aacagatgaa | 240 |
| gaaaccatgc | cccagagaag | gttaagtgac | ttcctcttta | tggagccagt | gttccaacct | 300 |
| aggttttgcct | gataccagac | ctgtggcccc | acctcccatg | caggtctctg | tgg | 353 |

<210> SEQ ID NO 145
<211> LENGTH: 371
<212> TYPE: DNA
<213> ORGANISM: Homo sapien

<400> SEQUENCE: 145

```
caggtctgtc ataaactggt ctggagtttc tgacgactcc ttgttcacca aatgcaccat      60
ttcctgagac ttgctggcct ctccgttgag tccacttggc tttctgtcct ccacagctcc     120
attgccactg ttgatcacta gcttttctt ctgcccacac cttcttcgac tgttgactgc     180
aatgcaaact gcaagaatca agccaaggc caagagggat gccaagatga tcagccattc     240
tggaatttgg ggtgtcctta taggaccaga ggttgtgttt gctccacctt cttgactccc     300
atgtgagacc tcggccgcga ccacgctaag ccgaattcca gcacactggc ggcccgttac     360
tagtggatcc g                                                         371
```

<210> SEQ ID NO 146
<211> LENGTH: 355
<212> TYPE: DNA
<213> ORGANISM: Homo sapien

<400> SEQUENCE: 146

```
ggtcctccgt cctcttccca gaggtgtcgg ggcttggccc cagcctccat cttcgtctct      60
caggatggcg agtagcagcg gctccaaggc tgaattcatt gtcggaggga aatataaact     120
ggtacgaag atcgggtctg gctccttcgg ggacatctat ttggcgatca acatcaccaa     180
cggcgaggaa gtggcagtga agctagaatc tcagaaggcc aggcatcccc agttgctgta     240
cgagagcaag ctctataaga ttcttcaagg tggggttggc atcccccaca tacggtggta     300
tggtcaggaa aaagactaca atgtactagt catggatctt ctgggaccta gcctc          355
```

<210> SEQ ID NO 147
<211> LENGTH: 355
<212> TYPE: DNA
<213> ORGANISM: Homo sapien

<400> SEQUENCE: 147

```
ggtctgttac aaaatgaaga cagacaacac aacatttact ctgtggagat atcctactca      60
tactatgcac gtgctgtgat tttgaacata actcgtccca aaaacttgtc acgatcatcc     120
tgacttttta ggttggctga tccatcaatc ttgcactcaa ctgttacttc tttcccagtg     180
ttgttaggag caaagctgac ctgaacagca accaatggct gtagataccc aacatgcagt     240
tttttcccat aatatgggaa atattttaag tctatcattc cattatgagg ataaactgct     300
acatttggta tatcttcatt ctttgaaaca caatctatcc ttggcactcc ttcag          355
```

<210> SEQ ID NO 148
<211> LENGTH: 369
<212> TYPE: DNA
<213> ORGANISM: Homo sapien

<400> SEQUENCE: 148

```
aggtctctct ccccctctcc ctctcctgcc agccaagtga agacatgctt acttccccctt      60
caccttcctt catgatgtgg gaagagtgct gcaacccagc cctagccaac accgcatgag     120
agggagtgtg ccgagggctt ctgagaaggt ttctctcaca tctagaaaga agcgcttaag     180
atgtggcagc cctcttcttt caagtggctc ttgtcctgtt gccctgggag ttctcaaatt     240
gctgcagcag cctccatcca gcctgaggat gacatcaata cacagaggaa gaagagtcag     300
```

```
gaaaagatga gagaagttac agactctcct gggcgacccc gagagcttac cattcctcag    360
acttcttca                                                             369
```

<210> SEQ ID NO 149
<211> LENGTH: 620
<212> TYPE: DNA
<213> ORGANISM: Homo sapien
<220> FEATURE:
<221> NAME/KEY: misc_feature
<222> LOCATION: (1)...(620)
<223> OTHER INFORMATION: n = A,T,C or G

<400> SEQUENCE: 149

```
actagtcaaa aatgctaaaa taatttggga gaaaatattt ttaagtagt gttatagttt       60
catgtttatc tttttattatg ttttgtgaag ttgtgtctt tcactaatta cctatactat    120
gccaatattt ccttatatct atccataaca tttatactac atttgtaana naatatgcac    180
gtgaaactta acactttata aggtaaaaat gaggtttcca anatttaata atctgatcaa    240
gttcttgtta tttccaaata gaatggactt ggtctgttaa gggctaagga gaagaggaag    300
ataaggttaa aagttgttaa tgaccaaaca ttctaaaaga aatgcaaaaa aaaagtttat    360
tttcaagcct tcgaactatt taaggaaagc aaaatcattt cctaaatgca tatcatttgt    420
gagaatttct cattaatatc ctgaatcatt catttcacta aggctcatgt tnactccgat    480
atgtctctaa gaaagtacta tttcatggtc caaacctggt tgccatantt gggtaaaggc    540
tttcccttaa gtgtgaaant atttaaaatg aaattttcct cttttaaaa attctttana    600
agggttaagg gtgttgggga                                                620
```

<210> SEQ ID NO 150
<211> LENGTH: 371
<212> TYPE: DNA
<213> ORGANISM: Homo sapien

<400> SEQUENCE: 150

```
ggtccgatca aaacctgcta cctccccaag actttactag tgccgataaa ctttctcaaa     60
gagcaaccag tatcacttcc ctgtttataa aacctctaac catctctttg ttctttgaac    120
atgctgaaaa ccacctggtc tgcatgtatg cccgaatttg yaattctttt ctctcaaatg    180
aaaattttaat tttagggatt catttctata ttttcacata tgtagtatta ttatttcctt    240
atatgtgtaa ggtgaaattt atggtatttg agtgtgcaag aaaatatatt tttaaagctt    300
tcatttttcc cccagtgaat gatttagaat tttttatgta aatatacaga atgtttttc     360
ttacttttat a                                                         371
```

<210> SEQ ID NO 151
<211> LENGTH: 4655
<212> TYPE: DNA
<213> ORGANISM: Homo sapien

<400> SEQUENCE: 151

```
gggacttgag ttctgttatc ttcttaagta gattcatatt gtaagggtct cggggtgggg     60
gggttggcaa aatcctggag ccagaagaaa ggacagcagc attgatcaat cttacagcta    120
acatgttgta cctggaaaac aatgcccaga ctcaatttag tgagccacag tacacgaacc    180
tggggctcct gaacagcatg gaccagcaga ttcagaacgg ctcctcgtcc accagtccct    240
ataacacaga ccacgcgcag aacagcgtca cggcgccctc gccctacgca cagcccagct    300
```

-continued

| | |
|---|---|
| ccaccttcga tgctctctct ccatcacccg ccatccctc caacaccgac tacccaggcc | 360 |
| cgcacagttt cgacgtgtcc ttccagcagt cgagcaccgc caagtcggcc acctggacgt | 420 |
| attccactga actgaagaaa ctctactgcc aaattgcaaa gacatgcccc atccagatca | 480 |
| aggtgatgac cccacctcct cagggagctg ttatccgcgc catgcctgtc tacaaaaaag | 540 |
| ctgagcacgt cacggaggtg gtgaagcggt gccccaacca tgagctgagc cgtgaattca | 600 |
| acgagggaca gattgcccct yctagtcatt tgattcgagt agaggggaac agccatgccc | 660 |
| agtatgtaga agatcccatc acaggaagac agagtgtgct ggtaccttat gagccacccc | 720 |
| aggttggcac tgaattcacg acagtcttgt acaatttcat gtgtaacagc agttgtgttg | 780 |
| gagggatgaa ccgccgtcca attttaatca ttgttactct ggaaaccaga gatgggcaag | 840 |
| tcctgggccg acgctgcttt gaggcccgga tctgtgcttg cccaggaaga gacaggaagg | 900 |
| cggatgaaga tagcatcaga aagcagcaag tttcggacag tacaaagaac ggtgatggta | 960 |
| cgaagcgccc gtttcgtcag aacacacatg gtatccagat gacatccatc aagaaacgaa | 1020 |
| gatccccaga tgatgaactg gtatacttac cagtgagggg ccgtgagact tatgaaatgc | 1080 |
| tggtgaagat caaagagtcc ctggaactca tgcagtacct tcttcagcac acaattgaaa | 1140 |
| cgtacaggca acagcaacag cagcagcacc agcacttact tcagaaacag acctcaatac | 1200 |
| agtctccatc ttcatatggt aacagctccc cacctctgaa caaatgaac agcatgaaca | 1260 |
| agctgccttc tgtgagccag cttatcaacc ctcagcagcg caacgccctc actcctacaa | 1320 |
| ccattcctga tggcatggga gccaacattc ccatgatggg cacccacatg ccaatggctg | 1380 |
| gagacatgaa tggactcagc cccacccagg cactccctcc cccactctcc atgccatcca | 1440 |
| cctcccactg cacaccccca cctccgtatc cacagattg cagcattgtc agtttcttag | 1500 |
| cgaggttggg ctgttcatca tgtctggact atttcacgac ccagggctg accaccatct | 1560 |
| atcagattga gcattactcc atggatgatc tggcaagtct gaaaatccct gagcaatttc | 1620 |
| gacatgcgat ctggaagggc atcctggacc accggcagct ccacgaattc tcctcccctt | 1680 |
| ctcatctcct gcggaccca agcagtgcct ctacagtcag tgtgggctcc agtgagaccc | 1740 |
| ggggtgagcg tgttattgat gctgtgcgat tcaccctccg ccagaccatc tctttcccac | 1800 |
| cccgagatga gtggaatgac ttcaactttg acatggatgc tcgccgcaat aagcaacagc | 1860 |
| gcatcaaaga ggaggggag tgagcctcac catgtgagct cttcctatcc ctctcctaac | 1920 |
| tgccagcccc ctaaaagcac tcctgcttaa tcttcaaagc cttctcccta gctcctcccc | 1980 |
| ttcctcttgt ctgatttctt aggggaagga gaagtaagag gcttacttct taccctaacc | 2040 |
| atctgacctg gcatctaatt ctgattctgg ctttaagcct tcaaaactat agcttgcaga | 2100 |
| actgtagctt gccatggcta ggtagaagtg agcaaaaaag agttgggtgt ctccttaagc | 2160 |
| tgcagagatt tctcattgac tttataaag catgttcacc cttatagtct aagactatat | 2220 |
| atataaatgt ataaatatac agtatagatt tttgggtggg gggcattgag tattgtttaa | 2280 |
| aatgtaattt aaatgaaaga aaattgagtt gcacttattg accatttttt aatttacttg | 2340 |
| ttttggatgg cttgtctata ctccttccct taagggtat catgtatggt gataggtatc | 2400 |
| tagagcttaa tgctacatgt gagtgacgat gatgtacaga ttctttcagt tctttggatt | 2460 |
| ctaaatacat gccacatcaa acctttgagt agatccattt ccattgctta ttatgtaggt | 2520 |
| aagactgtag atatgtattc ttttctcagt gttggtatat tttatattac tgacatttct | 2580 |
| tctagtgatg atggttcacg ttggggtgat ttaatccagt tataagaaga agttcatgtc | 2640 |
| caaacgtcct ctttagtttt tggttgggaa tgaggaaaat tcttaaaagg cccatagcag | 2700 |

-continued

```
ccagttcaaa aacacccgac gtcatgtatt tgagcatatc agtaaccccc ttaaatttaa    2760
taccagatac cttatcttac aatattgatt gggaaaacat ttgctgccat tacagaggta    2820
ttaaaactaa atttcactac tagattgact aactcaaata cacatttgct actgttgtaa    2880
gaattctgat tgatttgatt gggatgaatg ccatctatct agttctaaca gtgaagtttt    2940
actgtctatt aatattcagg gtaaatagga atcattcaga aatgttgagt ctgtactaaa    3000
cagtaagata tctcaatgaa ccataaattc aactttgtaa aaatcttttg aagcatagat    3060
aatattgttt ggtaaatgtt tcttttgttt ggtaaatgtt tcytttaaag accctcctat    3120
tctataaaac tctgcatgta gaggcttgtt tacctttctc tctctaaggt ttacaatagg    3180
agtggtgatt tgaaaaatat aaaattatga gattggtttt cctgtggcat aaattgcatc    3240
actgtatcat tttctttttt aaccggtaag agtttcagtt tgttggaaag taactgtgag    3300
aacccagttt cccgtccatc tcccttaggg actacccata gacatgaaag gtccccacag    3360
agcaagagat aagtctttca tggctgctgt tgcttaaacc acttaaacga agagttccct    3420
tgaaactttg ggaaaacatg ttaatgacaa tattccagat ctttcagaaa tataacacat    3480
ttttttgcat gcatgcaaat gagctctgaa atcttcccat gcattctggt caagggctgt    3540
cattgcacat aagcttccat tttaatttta aagtgcaaaa gggccagcgt ggctctaaaa    3600
ggtaatgtgt ggattgcctc tgaaaagtgt gtatatattt tgtgtgaaat tgcatacttt    3660
gtattttgat tatttttttt ttcttcttgg gatagtggga tttccagaac cacacttgaa    3720 acctttttttt atcgttttg tatttttcatg aaaataccat ttagtaagaa taccacatca    3780
aataagaaat aatgctacaa ttttaagagg ggagggaagg gaaagttttt tttttttatta    3840 ttttttttaaa attttgtatg ttaaagaaa tgagtccttg atttcaaagt tttgttgtac    3900
ttaaatggta ataagcactg taaacttctg caacaagcat gcagctttgc aaacccatta    3960 agggaagaa tgaaagctgt tccttggtcc tagtaagaag acaaactgct tcccttactt    4020
tgctgagggt ttgaataaac ctaggacttc cgagctatgt cagtactatt caggtaacac    4080
tagggccttg gaaatccctg tactgtgtct catggatttg gcactagcca aagcgaggca    4140
ccccttactg gcttacctcc tcatggcagc ctactctcct tgagtgtatg agtagccagg    4200 gtaagggta aaggatagt aagcatagaa accactagaa agtgggctta atggagttct    4260
tgtggcctca gctcaatgca gttagctgaa gaattgaaaa gttttgttt ggagacgttt    4320 ataaacagaa atggaaagca gagttttcat taaatccttt tactttttt tttcttggt    4380 aatcccctaa aataacagta tgtgggatat tgaatgttaa agggatattt ttttctatta    4440
tttttataat tgtacaaaat taagcaaatg ttaaaagttt tatatgcttt attaatgttt    4500
tcaaaaggta ttatacatgt gatacatttt ttaagcttca gttgcttgtc ttctggtact    4560
ttctgttatg ggcttttggg gagccagaag ccaatctaca atctcttttt gtttgccagg    4620
acatgcaata aaatttaaaa aataaataaa aacta                               4655
```

<210> SEQ ID NO 152
<211> LENGTH: 586
<212> TYPE: PRT
<213> ORGANISM: Homo sapien

<400> SEQUENCE: 152

```
Met Leu Tyr Leu Glu Asn Asn Ala Gln Thr Gln Phe Ser Glu Pro Gln
 1               5                  10                  15

Tyr Thr Asn Leu Gly Leu Leu Asn Ser Met Asp Gln Gln Ile Gln Asn
```

-continued

```
                    20                  25                  30
Gly Ser Ser Ser Thr Ser Pro Tyr Asn Thr Asp His Ala Gln Asn Ser
                35                  40                  45
Val Thr Ala Pro Ser Pro Tyr Ala Gln Pro Ser Ser Thr Phe Asp Ala
 50                  55                  60
Leu Ser Pro Ser Pro Ala Ile Pro Ser Asn Thr Asp Tyr Pro Gly Pro
 65                  70                  75                  80
His Ser Phe Asp Val Ser Phe Gln Gln Ser Ser Thr Ala Lys Ser Ala
                85                  90                  95
Thr Trp Thr Tyr Ser Thr Glu Leu Lys Lys Leu Tyr Cys Gln Ile Ala
               100                 105                 110
Lys Thr Cys Pro Ile Gln Ile Lys Val Met Thr Pro Pro Gln Gly
               115                 120                 125
Ala Val Ile Arg Ala Met Pro Val Tyr Lys Lys Ala Glu His Val Thr
               130                 135                 140
Glu Val Val Lys Arg Cys Pro Asn His Glu Leu Ser Arg Glu Phe Asn
145                 150                 155                 160
Glu Gly Gln Ile Ala Pro Ser Ser His Leu Ile Arg Val Glu Gly Asn
                   165                 170                 175
Ser His Ala Gln Tyr Val Glu Asp Pro Ile Thr Gly Arg Gln Ser Val
               180                 185                 190
Leu Val Pro Tyr Glu Pro Pro Gln Val Gly Thr Glu Phe Thr Thr Val
               195                 200                 205
Leu Tyr Asn Phe Met Cys Asn Ser Ser Cys Val Gly Gly Met Asn Arg
               210                 215                 220
Arg Pro Ile Leu Ile Ile Val Thr Leu Glu Thr Arg Asp Gly Gln Val
225                 230                 235                 240
Leu Gly Arg Arg Cys Phe Glu Ala Arg Ile Cys Ala Cys Pro Gly Arg
                   245                 250                 255
Asp Arg Lys Ala Asp Glu Asp Ser Ile Arg Lys Gln Gln Val Ser Asp
                   260                 265                 270
Ser Thr Lys Asn Gly Asp Gly Thr Lys Arg Pro Phe Arg Gln Asn Thr
               275                 280                 285
His Gly Ile Gln Met Thr Ser Ile Lys Lys Arg Arg Ser Pro Asp Asp
               290                 295                 300
Glu Leu Val Tyr Leu Pro Val Arg Gly Arg Glu Thr Tyr Glu Met Leu
305                 310                 315                 320
Val Lys Ile Lys Glu Ser Leu Glu Leu Met Gln Tyr Leu Leu Gln His
                   325                 330                 335
Thr Ile Glu Thr Tyr Arg Gln Gln Gln Gln Gln His Gln His Leu
               340                 345                 350
Leu Gln Lys Gln Thr Ser Ile Gln Ser Pro Ser Ser Tyr Gly Asn Ser
               355                 360                 365
Ser Pro Pro Leu Asn Lys Met Asn Ser Met Asn Lys Leu Pro Ser Val
   370                 375                 380
Ser Gln Leu Ile Asn Pro Gln Gln Arg Asn Ala Leu Thr Pro Thr Thr
385                 390                 395                 400
Ile Pro Asp Gly Met Gly Ala Asn Ile Pro Met Met Gly Thr His Met
                   405                 410                 415
Pro Met Ala Gly Asp Met Asn Gly Leu Ser Pro Thr Gln Ala Leu Pro
                   420                 425                 430
Pro Pro Leu Ser Met Pro Ser Thr Ser His Cys Thr Pro Pro Pro Pro
               435                 440                 445
```

-continued

```
Tyr Pro Thr Asp Cys Ser Ile Val Ser Phe Leu Ala Arg Leu Gly Cys
    450                 455                 460
Ser Ser Cys Leu Asp Tyr Phe Thr Thr Gln Gly Leu Thr Thr Ile Tyr
465                 470                 475                 480
Gln Ile Glu His Tyr Ser Met Asp Asp Leu Ala Ser Leu Lys Ile Pro
                485                 490                 495
Glu Gln Phe Arg His Ala Ile Trp Lys Gly Ile Leu Asp His Arg Gln
            500                 505                 510
Leu His Glu Phe Ser Ser Pro Ser His Leu Leu Arg Thr Pro Ser Ser
        515                 520                 525
Ala Ser Thr Val Ser Val Gly Ser Ser Glu Thr Arg Gly Glu Arg Val
    530                 535                 540
Ile Asp Ala Val Arg Phe Thr Leu Arg Gln Thr Ile Ser Phe Pro Pro
545                 550                 555                 560
Arg Asp Glu Trp Asn Asp Phe Asn Phe Asp Met Asp Ala Arg Arg Asn
                565                 570                 575
Lys Gln Gln Arg Ile Lys Glu Glu Gly Glu
            580                 585
```

<210> SEQ ID NO 153
<211> LENGTH: 2007
<212> TYPE: DNA
<213> ORGANISM: Homo sapien

<400> SEQUENCE: 153

```
gaattcgtcg ctgctccagg gaaagttctg ttactccact gactctctct tttcctgata    60
acatggccag caagaaagta attacagtgt tggagcaac aggagctcaa ggtggctctg    120
tggccagggc aattttggag agcaaaaaat ttgcagtgag agcagtgacc agggatgtga   180
cttgaccaaa tgccctggag ctccagcgcc ttggagctga ggtggtcaaa ggtgacctga   240
atgataaagc atcggtggac agtgccttaa aaggtgtcta tggggccttc ttggtgacca   300
acttctggga ccctctcaac caagataagg aagtgtgtcg ggggaagctg gtggcagact   360
ccgccaagca cctgggtctg aagcacgtgg tgtacagcgg cctggagaac gtcaagcgac   420
tgacggatgg caagctggag gtgccgcact tgacagcaa gggcgaggtg gaggagtact   480
tctggtccat tggcatcccc atgaccagtg tccgcgtggc ggcctacttt gaaaactttc   540
tcgcggcgtg gcggcccgtg aaagcctctg atggagatta ctacaccttg gctgtaccga   600
tgggagatgt accaatggat ggtatctctg ttgctgatat tggagcagcc gtctctagca   660
ttttaattc tccagaggaa tttttaggca aggccgtggg gctcagtgca gaagcactaa   720
caatacagca atatgctgat gttttgtcca aggctttggg gaaagaagtc cgagatgcaa   780
agattacccc ggaagctttc gagaagctgg gattccctgc agcaaaggaa atagccaata   840
tgtgtcgttt ctatgaaatg aagccagacc gagatgtcaa tctcacccac caactaaatc   900
ccaaagtcaa aagcttcagc cagtttatct cagagaacca gggagccttc aagggcatgt   960
agaaaatcag ctgttcagat aggcctctgc accacacagc tctttcctc tctgatcctt  1020
ttcctcttta cggcacaaca ttcatgttga cagaacatgc tggaatgcaa ttgtttgcaa  1080
caccgaagga tttcctgcgg tcgcctcttc agtaggaagc actgcattgg tgataggaca  1140
cggtaatttg attcacattt aacttgctag ttagtgataa gggtggtaca actgtttggt  1200
aaaatgagaa gcctcggaac ttggagcttc tctcctacca ctaatgggag ggcagattat  1260
actgggattt ctcctgggtg agtaatttca agccctaatg ctgaaattcc cctaggcagc  1320
```

-continued

| | |
|---|---|
| tccagttttc tcaactgcat tgcaaaattc ccagtgaact tttaagtact tttaacttaa | 1380 |
| aaaaatgaac atctttgtag agaattttct ggggaacatg gtgttcaatg aacaagcaca | 1440 |
| agcattggaa atgctaaaat tcagttttgc ctcaagattg gaagtttatt ttctgactca | 1500 |
| ttcatgaagt catctattga gccaccattc aattattcat ctattaattc cttgatcctt | 1560 |
| catttatcca ttctgcaaac ttttcttgag caccagcacg gtggccatt tgtggacttc | 1620 |
| tcttcattcc tatgtgtttt cttatcaaag tgatccactc tcgaaaggct cctttccagt | 1680 |
| ctgtggttgg gttcaagtca tgccagggcc agggggccca tctcctcgtt tagctctagg | 1740 |
| caaaatccag gggatctgca gtggggagcg ggggcaggaa gctggaggga aggcctgtga | 1800 |
| agggtaggga tgtggaaaga caaggtgaca gaaggaccca ataggacctt tctatatctc | 1860 |
| tggcttagca ttttctacat catattgtaa tcgtcttatt tgctagtttt cttccttact | 1920 |
| gtgagtgact aacagtcatc tttatcccag tgcctggtac ataataagtg atcaataaat | 1980 |
| gttgattgac taaaaaaaaa aaaaaaa | 2007 |

<210> SEQ ID NO 154
<211> LENGTH: 2148
<212> TYPE: DNA
<213> ORGANISM: Homo sapien

<400> SEQUENCE: 154

| | |
|---|---|
| gaattcgtcg ctgctccagg gaaagttctg ttactccact gactctctct tttcctgata | 60 |
| acatggccag caagaaagta attacagtgt ttggagcaac aggagctcaa ggtggctctg | 120 |
| tggccagggc aattttggag agcaaaaaat ttgcagtgag agcagtgacc agggatgtga | 180 |
| cttgaccaaa tgccctggag ctccagcgcc ttggagctga ggtggtcaaa ggtgacctga | 240 |
| atgataaagc atcggtggac agtgccttaa aaggggaagc tggtggcaga ctccgccaag | 300 |
| cacctgggtc tgaagcacgt ggtgtacagc ggcctggaga acgtcaagcg actgacggat | 360 |
| ggcaagctgg aggtgccgca ctttgacagc aagggcgagg tggaggagta cttctggtcc | 420 |
| attggcatcc ccatgaccag tgtccgcgtg gcggcctact tgaaaacttt ctcgcggcg | 480 |
| tggcggcccg tgaaagcctc tgatggagat tactacacct tggctgtacc gatgggagat | 540 |
| gtaccaatgg atggtatctc tgttgctgat attggagcag ccgtctctag cattttttaat | 600 |
| tctccagagg aattttttagg caaggccgtg gggctcagtg cagaagcact aacaatacag | 660 |
| caatatgctg atgttttgtc caaggctttg gggaaagaag tccgagatgc aaagactatc | 720 |
| tgtgctatag atgaccagaa aacagtggaa gaaggtttca tggaagacgt gggcttgagt | 780 |
| tggtccttga gggaacatga ccatgtatag acagaggagg catcaagaag gctggcctgg | 840 |
| ctaattctgg aataaacacg acaaaccaga ggcagtacgg gaaggaggca aattctggct | 900 |
| ctgcctctat ccttgattac cccggaagct ttcgagaagc tgggattccc tgcagcaaag | 960 |
| gaaatagcca atatgtgtcg tttctatgaa atgaagccag accgagatgt caatctcacc | 1020 |
| caccaactaa atcccaaagt caaaagcttc agccatttta tctcagagaa ccagggagcc | 1080 |
| ttcaagggca tgtagaaaat cagctgttca gataggcctc tgcaccacac agcctctttc | 1140 |
| ctctctgatc cttttcctct ttacggcaca acattcatgt tgacagaaca tgctggaatg | 1200 |
| caattgtttg caacaccgaa ggatttcctg cggtcgcctc ttcagtagga agcactgcat | 1260 |
| tggtgatagg acacggtaat ttgattcaca tttaacttgc tagttagtga taagggtggt | 1320 |
| acaactgttt ggtaaaatga gaagcctcgg aacttggagc ttctctccta ccactaatgg | 1380 |

```
gagggcagat tatactggga tttctcctgg gtgagtaatt tcaagcccta atgctgaaat    1440 tccctaggc  agctccagtt ttctcaactg cattgcaaaa ttcccagtga acttttaagt    1500
acttttaact taaaaaaatg aacatctttg tagagaattt tctggggaac atggtgttca    1560
atgaacaagc acaagcattg gaaatgctaa aattcagttt tgcctcaaga ttggaagttt    1620
attttctgac tcattcatga agtcatctat tgagccacca ttcaattatt catctattaa    1680
ttccttgatc cttcatttat ccattctgca aactttttctt gagcaccagc acgggtggcc   1740
atttgtggac ttctcttcat tcctatgtgt tttcttatca aagtgatcca ctctcgaaag    1800
gctcctttcc agtctgtggt tgggttcaag tcatgccagg ccaggggggc ccatctcctc    1860
gtttagctct aggcaaaatc caggggatct gcagtgggga gcgggggcag gaagctggag    1920
ggaaggcctg tgaagggtag ggatgtgaaa agacaaggtg acagaaggac ccaataggac    1980
ctttctatat ctctggctta gcattttcta catcatattg taatcgtctt atttgctagt    2040
tttcttcctt actgtgagtg actaacagtc atctttatcc cagtgcctgg tacataataa    2100
gtgatcaata aatgttgatt gactaaatga aaaaaaaaaa aaaaaaa                  2148
```

<210> SEQ ID NO 155  
<211> LENGTH: 153  
<212> TYPE: PRT  
<213> ORGANISM: Homo sapien

<400> SEQUENCE: 155

```
Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
        35                  40                  45

Ala Ala Val Ser Ser Ile Phe Asn Ser Pro Glu Glu Phe Leu Gly Lys
    50                  55                  60

Ala Val Gly Leu Ser Ala Glu Ala Leu Thr Ile Gln Gln Tyr Ala Asp
65                  70                  75                  80

Val Leu Ser Lys Ala Leu Gly Lys Glu Val Arg Asp Ala Lys Ile Thr
                85                  90                  95

Pro Glu Ala Phe Glu Lys Leu Gly Phe Pro Ala Ala Lys Glu Ile Ala
            100                 105                 110

Asn Met Cys Arg Phe Tyr Glu Met Lys Pro Asp Arg Asp Val Asn Leu
        115                 120                 125

Thr His Gln Leu Asn Pro Lys Val Lys Ser Phe Ser Gln Phe Ile Ser
    130                 135                 140

Glu Asn Gln Gly Ala Phe Lys Gly Met
145                 150
```

<210> SEQ ID NO 156  
<211> LENGTH: 128  
<212> TYPE: PRT  
<213> ORGANISM: Homo sapien

<400> SEQUENCE: 156

```
Met Thr Ser Val Arg Val Ala Ala Tyr Phe Glu Asn Phe Leu Ala Ala
 1               5                  10                  15

Trp Arg Pro Val Lys Ala Ser Asp Gly Asp Tyr Tyr Thr Leu Ala Val
            20                  25                  30

Pro Met Gly Asp Val Pro Met Asp Gly Ile Ser Val Ala Asp Ile Gly
```

|  |  |  | 35 |  |  |  | 40 |  |  |  | 45 |  |
|---|---|---|---|---|---|---|---|---|---|---|---|---|

Ala Ala Val Ser Ser Ile Phe Asn Ser Pro Glu Glu Phe Leu Gly Lys
    50                    55                    60

Ala Val Gly Leu Ser Ala Glu Ala Leu Thr Ile Gln Gln Tyr Ala Asp
65                  70                    75                    80

Val Leu Ser Lys Ala Leu Gly Lys Glu Val Arg Asp Ala Lys Thr Ile
                85                    90                    95

Cys Ala Ile Asp Asp Gln Lys Thr Val Glu Gly Phe Met Glu Asp
            100                  105                110

Val Gly Leu Ser Trp Ser Leu Arg Glu His Asp His Val Ala Gly Ala
            115                  120                125

```
<210> SEQ ID NO 157
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 157
ctgcagcccg gggatccac tagtccagtg tggtggaatt cattggtctt tacaagactt      60
ggatacatta cagcagacat ggaaatataa ttttaaaaaa tttctctcca acctccttca    120
aattcagtca ccactgttat attaccttct ccaggaaccc tccagtgggg aaggctgcga    180
tattagattt ccttgtatgc aaagtttttg ttgaaagctg tgctcagagg aggtgagagg    240
agaggaagga gaaaactgca tcataacttt acagaattga atctagagtc ttccccgaaa    300
agcccagaaa cttctctgcn gnatctggct tgtccatctg gtctaaggtg gctgcttctt    360
ccccagccat cgagtcagtt tgtgcccatg aataatacac gacctgctat ttcccatgac    420
tgct                                                                  424

<210> SEQ ID NO 158
<211> LENGTH: 2099
<212> TYPE: DNA
<213> ORGANISM: Homo sapien

<400> SEQUENCE: 158
ccgcggttaa aaggcgcagc aggtgggagc cggggccttc acccgaaacc cgacgagagc     60
ccgacagccg gcggcgcccg agcccgacct gcctgcccag ccggagcgaa gggcgccgcc    120
ccgcgcagag cccgcgccag ggccgccggc cgcagagcag ttaaaacgtg caggcaccag    180
aaggcacttc ctgtcggtga agaagacctg tctccggtgt cacgggcatc ctgtgttttg    240 caaacgggc tgacctccct tcctggggag caggaagggt cagggaagga aagaagtac    300 agaagatctg gctaaacaat ttctgtatgg cgaaagaaaa attctaactt gtacgccctc    360
ttcatgcatc tttaattcaa tttgaatatt ccaggcgaca tcctcactga ccgagcaaag    420
attgacattc gtatcatcac tgtgcaccat tggcttctag gcactccagt ggggtaggag    480
aaggaggtct gaaaccctcg cagagggatc ttgccctcat tctttgggtc tgaaacactg    540
gcagtcgttg gaaacaggac tcagggataa accagcgcaa tggattgggg gacgctgcac    600
actttcatcg ggggtgtcaa caaacactcc accagcatcg ggaaggtgtg gatcacagtc    660
atctttattt tccgagtcat gatcctcgtg gtggctgccc aggaagtgtg gggtgacgag    720
caagaggact tcgtctgcaa cacactgcaa ccgggatgca aaaatgtgtg ctatgaccac    780
```

```
tttttcccgg tgtcccacat ccggctgtgg gccctccagc tgatcttcgt ctccacccca    840
gcgctgctgg tggccatgca tgtggcctac tacaggcacg aaaccactcg caagttcagg    900
cgaggagaga agaggaatga tttcaaagac atagaggaca ttaaaaagca gaaggttcgg    960 atagagggt cgctgtggtg gacgtacacc agcagcatct ttttccgaat catctttgaa     1020
gcagccttta tgtatgtgtt ttacttcctt tacaatgggt accacctgcc ctgggtgttg    1080
aaatgtggga ttgacccctg ccccaacctt gttgactgct ttatttctag gccaacagag    1140
aagaccgtgt ttaccatttt tatgatttct gcgtctgtga tttgcatgct gcttaacgtg    1200
gcagagttgt gctacctgct gctgaaagtg tgttttagga gatcaaagag agcacagacg    1260
caaaaaaatc accccaatca tgccctaaag gagagtaagc agaatgaaat gaatgagctg    1320
atttcagata gtggtcaaaa tgcaatcaca ggttcccaag ctaaacattt caaggtaaaa    1380
tgtagctgcg tcataaggag acttctgtct tctccagaag gcaataccaa cctgaaagtt    1440
ccttctgtag cctgaagagt ttgtaaatga ctttcataat aaatagacac ttgagttaac    1500
tttttgtagg atacttgctc cattcataca caacgtaatc aaatatgtgg tccatctctg    1560
aaaacaagag actgcttgac aaaggagcat tgcagtcact ttgacaggtt cctttaagt     1620 ggactctctg acaaagtggg tactttctga aaatttatat aactgttgtt gataaggaac    1680
atttatccag gaattgatac gtttattagg aaaagatatt tttataggct tggatgtttt    1740
tagttctgac tttgaattta tataaagtat ttttataatg actggtcttc cttacctgga    1800
aaaacatgcg atgttagttt tagaattaca ccacaagtat ctaaatttgg aacttacaaa    1860
gggtctatct tgtaaatatt gttttgcatt gtctgttggc aaatttgtga actgtcatga    1920
tacgcttaag gtggaaagtg ttcattgcac aatatatttt tactgctttc tgaatgtaga    1980
cggaacagtg tggaagcaga aggcttttt aactcatccg tttgccaatc attgcaaaca     2040
actgaaatgt ggatgtgatt gcctcaataa agctcgtccc cattgcttaa aaaaaaaa     2099
```

<210> SEQ ID NO 159  
<211> LENGTH: 291  
<212> TYPE: PRT  
<213> ORGANISM: Homo sapien

<400> SEQUENCE: 159

```
Met Asp Trp Gly Thr Leu His Thr Phe Ile Gly Val Asn Lys His
  1               5                  10                  15

Ser Thr Ser Ile Gly Lys Val Trp Ile Thr Val Ile Phe Ile Phe Arg
             20                  25                  30

Val Met Ile Leu Val Val Ala Ala Gln Glu Val Trp Gly Asp Glu Gln
         35                  40                  45

Glu Asp Phe Val Cys Asn Thr Leu Gln Pro Gly Cys Lys Asn Val Cys
     50                  55                  60

Tyr Asp His Phe Phe Pro Val Ser His Ile Arg Leu Trp Ala Leu Gln
 65                  70                  75                  80

Leu Ile Phe Val Ser Thr Pro Ala Leu Leu Val Ala Met His Val Ala
                 85                  90                  95

Tyr Tyr Arg His Glu Thr Thr Arg Lys Phe Arg Arg Gly Glu Lys Arg
            100                 105                 110

Asn Asp Phe Lys Asp Ile Glu Asp Ile Lys Lys Gln Lys Val Arg Ile
        115                 120                 125

Glu Gly Ser Leu Trp Trp Thr Tyr Thr Ser Ser Ile Phe Phe Arg Ile
    130                 135                 140
```

```
Ile Phe Glu Ala Ala Phe Met Tyr Val Phe Tyr Phe Leu Tyr Asn Gly
145                 150                 155                 160

Tyr His Leu Pro Trp Val Leu Lys Cys Gly Ile Asp Pro Cys Pro Asn
                165                 170                 175

Leu Val Asp Cys Phe Ile Ser Arg Pro Thr Glu Lys Thr Val Phe Thr
            180                 185                 190

Ile Phe Met Ile Ser Ala Ser Val Ile Cys Met Leu Leu Asn Val Ala
        195                 200                 205

Glu Leu Cys Tyr Leu Leu Lys Val Cys Phe Arg Arg Ser Lys Arg
    210                 215                 220

Ala Gln Thr Gln Lys Asn His Pro Asn His Ala Leu Lys Glu Ser Lys
225                 230                 235                 240

Gln Asn Glu Met Asn Glu Leu Ile Ser Asp Ser Gly Gln Asn Ala Ile
                245                 250                 255

Thr Gly Ser Gln Ala Lys His Phe Lys Val Lys Cys Ser Cys Val Ile
            260                 265                 270

Arg Arg Leu Leu Ser Ser Pro Glu Gly Asn Thr Asn Leu Lys Val Pro
        275                 280                 285

Ser Val Ala
    290

<210> SEQ ID NO 160
<211> LENGTH: 3951
<212> TYPE: DNA
<213> ORGANISM: Homo sapien

<400> SEQUENCE: 160
tctgcatcca tattgaaaac ctgacacaat gtatgcagca ggctcagtgt gagtgaactg      60
gaggcttctc tacaacatga cccaaaggag cattgcaggt cctatttgca acctgaagtt     120
tgtgactctc ctggttgcct taagttcaga actcccattc ctgggagctg agtacagct     180
tcaagacaat gggtataatg gattgctcat tgcaattaat cctcaggtac ctgagaatca     240
gaacctcatc tcaaacatta ggaaatgat aactgaagct tcattttacc tatttaatgc      300
taccaagaga agagtatttt tcagaaatat aaagatttta atacctgcca catggaaagc     360
taataataac agcaaaataa acaagaatc atatgaaaag gcaaatgtca tagtgactga      420
ctggtatggg gcacatggag atgatccata caccctacaa tacagagggt gtggaaaaga     480
gggaaaatac attcatttca cacctaattt cctactgaat gataacttaa cagctggcta     540
cggatcacga ggccgagtgt ttgtccatga atgggcccac ctccgttggg gtgtgttcga     600
tgagtataac aatgacaaac ctttctacat aaatgggcaa atcaaatta aagtgacaag      660
gtgttcatct gacatcacag gcattttgt gtgtgaaaaa ggtccttgcc cccaagaaaa     720
ctgtattatt agtaagcttt ttaaagaagg atgcaccttt atctacaata gcacccaaaa     780
tgcaactgca tcaataatgt tcatgcaaag tttatcttct gtggttgaat tttgtaatgc      840
aagtacccac aaccaagaag caccaaacct acagaaccag atgtgcagcc tcagaagtgc     900
atgggatgta atcacagact ctgctgactt tcaccacagc tttcccatga cgggactga      960
gcttccacct cctcccacat tctcgcttgt agaggctggt gacaaagtgg tctgtttagt    1020
gctggatgtg tccagcaaga tggcagaggc tgacagactc cttcaactac aacaagccgc    1080
agaattttat ttgatgcaga ttgttgaaat tcataccttc gtgggcattg ccagtttcga    1140
cagcaaagga gagatcagag cccagctaca ccaaattaac agcaatgatg atcgaaagtt    1200
gctggttca tatctgccca ccactgtatc agctaaaaca gacatcagca tttgttcagg     1260
```

```
gcttaagaaa ggatttgagg tggttgaaaa actgaatgga aaagcttatg gctctgtgat    1320
gatattagtg accagcggag atgataagct tcttggcaat tgcttaccca ctgtgctcag    1380
cagtggttca acaattcact ccattgccct gggttcatct gcagcccaa atctggagga    1440 attatcacgt cttacaggag gtttaaagtt ctttgttcca gatatatcaa actccaatag    1500
catgattgat gctttcagta gaatttcctc tggaactgga gacattttcc agcaacatat    1560
tcagcttgaa agtacaggtg aaaatgtcaa acctcaccat caattgaaaa acacagtgac    1620
tgtggataat actgtgggca acgacactat gtttctagtt acgtggcagg ccagtggtcc    1680
tcctgagatt atattatttg atcctgatgg acgaaaatac tacacaaata attttatcac    1740
caatctaact tttcggacag ctagtctttg gattccagga acagctaagc ctgggcactg    1800
gacttacacc ctgaacaata cccatcattc tctgcaagcc ctgaaagtga cagtgacctc    1860
tcgcgcctcc aactcagctg tgccccagc cactgtggaa gcctttgtgg aaagagacag    1920
cctccatttt cctcatcctg tgatgattta tgccaatgtg aaacagggat tttatcccat    1980
tcttaatgcc actgtcactg ccacagttga gccagagact ggagatcctg ttacgctgag    2040
actccttgat gatggagcag gtgctgatgt tataaaaaat gatggaattt actcgaggta    2100
ttttttctcc tttgctgcaa atggtagata tagcttgaaa gtgcatgtca atcactctcc    2160
cagcataagc accccagccc actctattcc agggagtcat gctatgtatg taccaggtta    2220
cacagcaaac ggtaatattc agatgaatgc tccaaggaaa tcagtaggca gaaatgagga    2280
ggagcgaaag tggggcttta gccgagtcag ctcaggaggc tccttttcag tgctgggagt    2340
tccagctggc ccccaccctg atgtgtttcc accatgcaaa attattgacc tggaagctgt    2400
aaaagtagaa gaggaattga ccctatcttg gacagcacct ggagaagact ttgatcaggg    2460
ccaggctaca agctatgaaa taagaatgag taaaagtcta cagaatatcc aagatgactt    2520
taacaatgct atttagtaa atacatcaaa gcgaaatcct cagcaagctg gcatcaggga    2580
gatatttacg ttctcacccc aaatttccac gaatggacct gaacatcagc caaatggaga    2640
aacacatgaa agccacagaa tttatgttgc aatacgagca atggatagga actccttaca    2700
gtctgctgta tctaacattg cccaggcgcc tctgtttatt cccccaatt ctgatcctgt    2760 acctgccaga gattatctta tattgaaagg agttttaaca gcaatgggtt tgataggaat    2820
catttgcctt attatagttg tgacacatca tactttaagc aggaaaaaga gagcagacaa    2880
gaaagagaat ggaacaaaat tattataaat aaatatccaa agtgtcttcc ttcttagata    2940
taagacccat ggccttcgac tacaaaaaca tactaacaaa gtcaaattaa catcaaaact    3000
gtattaaaat gcattgagtt tttgtacaat acagataaga ttttacatg gtagatcaac    3060 aaattctttt tgggggtaga ttagaaaacc cttacacttt ggctatgaac aaataataaa    3120
aattattctt taaagtaatg tcttttaagg caaagggaag ggtaaagtcg gaccagtgtc    3180
aaggaaagtt tgtttattg aggtggaaaa atagccccaa gcagagaaaa ggagggtagg    3240
tctgcattat aactgtctgt gtgaagcaat catttagtta ctttgattaa ttttctttt    3300 ctccttatct gtgcagaaca ggttgcttgt ttacaactga agatcatgct atatttcata    3360
tatgaagccc ctaatgcaaa gctctttacc tcttgctatt ttgttatata tattacagat    3420
gaaatctcac tgctaatgct cagagatctt ttttcactgt aagaggtaac ctttaacaat    3480
atgggtatta cctttgtctc ttcataccgg ttttatgaca aaggtctatt gaatttattt    3540
gtttgtaagt ttcactcccc atcaaagcag cttttttaagt tattgccttg gttattatgg    3600
```

```
atgatagtta tagcccttat aatgccttaa ctaaggaaga aaagatgtta ttctgagttt    3660
gttttaatac atatatgaac atatagtttt attcaattaa accaaagaag aggtcagcag    3720
ggagatacta acctttggaa atgattagct ggctctgttt tttggttaaa taagagtctt    3780
taatcctttc tccatcaaga gttacttacc aagggcaggg gaaggggat atagaggtcc     3840 caaggaaata aaaatcatct ttcatcttta attttactcc ttcctcttat ttttttaaaa    3900
gattatcgaa caataaaatc atttgccttt ttaattaaaa acataaaaaa a             3951
```

<210> SEQ ID NO 161
<211> LENGTH: 943
<212> TYPE: PRT
<213> ORGANISM: Homo sapien

<400> SEQUENCE: 161

```
Met Thr Gln Arg Ser Ile Ala Gly Pro Ile Cys Asn Leu Lys Phe Val
 1               5                  10                  15

Thr Leu Leu Val Ala Leu Ser Ser Glu Leu Pro Phe Leu Gly Ala Gly
                20                  25                  30

Val Gln Leu Gln Asp Asn Gly Tyr Asn Gly Leu Leu Ile Ala Ile Asn
            35                  40                  45

Pro Gln Val Pro Glu Asn Gln Asn Leu Ile Ser Asn Ile Lys Glu Met
        50                  55                  60

Ile Thr Glu Ala Ser Phe Tyr Leu Phe Asn Ala Thr Lys Arg Arg Val
65                  70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
                100                 105                 110

Val Thr Asp Trp Tyr Gly Ala His Gly Asp Asp Pro Tyr Thr Leu Gln
            115                 120                 125

Tyr Arg Gly Cys Gly Lys Glu Gly Lys Tyr Ile His Phe Thr Pro Asn
        130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
                180                 185                 190

Val Thr Arg Cys Ser Ser Asp Ile Thr Gly Ile Phe Val Cys Glu Lys
            195                 200                 205

Gly Pro Cys Pro Gln Glu Asn Cys Ile Ile Ser Lys Leu Phe Lys Glu
        210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
                260                 265                 270

Arg Ser Ala Trp Asp Val Ile Thr Asp Ser Ala Asp Phe His His Ser
            275                 280                 285

Phe Pro Met Asn Gly Thr Glu Leu Pro Pro Pro Thr Phe Ser Leu
        290                 295                 300

Val Glu Ala Gly Asp Lys Val Val Cys Leu Val Leu Asp Val Ser Ser
305                 310                 315                 320
```

-continued

```
Lys Met Ala Glu Ala Asp Arg Leu Leu Gln Leu Gln Gln Ala Glu
                325                 330                 335

Phe Tyr Leu Met Gln Ile Val Glu Ile His Thr Phe Val Gly Ile Ala
                340                 345                 350

Ser Phe Asp Ser Lys Gly Glu Ile Arg Ala Gln Leu His Gln Ile Asn
                355                 360                 365

Ser Asn Asp Asp Arg Lys Leu Leu Val Ser Tyr Leu Pro Thr Thr Val
    370                 375                 380

Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
                405                 410                 415

Leu Val Thr Ser Gly Asp Asp Lys Leu Leu Gly Asn Cys Leu Pro Thr
                420                 425                 430

Val Leu Ser Ser Gly Ser Thr Ile His Ser Ile Ala Leu Gly Ser Ser
                435                 440                 445

Ala Ala Pro Asn Leu Glu Glu Leu Ser Arg Leu Thr Gly Gly Leu Lys
                450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
                485                 490                 495

Leu Glu Ser Thr Gly Glu Asn Val Lys Pro His His Gln Leu Lys Asn
                500                 505                 510

Thr Val Thr Val Asp Asn Thr Val Gly Asn Asp Thr Met Phe Leu Val
                515                 520                 525

Thr Trp Gln Ala Ser Gly Pro Pro Glu Ile Ile Leu Phe Asp Pro Asp
                530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
                565                 570                 575

Tyr Thr Leu Asn Asn Thr His His Ser Leu Gln Ala Leu Lys Val Thr
                580                 585                 590

Val Thr Ser Arg Ala Ser Asn Ser Ala Val Pro Pro Ala Thr Val Glu
                595                 600                 605

Ala Phe Val Glu Arg Asp Ser Leu His Phe Pro His Pro Val Met Ile
                610                 615                 620

Tyr Ala Asn Val Lys Gln Gly Phe Tyr Pro Ile Leu Asn Ala Thr Val
625                 630                 635                 640

Thr Ala Thr Val Glu Pro Glu Thr Gly Asp Pro Val Thr Leu Arg Leu
                645                 650                 655

Leu Asp Asp Gly Ala Gly Ala Asp Val Ile Lys Asn Asp Gly Ile Tyr
                660                 665                 670

Ser Arg Tyr Phe Phe Ser Phe Ala Ala Asn Gly Arg Tyr Ser Leu Lys
                675                 680                 685

Val His Val Asn His Ser Pro Ser Ile Ser Thr Pro Ala His Ser Ile
                690                 695                 700

Pro Gly Ser His Ala Met Tyr Val Pro Gly Tyr Thr Ala Asn Gly Asn
705                 710                 715                 720

Ile Gln Met Asn Ala Pro Arg Lys Ser Val Gly Arg Asn Glu Glu Glu
                725                 730                 735
```

```
Arg Lys Trp Gly Phe Ser Arg Val Ser Ser Gly Gly Ser Phe Ser Val
            740                 745                 750
Leu Gly Val Pro Ala Gly Pro His Pro Asp Val Phe Pro Pro Cys Lys
            755                 760                 765
Ile Ile Asp Leu Glu Ala Val Lys Val Glu Glu Leu Thr Leu Ser
770                 775                 780
Trp Thr Ala Pro Gly Glu Asp Phe Asp Gln Gly Gln Ala Thr Ser Tyr
785                 790                 795                 800
Glu Ile Arg Met Ser Lys Ser Leu Gln Asn Ile Gln Asp Asp Phe Asn
                805                 810                 815
Asn Ala Ile Leu Val Asn Thr Ser Lys Arg Asn Pro Gln Gln Ala Gly
                820                 825                 830
Ile Arg Glu Ile Phe Thr Phe Ser Pro Gln Ile Ser Thr Asn Gly Pro
                835                 840                 845
Glu His Gln Pro Asn Gly Glu Thr His Glu Ser His Arg Ile Tyr Val
        850                 855                 860
Ala Ile Arg Ala Met Asp Arg Asn Ser Leu Gln Ser Ala Val Ser Asn
865                 870                 875                 880
Ile Ala Gln Ala Pro Leu Phe Ile Pro Pro Asn Ser Asp Pro Val Pro
                885                 890                 895
Ala Arg Asp Tyr Leu Ile Leu Lys Gly Val Leu Thr Ala Met Gly Leu
                900                 905                 910
Ile Gly Ile Ile Cys Leu Ile Ile Val Val Thr His His Thr Leu Ser
            915                 920                 925
Arg Lys Lys Arg Ala Asp Lys Lys Glu Asn Gly Thr Lys Leu Leu
            930                 935                 940
```

<210> SEQ ID NO 162
<211> LENGTH: 498
<212> TYPE: DNA
<213> ORGANISM: Homo sapien

<400> SEQUENCE: 162

```
tggagaacca cgtggacagc accatgaaca tgttgggcgg gggaggcagt gctggccgga      60
agcccctcaa gtcgggtatg aaggagctgg ccgtgttccg ggagaaggtc actgagcagc     120
accggcagat gggcaagggt ggcaagcatc accttggcct ggaggagccc aagaagctgc     180
gaccaccccc tgccaggact ccctgccaac aggaactgga ccaggtcctg gagcggatct     240
ccaccatgcg ccttccggat gagcggggcc tctggagca cctctactcc ctgcacatcc      300
ccaactgtga caagcatggc ctgtacaacc tcaaacagtg gcaagatgtc tctgaacggg     360
cagcgtgggg agtgctggtg tgtgaacccc aacaccggga agctgatcca gggagccccc     420
accatccggg gggaccccga gtgtcatctc ttctacaatg agcagcagga ggctcgcggg     480
gtgcacaccc cagcggat                                                   498
```

<210> SEQ ID NO 163
<211> LENGTH: 1128
<212> TYPE: DNA
<213> ORGANISM: Homo sapien

<400> SEQUENCE: 163

```
gccacctggc cctcctgatc gacgacacac gcacttgaaa cttgttctca gggtgtgtgg      60
aatcaacttt ccggaagcaa ccagcccacc agaggaggtc ccgagcgcga gcggagacga     120
tgcagcggag actggttcag cagtggagcg tcgcggtgtt cctgctgagc tacgcggtgc     180
```

-continued

```
cctcctgcgg gcgctcggtg gagggtctca gccgccgcct caaaagagct gtgtctgaac      240
atcagctcct ccatgacaag gggaagtcca tccaagattt acggcgacga ttcttccttc      300
accatctgat cgcagaaatc cacacagctg aaatcagagc tacctcggag gtgtccccta      360
actccaagcc ctctcccaac acaaagaacc accccgtccg atttgggtct gatgatgagg      420
gcagatacct aactcaggaa actaacaagg tggagacgta caaagagcag ccgctcaaga      480
cacctgggaa gaaaagaaa ggcaagcccg gaaacgcaa ggagcaggaa aagaaaaaac        540
ggcgaactcg ctctgcctgg ttagactctg gagtgactgg gagtgggcta aaggggacc       600 acctgtctga cacctccaca acgtcgctgg agctcgattc acggaggcat tgaaattttc      660
agcagagacc ttccaaggac atattgcagg attctgtaat agtgaacata tggaaagtat      720
tagaaatatt tattgtctgt aaatactgta aatgcattgg aataaaactg tctcccccat      780
tgctctatga aactgcacat tggtcattgt gaatattttt tttttgcca aggctaatcc        840 aattattatt atcacatttta ccataattta ttttgtccat tgatgtattt attttgtaaa     900
tgtatcttgg tgctgctgaa tttctatatt ttttgtaaca aatgcactt tagatataca       960 tatcaagtat gttgataaat gacacaatga agtgtctcta ttttgtggtt gattttaatg     1020
aatgcctaaa tataattatc caaattgatt ttcctttgtg catgtaaaaa taacagtatt     1080
ttaaatttgt aaagaatgtc taataaaata taatctaatt acatcatg                  1128
```

<210> SEQ ID NO 164
<211> LENGTH: 1310
<212> TYPE: DNA
<213> ORGANISM: Homo sapien

<400> SEQUENCE: 164

```
gggcctggtt cgcaaagaag ctgacttcag aggggaaac tttcttcttt taggaggcgg        60
ttagccctgt tccacgaacc caggagaact gctggccaga ttaattagac attgctatgg      120
gagacgtgta aacacactac ttatcattga tgcatatata aaaccatttt attttcgcta      180
ttatttcaga ggaagcgcct ctgatttgtt tctttttcc cttttttgctc tttctggctg      240 tgtggtttgg agaaagcaca gttggagtag ccggttgcta aataagtccc gagcgcgagc      300
ggagacgatg cagcggagac tggttcagca gtggagcgtc gcggtgttcc tgctgagcta      360
cgcggtgccc tcctgcgggc gctcggtgga gggtctcagc cgccgcctca aaagagctgt      420
gtctgaacat cagctcctcc atgacaaggg gaagtccatc caagatttac ggcgacgatt      480
cttccttcac catctgatcg cagaaatcca cacagctgaa atcagagcta cctcggaggt      540 gtccctaac tccaagccct ctcccaacac aaagaaccac cccgtccgat ttgggtctga       600
tgatgagggc agatacctaa ctcaggaaac taacaaggtg gagacgtaca agagcagcc       660 gctcaagaca cctgggaaga aaagaaagg caagcccggg aaacgcaagg agcaggaaaa      720
gaaaaaacgg cgaactcgct ctgcctggtt agactctgga gtgactggga gtgggctaga    780
aggggaccac ctgtctgaca cctccacaac gtcgctggag ctcgattcac ggaggcattg    840
aaattttcag cagagacctt ccaaggacat attgcaggat tctgtaatag tgaacatatg    900
gaaagtatta gaaatattta ttgtctgtaa atactgtaaa tgcattggaa taaaactgtc    960
tcccccattg ctctatgaaa ctgcacattg gtcattgtga atattttttt ttttgccaag   1020
gctaatccaa ttattattat cacatttacc ataatttatt ttgtccattg atgtatttat   1080
tttgtaaatg tatcttggtg ctgctgaatt tctatatttt ttgtaacata atgcacttta   1140
gatatacata tcaagtatgt tgataaatga cacaatgaag tgtctctatt ttgtggttga   1200
```

```
tttaatgaa tgcctaaata taattatcca aattgatttt cctttgtgcc cgtaaaaata    1260
acagtatttt aaatttgtaa agaatgtcta ataaaatata atctaattac              1310
```

<210> SEQ ID NO 165
<211> LENGTH: 177
<212> TYPE: PRT
<213> ORGANISM: Homo sapien

<400> SEQUENCE: 165

Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 166
<211> LENGTH: 177
<212> TYPE: PRT
<213> ORGANISM: Homo sapien

<400> SEQUENCE: 166

Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

```
Lys Pro Gly Lys Arg Lys Glu Gln Glu Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 167
<211> LENGTH: 3362
<212> TYPE: DNA
<213> ORGANISM: Homo sapien

<400> SEQUENCE: 167
```

| | | | | | |
|---|---|---|---|---|---|
| cacaatgtat | gcagcaggct | cagtgtgagt | gaactggagg | cttctctaca | acatgaccca | 60 |
| aaggagcatt | gcaggtccta | tttgcaacct | gaagtttgtg | actctcctgg | ttgccttaag | 120 |
| ttcagaactc | ccattcctgg | gagctggagt | acagcttcaa | gacaatgggt | ataatggatt | 180 |
| gctcattgca | attaatcctc | aggtacctga | gaatcagaac | ctcatctcaa | acattaagga | 240 |
| aatgataact | gaagcttcat | tttacctatt | taatgctacc | aagagaagag | tattttttcag | 300 |
| aaatataaag | attttaatac | ctgccacatg | gaaagctaat | aataacagca | aaataaaaca | 360 |
| agaatcatat | gaaaaggcaa | atgtcatagt | gactgactgg | tatgggcac | atggagatga | 420 |
| tccatacacc | ctacaataca | gagggtgtgg | aaaagaggga | aaatacattc | atttcacacc | 480 |
| taatttccta | ctgaatgata | acttaacagc | tggctacgga | tcacgaggcc | gagtgtttgt | 540 |
| ccatgaatgg | gcccacctcc | gttggggtgt | gttcgatgag | tataacaatg | acaaacccttt | 600 |
| ctacataaat | gggcaaaatc | aaattaaagt | gacaaggtgt | tcatctgaca | tcacaggcat | 660 |
| ttttgtgtgt | gaaaaaggtc | cttgccccca | agaaaactgt | attattagta | agcttttttaa | 720 |
| agaaggatgc | acctttatct | acaatagcac | ccaaaatgca | actgcatcaa | taatgttcat | 780 |
| gcaaagttta | tcttctgtgg | ttgaattttg | taatgcaagt | acccacaacc | aagaagcacc | 840 |
| aaacctacag | aaccagatgt | gcagcctcag | aagtgcatgg | gatgtaatca | cagactctgc | 900 |
| tgactttcac | cacagctttc | ccatgaacgg | gactgagctt | ccacctcctc | ccacattctc | 960 |
| gcttgtagag | gctggtgaca | agtggtctg | tttagtgctg | gatgtgtcca | gcaagatggc | 1020 |
| agaggctgac | agactccttc | aactacaaca | agccgcagaa | ttttatttga | tgcagattgt | 1080 |
| tgaaattcat | accttcgtgg | gcattgccag | tttcgacagc | aaaggagaga | tcagagccca | 1140 |
| gctacaccaa | attaacagca | atgatgatcg | aaagttgctg | gtttcatatc | tgcccaccac | 1200 |
| tgtatcagct | aaaacagaca | tcagcatttg | ttcagggctt | aagaaggat | ttgaggtggt | 1260 |
| tgaaaaactg | aatggaaag | cttatggctc | tgtgatgata | ttagtgacca | gcggagatga | 1320 |
| taagcttctt | ggcaattgct | tacccactgt | gctcagcagt | ggttcaacaa | ttcactccat | 1380 |
| tgccctgggt | tcatctgcag | ccccaaatct | ggaggaatta | tcacgtctta | caggaggttt | 1440 |
| aaagttcttt | gttccagata | tatcaaactc | caatagcatg | attgatgctt | tcagtagaat | 1500 |
| ttcctctgga | actggagaca | ttttccagca | acatattcag | cttgaaagta | caggtgaaaa | 1560 |
| tgtcaaacct | caccatcaat | tgaaaaacac | agtgactgtg | gataatactg | tgggcaacga | 1620 |
| cactatgttt | ctagttacgt | ggcaggccag | tggtcctcct | gagattatat | tatttgatcc | 1680 |
| tgatggacga | aaatactaca | caaataattt | tatcaccaat | ctaactttttc | ggacagctag | 1740 |
| tctttggatt | ccaggaacag | ctaagcctgg | gcactggact | tacaccctga | tgtgtttcca | 1800 |

-continued

```
ccatgcaaaa ttattgacct ggaagctgta aaagtagaag aggaattgac cctatcttgg   1860
acagcacctg agaagactt tgatcagggc caggctacaa gctatgaaat aagaatgagt   1920
aaaagtctac agaatatcca agatgacttt aacaatgcta ttttagtaaa tacatcaaag   1980
cgaaatcctc agcaagctgg catcagggag atatttacgt tctcaccca aatttccacg   2040 aatggacctg aacatcagcc aaatggaaa acacatgaaa gccacagaat ttatgttgca   2100
atacgagcaa tggataggaa ctccttacag tctgctgtat ctaacattgc ccaggcgcct   2160
ctgtttattc cccccaattc tgatcctgta cctgccagag attatcttat attgaaagga   2220
gttttaacag caatgggttt gataggaatc atttgcctta ttatagttgt gacacatcat   2280
actttaagca ggaaaaagag agcagacaag aaagagaatg gaacaaaatt attataaata   2340
aatatccaaa gtgtcttcct tcttagatat aagacccatg gccttcgact acaaaaacat   2400
actaacaaag tcaaattaac atcaaaactg tattaaaatg cattgagttt ttgtacaata   2460
cagataagat ttttacatgg tagatcaaca aattcttttt gggggtagat tagaaaaccc   2520
ttacactttg gctatgaaca ataataaaa attattcttt aaagtaatgt ctttaaaggc   2580
aaagggaagg gtaaagtcgg accagtgtca aggaaagttt gttttattga ggtggaaaaa   2640
tagccccaag cagagaaaag gagggtaggt ctgcattata actgtctgtg tgaagcaatc   2700
atttagttac tttgattaat ttttcttttc tccttatctg tgcagaacag gttgcttgtt   2760
tacaactgaa gatcatgcta tatttcatat atgaagcccc taatgcaaag ctctttacct   2820
cttgctattt tgttatatat attacagatg aaatctcact gctaatgctc agagatcttt   2880
tttcactgta agaggtaacc tttaacaata tgggtattac ctttgtctct tcataccggt   2940
tttatgacaa aggtctattg aatttatttg tttgtaagtt tctactccca tcaaagcagc   3000
tttctaagtt attgccttgg ttattatgga tgatagttat agcccttata atgccttaac   3060
taaggaagaa aagatgttat tctgagtttg ttttaataca tatatgaaca tatagttta   3120 ttcaattaaa ccaaagaaga ggtcagcagg gagatactaa cctttggaaa tgattagctg   3180
gctctgtttt tggttaaat aagagtcttt aatcctttct ccatcaagag ttacttacca   3240
agggcagggg aaggggata tagaggtcac aaggaaataa aaatcatctt tcatctttaa   3300
ttttactcct cctcttatt tttttaaaag attatcgaac aataaaatca tttgccttt   3360 tt                                                                  3362
```

<210> SEQ ID NO 168
<211> LENGTH: 2784
<212> TYPE: DNA
<213> ORGANISM: Homo sapien

<400> SEQUENCE: 168

```
tctgcatcca tattgaaaac ctgacacaat gtatgcagca ggctcagtgt gagtgaactg    60
gaggcttctc tacaacatga cccaaaggag cattgcaggt cctatttgca acctgaagtt   120
tgtgactctc ctggttgcct taagttcaga actcccattc ctgggagctg gagtacagct   180
tcaagacaat gggtataatg gattgctcat tgcaattaat cctcaggtac ctgagaatca   240
gaacctcatc tcaaacatta aggaaatgat aactgaagct tcattttacc tatttaatgc   300
taccaagaga agagtatttt tcagaaatat aaagatttta atacctgcca catggaaagc   360
taataataac agcaaaataa aacaagaatc atatgaaaag gcaaatgtca tagtgactga   420
ctggtatggg gcacatggag atgatccata caccctacaa tacagagggt gtggaaaaga   480
```

-continued

```
gggaaaatac attcatttca cacctaatttt cctactgaat gataacttaa cagctggcta      540
cggatcacga ggccgagtgt tgtccatga atgggcccac ctccgttggg gtgtgttcga       600
tgagtataac aatgacaaac ctttctacat aaatgggcaa atcaaatta aagtgacaag       660
gtgttcatct gacatcacag gcattttttgt gtgtgaaaaa ggtccttgcc cccaagaaaa    720
ctgtattatt agtaagcttt ttaaagaagg atgcacctt atctacaata gcacccaaaa      780
tgcaactgca tcaataatgt tcatgcaaag tttatcttct gtggttgaat tttgtaatgc     840
aagtacccac aaccaagaag caccaaacct acagaaccag atgtgcagcc tcagaagtgc     900
atgggatgta atcacagact ctgctgactt tcaccacagc tttcccatga acgggactga     960
gcttccacct cctcccacat tctcgcttgt agaggctggt gacaaagtgg tctgtttagt    1020
gctggatgtg tccagcaaga tggcagaggc tgacagactc cttcaactac aacaagccgc    1080
agaattttat tgatgcaga ttgttgaaat tcataccttc gtgggcattg ccagtttcga     1140
cagcaaagga gagatcagag cccagctaca ccaaattaac agcaatgatg atcgaaagtt    1200
gctggtttca tatctgccca ccactgtatc agctaaaaca gacatcagca tttgttcagg    1260
gcttaagaaa ggatttgagg tggttgaaaa actgaatgga aaagcttatg ctctgtgat    1320
gatattagtg accagcggag atgataagct tcttggcaat gcttaccca ctgtgctcag    1380
cagtggttca acaattcact ccattgccct gggttcatct gcagcccaa atctggagga    1440
attatcacgt cttacaggag gtttaaagtt ctttgttcca gatatatcaa actccaatag    1500
catgattgat gctttcagta gaatttcctc tggaactgga gacatttttcc agcaacatat   1560
tcagcttgaa agtacaggtg aaaatgtcaa acctcaccat caattgaaaa acacagtgac    1620
tgtggataat actgtgggca acgacactat gtttctagtt acgtggcagg ccagtggtcc    1680
tcctgagatt atattatttg atcctgatgg acgaaaatac tacacaaata attttatcac    1740
caatctaact tttcggacag ctagtctttg gattccagga acagctaagc ctgggcactg    1800
gacttacacc ctgaacaata cccatcattc tctgcaagcc ctgaaagtga cagtgacctc    1860
tcgcgcctcc aactcagctg tgcccccagc cactgtggaa gcctttgtgg aaagagacag    1920
cctccatttt cctcatcctg tgatgattta tgccaatgtg aaacagggat tttatcccat    1980
tcttaatgcc actgtcactg ccacagttga gccagagact ggagatcctg ttacgctgag    2040
actccttgat gatggagcag gtgctgatgt tataaaaaat gatggaattt actcgaggta    2100
ttttttctcc tttgctgcaa atggtagata tagcttgaaa gtgcatgtca atcactctcc    2160
cagcataagc accccagccc actctattcc agggagtcat gctatgtatg taccaggtta    2220
cacagcaaac ggtaatattc agatgaatgc tccaaggaaa tcagtaggca gaaatgagga    2280
ggagcgaaag tggggcttta gccgagtcag ctcaggaggc tccttttcag tgctgggagt    2340
tccagctggc ccccaccctg atgtgtttcc accatgcaaa attattgacc tggaagctgt    2400
aaatagaaga ggaattgacc ctatcttgga cagcacctgg agaagacttt gatcagggcc    2460
aggctacaag ctatgaaata agaatgagta aaagtctaca gaatatccaa gatgacttta    2520
acaatgctat tttagtaaat acatcaaagc gaaatcctca gcaagctggc atcagggaga    2580
tatttacgtt ctcaccccaa atttccacga atggacctga acatcagcca aatggagaaa    2640
cacatgaaag ccacagaatt tatgttgcaa tacgagcaat ggataggaac tccttacagt    2700
ctgctgtatc taacattgcc caggcgcctc tgtttattcc ccccaattct gatcctgtac    2760
ctgccagaga ttatcttata ttga                                            2784
```

<210> SEQ ID NO 169
<211> LENGTH: 592
<212> TYPE: PRT
<213> ORGANISM: Homo sapien

<400> SEQUENCE: 169

```
Met Thr Gln Arg Ser Ile Ala Gly Pro Ile Cys Asn Leu Lys Phe Val
 1               5                  10                  15

Thr Leu Leu Val Ala Leu Ser Ser Glu Leu Pro Phe Leu Gly Ala Gly
             20                  25                  30

Val Gln Leu Gln Asp Asn Gly Tyr Asn Gly Leu Leu Ile Ala Ile Asn
         35                  40                  45

Pro Gln Val Pro Glu Asn Gln Asn Leu Ile Ser Asn Ile Lys Glu Met
     50                  55                  60

Ile Thr Glu Ala Ser Phe Tyr Leu Phe Asn Ala Thr Lys Arg Arg Val
 65                  70                  75                  80

Phe Phe Arg Asn Ile Lys Ile Leu Ile Pro Ala Thr Trp Lys Ala Asn
                 85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175

Tyr Asn Asn Asp Lys Pro Phe Tyr Ile Asn Gly Gln Asn Gln Ile Lys
            180                 185                 190

Val Thr Arg Cys Ser Ser Asp Ile Thr Gly Ile Phe Val Cys Glu Lys
        195                 200                 205

Gly Pro Cys Pro Gln Glu Asn Cys Ile Ile Ser Lys Leu Phe Lys Glu
    210                 215                 220

Gly Cys Thr Phe Ile Tyr Asn Ser Thr Gln Asn Ala Thr Ala Ser Ile
225                 230                 235                 240

Met Phe Met Gln Ser Leu Ser Ser Val Val Glu Phe Cys Asn Ala Ser
                245                 250                 255

Thr His Asn Gln Glu Ala Pro Asn Leu Gln Asn Gln Met Cys Ser Leu
            260                 265                 270

Arg Ser Ala Trp Asp Val Ile Thr Asp Ser Ala Asp Phe His His Ser
        275                 280                 285

Phe Pro Met Asn Gly Thr Glu Leu Pro Pro Pro Thr Phe Ser Leu
    290                 295                 300

Val Glu Ala Gly Asp Lys Val Val Cys Leu Val Leu Asp Val Ser Ser
305                 310                 315                 320

Lys Met Ala Glu Ala Asp Arg Leu Leu Gln Leu Gln Gln Ala Ala Glu
                325                 330                 335

Phe Tyr Leu Met Gln Ile Val Glu Ile His Thr Phe Val Gly Ile Ala
            340                 345                 350

Ser Phe Asp Ser Lys Gly Glu Ile Arg Ala Gln Leu His Gln Ile Asn
        355                 360                 365

Ser Asn Asp Asp Arg Lys Leu Leu Val Ser Tyr Leu Pro Thr Thr Val
    370                 375                 380
```

-continued

```
Ser Ala Lys Thr Asp Ile Ser Ile Cys Ser Gly Leu Lys Lys Gly Phe
385                 390                 395                 400

Glu Val Val Glu Lys Leu Asn Gly Lys Ala Tyr Gly Ser Val Met Ile
            405                 410                 415

Leu Val Thr Ser Gly Asp Asp Lys Leu Leu Gly Asn Cys Leu Pro Thr
        420                 425                 430

Val Leu Ser Ser Gly Ser Thr Ile His Ser Ile Ala Leu Gly Ser Ser
    435                 440                 445

Ala Ala Pro Asn Leu Glu Glu Leu Ser Arg Leu Thr Gly Gly Leu Lys
450                 455                 460

Phe Phe Val Pro Asp Ile Ser Asn Ser Asn Ser Met Ile Asp Ala Phe
465                 470                 475                 480

Ser Arg Ile Ser Ser Gly Thr Gly Asp Ile Phe Gln Gln His Ile Gln
            485                 490                 495

Leu Glu Ser Thr Gly Glu Asn Val Lys Pro His His Gln Leu Lys Asn
        500                 505                 510

Thr Val Thr Val Asp Asn Thr Val Gly Asn Asp Thr Met Phe Leu Val
    515                 520                 525

Thr Trp Gln Ala Ser Gly Pro Pro Glu Ile Ile Leu Phe Asp Pro Asp
530                 535                 540

Gly Arg Lys Tyr Tyr Thr Asn Asn Phe Ile Thr Asn Leu Thr Phe Arg
545                 550                 555                 560

Thr Ala Ser Leu Trp Ile Pro Gly Thr Ala Lys Pro Gly His Trp Thr
            565                 570                 575

Tyr Thr Leu Met Cys Phe His His Ala Lys Leu Leu Thr Trp Lys Leu
        580                 585                 590

<210> SEQ ID NO 170
<211> LENGTH: 791
<212> TYPE: PRT
<213> ORGANISM: Homo sapien

<400> SEQUENCE: 170

Met Thr Gln Arg Ser Ile Ala Gly Pro Ile Cys Asn Leu Lys Phe Val
1               5                   10                  15

Thr Leu Leu Val Ala Leu Ser Ser Glu Leu Pro Phe Leu Gly Ala Gly
            20                  25                  30

Val Gln Leu Gln Asp Asn Gly Tyr Asn Gly Leu Leu Ile Ala Ile Asn
        35                  40                  45

Pro Gln Val Pro Glu Asn Gln Asn Leu Ile Ser Asn Ile Lys Glu Met
    50                  55                  60

Ile Thr Glu Ala Ser Phe Tyr Leu Phe Asn Ala Thr Lys Arg Arg Val
65              70                  75                  80

Phe Phe Arg Asn Ile Lys Ile Leu Ile Pro Ala Thr Trp Lys Ala Asn
                85                  90                  95

Asn Asn Ser Lys Ile Lys Gln Glu Ser Tyr Glu Lys Ala Asn Val Ile
            100                 105                 110

Val Thr Asp Trp Tyr Gly Ala His Gly Asp Asp Pro Tyr Thr Leu Gln
        115                 120                 125

Tyr Arg Gly Cys Gly Lys Glu Gly Lys Tyr Ile His Phe Thr Pro Asn
    130                 135                 140

Phe Leu Leu Asn Asp Asn Leu Thr Ala Gly Tyr Gly Ser Arg Gly Arg
145                 150                 155                 160

Val Phe Val His Glu Trp Ala His Leu Arg Trp Gly Val Phe Asp Glu
                165                 170                 175
```

-continued

```
Tyr Asn Asn Asp Lys Pro Phe Tyr Ile Asn Gly Gln Asn Gln Ile Lys
            180                 185                 190
Val Thr Arg Cys Ser Ser Asp Ile Thr Gly Ile Phe Val Cys Glu Lys
            195                 200             205
Gly Pro Cys Pro Gln Glu Asn Cys Ile Ile Ser Lys Leu Phe Lys Glu
            210                 215                 220
Gly Cys Thr Phe Ile Tyr Asn Ser Thr Gln Asn Ala Thr Ala Ser Ile
225                 230                 235                 240
Met Phe Met Gln Ser Leu Ser Ser Val Val Glu Phe Cys Asn Ala Ser
            245                 250                 255
Thr His Asn Gln Glu Ala Pro Asn Leu Gln Asn Gln Met Cys Ser Leu
            260                 265                 270
Arg Ser Ala Trp Asp Val Ile Thr Asp Ser Ala Asp Phe His His Ser
            275                 280                 285
Phe Pro Met Asn Gly Thr Glu Leu Pro Pro Pro Thr Phe Ser Leu
            290                 295                 300
Val Glu Ala Gly Asp Lys Val Val Cys Leu Val Leu Asp Val Ser Ser
305                 310                 315                 320
Lys Met Ala Glu Ala Asp Arg Leu Leu Gln Leu Gln Ala Ala Glu
            325                 330                 335
Phe Tyr Leu Met Gln Ile Val Glu Ile His Thr Phe Val Gly Ile Ala
            340                 345                 350
Ser Phe Asp Ser Lys Gly Glu Ile Arg Ala Gln Leu His Gln Ile Asn
            355                 360                 365
Ser Asn Asp Asp Arg Lys Leu Leu Val Ser Tyr Leu Pro Thr Thr Val
            370                 375                 380
Ser Ala Lys Thr Asp Ile Ser Ile Cys Ser Gly Leu Lys Lys Gly Phe
385                 390                 395                 400
Glu Val Val Glu Lys Leu Asn Gly Lys Ala Tyr Gly Ser Val Met Ile
            405                 410                 415
Leu Val Thr Ser Gly Asp Asp Lys Leu Leu Gly Asn Cys Leu Pro Thr
            420                 425                 430
Val Leu Ser Ser Gly Ser Thr Ile His Ser Ile Ala Leu Gly Ser Ser
            435                 440                 445
Ala Ala Pro Asn Leu Glu Glu Leu Ser Arg Leu Thr Gly Gly Leu Lys
            450                 455                 460
Phe Phe Val Pro Asp Ile Ser Asn Ser Asn Ser Met Ile Asp Ala Phe
465                 470                 475                 480
Ser Arg Ile Ser Ser Gly Thr Gly Asp Ile Phe Gln Gln His Ile Gln
            485                 490                 495
Leu Glu Ser Thr Gly Glu Asn Val Lys Pro His His Gln Leu Lys Asn
            500                 505                 510
Thr Val Thr Val Asp Asn Thr Val Gly Asn Asp Thr Met Phe Leu Val
            515                 520                 525
Thr Trp Gln Ala Ser Gly Pro Pro Glu Ile Ile Leu Phe Asp Pro Asp
            530                 535                 540
Gly Arg Lys Tyr Tyr Thr Asn Asn Phe Ile Thr Asn Leu Thr Phe Arg
545                 550                 555                 560
Thr Ala Ser Leu Trp Ile Pro Gly Thr Ala Lys Pro Gly His Trp Thr
            565                 570                 575
Tyr Thr Leu Asn Asn Thr His His Ser Leu Gln Ala Leu Lys Val Thr
            580                 585                 590
```

```
Val Thr Ser Arg Ala Ser Asn Ser Ala Val Pro Pro Ala Thr Val Glu
        595                 600                 605
Ala Phe Val Glu Arg Asp Ser Leu His Phe Pro His Pro Val Met Ile
    610                 615                 620
Tyr Ala Asn Val Lys Gln Gly Phe Tyr Pro Ile Leu Asn Ala Thr Val
625                 630                 635                 640
Thr Ala Thr Val Glu Pro Glu Thr Gly Asp Pro Val Thr Leu Arg Leu
                645                 650                 655
Leu Asp Asp Gly Ala Gly Ala Asp Val Ile Lys Asn Asp Gly Ile Tyr
            660                 665                 670
Ser Arg Tyr Phe Phe Ser Phe Ala Ala Asn Gly Arg Tyr Ser Leu Lys
        675                 680                 685
Val His Val Asn His Ser Pro Ser Ile Ser Thr Pro Ala His Ser Ile
    690                 695                 700
Pro Gly Ser His Ala Met Tyr Val Pro Gly Tyr Thr Ala Asn Gly Asn
705                 710                 715                 720
Ile Gln Met Asn Ala Pro Arg Lys Ser Val Gly Arg Asn Glu Glu Glu
                725                 730                 735
Arg Lys Trp Gly Phe Ser Arg Val Ser Ser Gly Ser Phe Ser Val
            740                 745                 750
Leu Gly Val Pro Ala Gly Pro His Pro Asp Val Phe Pro Pro Cys Lys
        755                 760                 765
Ile Ile Asp Leu Glu Ala Val Asn Arg Arg Gly Ile Asp Pro Ile Leu
    770                 775                 780
Asp Ser Thr Trp Arg Arg Leu
785                 790

<210> SEQ ID NO 171
<211> LENGTH: 1491
<212> TYPE: DNA
<213> ORGANISM: Homo sapien

<400> SEQUENCE: 171
cctcctgcca gccaagtgaa gacatgctta cttcccctc accttccttc atgatgtggg      60
aagagtgctg caacccagcc ctagccaacg ccgcatgaga gggagtgtgc cgagggcttc     120
tgagaaggtt tctctcacat ctagaaagaa gcgcttaaga tgtggcagcc cctcttcttc     180
aagtggctct tgtcctgttg ccctgggagt tctcaaattg ctgcagcagc ctccacccag     240
cctgaggatg acatcaatac acagaggaag aagagtcagg aaaagatgag agaagttaca     300
gactctcctg ggcgaccccg agagcttacc attcctcaga cttcttcaca tggtgctaac     360
agatttgttc ctaaaagtaa agctctagag gccgtcaaat tggcaataga agccgggttc     420
caccatattg attctgcaca tgtttacaat aatgaggagc aggttggact ggccatccga     480
agcaagattg cagatggcag tgtgaagaga gaagacatat tctacacttc aaagctttgg     540
agcaattccc atcgaccaga gttggtccga ccagccttgg aaaggtcact gaaaaatctt     600
caattggact atgttgacct ctatcttatt cattttccag tgtctgtaaa gccaggtgag     660
gaagtgatcc caaaagatga aaatggaaaa atactatttg acacagtgga tctctgtgcc     720
acatgggagg ccatggagaa gtgtaaagat gcaggattgg ccaagtccat cggggtgtcc     780
aacttcaacc acaggctgct ggagatgatc ctcaacaagc cagggctcaa gtacaagcct     840
gtctgcaacc aggtggaatg tcatccttac ttcaaccaga gaaaactgct ggatttctgc     900
aagtcaaaag acattgttct ggttgcctat agtgctctgg gatcccatcg agaagaacca    960
```

-continued

```
tgggtggacc cgaactcccc ggtgctcttg gaggacccag tcctttgtgc cttggcaaaa      1020
aagcacaagc gaacccccagc cctgattgcc ctgcgctacc agctgcagcg tggggttgtg    1080
gtcctggcca agagctacaa tgagcagcgc atcagacaga acgtgcaggt gtttgaattc      1140
cagttgactt cagaggagat gaaagccata gatggcctaa acagaaatgt gcgatatttg      1200
acccttgata tttttgctgg cccccctaat tatccatttt ctgatgaata ttaacatgga      1260
gggcattgca tgaggtctgc cagaaggccc tgcgtgtgga tggtgacaca gaggatggct      1320
ctatgctggt gactggacac atcgcctctg gttaaatctc tcctgcttgg cgacttcagt      1380
aagctacagc taagcccatc ggccggaaaa gaaagacaat aattttgttt ttcattttga      1440
aaaaattaaa tgctctctcc taaagattct tcacctaaaa aaaaaaaaa a                1491
```

<210> SEQ ID NO 172
<211> LENGTH: 364
<212> TYPE: PRT
<213> ORGANISM: Homo sapien

<400> SEQUENCE: 172

```
Met Trp Gln Pro Leu Phe Phe Lys Trp Leu Leu Ser Cys Cys Pro Gly
 1               5                  10                  15

Ser Ser Gln Ile Ala Ala Ala Ser Thr Gln Pro Glu Asp Asp Ile
            20                  25                  30

Asn Thr Gln Arg Lys Lys Ser Gln Glu Lys Met Arg Glu Val Thr Asp
        35                  40                  45

Ser Pro Gly Arg Pro Arg Glu Leu Thr Ile Pro Gln Thr Ser Ser His
    50                  55                  60

Gly Ala Asn Arg Phe Val Pro Lys Ser Lys Ala Leu Glu Ala Val Lys
65                  70                  75                  80

Leu Ala Ile Glu Ala Gly Phe His His Ile Asp Ser Ala His Val Tyr
                85                  90                  95

Asn Asn Glu Glu Gln Val Gly Leu Ala Ile Arg Ser Lys Ile Ala Asp
            100                 105                 110

Gly Ser Val Lys Arg Glu Asp Ile Phe Tyr Thr Ser Lys Leu Trp Ser
        115                 120                 125

Asn Ser His Arg Pro Glu Leu Val Arg Pro Ala Leu Glu Arg Ser Leu
    130                 135                 140

Lys Asn Leu Gln Leu Asp Tyr Val Asp Leu Tyr Leu Ile His Phe Pro
145                 150                 155                 160

Val Ser Val Lys Pro Gly Glu Glu Val Ile Pro Lys Asp Glu Asn Gly
                165                 170                 175

Lys Ile Leu Phe Asp Thr Val Asp Leu Cys Ala Thr Trp Glu Ala Met
            180                 185                 190

Glu Lys Cys Lys Asp Ala Gly Leu Ala Lys Ser Ile Gly Val Ser Asn
        195                 200                 205

Phe Asn His Arg Leu Leu Glu Met Ile Leu Asn Lys Pro Gly Leu Lys
    210                 215                 220

Tyr Lys Pro Val Cys Asn Gln Val Glu Cys His Pro Tyr Phe Asn Gln
225                 230                 235                 240

Arg Lys Leu Leu Asp Phe Cys Lys Ser Lys Asp Ile Val Leu Val Ala
                245                 250                 255

Tyr Ser Ala Leu Gly Ser His Arg Glu Glu Pro Trp Val Asp Pro Asn
            260                 265                 270

Ser Pro Val Leu Leu Glu Asp Pro Val Leu Cys Ala Leu Ala Lys Lys
        275                 280                 285
```

-continued

```
His Lys Arg Thr Pro Ala Leu Ile Ala Leu Arg Tyr Gln Leu Gln Arg
    290                 295                 300

Gly Val Val Val Leu Ala Lys Ser Tyr Asn Glu Gln Arg Ile Arg Gln
305                 310                 315                 320

Asn Val Gln Val Phe Glu Phe Gln Leu Thr Ser Glu Glu Met Lys Ala
                325                 330                 335

Ile Asp Gly Leu Asn Arg Asn Val Arg Tyr Leu Thr Leu Asp Ile Phe
            340                 345                 350

Ala Gly Pro Pro Asn Tyr Pro Phe Ser Asp Glu Tyr
        355                 360
```